US009046538B2

(12) United States Patent
Laaksonen et al.

(10) Patent No.: US 9,046,538 B2
(45) Date of Patent: Jun. 2, 2015

(54) LIPIDOMIC BIOMARKERS FOR ATHEROSCLEROSIS AND CARDIOVASCULAR DISEASE

(75) Inventors: Reijo Laaksonen, Lempäälä (FI); Kim Ekroos, Helsinki (FI); Reini Hurme, Espoo (FI); Minna Janis, Espoo (FI); Riika Katainen, Helsinki (FI); Kirill Tarasov, Espoo (FI)

(73) Assignee: ZORA BIOSCIENCES OY, Espoo (FI)

( * ) Notice: Subject to any disclaimer, the term of this patent is extended or adjusted under 35 U.S.C. 154(b) by 0 days.

(21) Appl. No.: 13/695,766

(22) PCT Filed: May 5, 2011

(86) PCT No.: PCT/EP2011/057254
§ 371 (c)(1),
(2), (4) Date: Nov. 1, 2012

(87) PCT Pub. No.: WO2011/138419
PCT Pub. Date: Nov. 10, 2011

(65) Prior Publication Data
US 2013/0045217 A1 Feb. 21, 2013

Related U.S. Application Data

(60) Provisional application No. 61/331,463, filed on May 5, 2010.

(30) Foreign Application Priority Data

May 5, 2010 (EP) .................................... 10162066

(51) Int. Cl.
*G01N 33/92* (2006.01)

(52) U.S. Cl.
CPC .......... *G01N 33/92* (2013.01); *G01N 2800/323* (2013.01); *G01N 2800/324* (2013.01); *G01N 2800/325* (2013.01)

(58) Field of Classification Search
None
See application file for complete search history.

(56) References Cited

U.S. PATENT DOCUMENTS

| | | | |
|---|---|---|---|
| 2002/0164662 A1 | 11/2002 | Hazen et al. | |
| 2004/0143461 A1 | 7/2004 | Watkins | |
| 2008/0003684 A1 | 1/2008 | Laaksonen et al. | |
| 2009/0029473 A1 | 1/2009 | Han | |
| 2009/0197242 A1 | 8/2009 | Kaddurah-Daouk et al. | |
| 2010/0278907 A1* | 11/2010 | Bieberich ..................... | 424/450 |
| 2013/0023054 A1* | 1/2013 | Meikle et al. ................... | 436/71 |

FOREIGN PATENT DOCUMENTS

| CN | 101132789 A | 2/2008 |
|---|---|---|
| CN | 101522910 | 9/2009 |
| EP | 1726962 A1 | 11/2006 |
| JP | 2007263979 A | 10/2007 |
| JP | 2008516595 A | 5/2008 |
| JP | 2009540314 A | 11/2009 |
| WO | 98/57179 A1 | 12/1998 |
| WO | 01/65257 A2 | 9/2001 |
| WO | 2004/085610 | 10/2004 |
| WO | 2005/063275 A1 | 7/2005 |
| WO | 2006/092025 A1 | 4/2006 |
| WO | 2006040409 A1 | 4/2006 |
| WO | 2007/127192 | 11/2007 |
| WO | 2007/144467 | 12/2007 |
| WO | 2008/118413 A2 | 10/2008 |
| WO | 2011/063470 A1 | 6/2011 |
| WO | 2011/138419 A1 | 11/2011 |

OTHER PUBLICATIONS

Floridi et al. (Sphingolipid Club 2004 3rd meeting (Firenze); Abstract).*
Merrill et al. (Methods 2005 vol. 36, p. 207-224).*
Valsecchi et al. (J. Lipid Res 2007 vol. 48, p. 417-424).*
Communication dated Aug. 25, 2011 from European Patent Application No. 10 162 066.4, pp. 1-4.
Communication dated Jun. 1, 2012 from European Patent Application No. 10 162 066.4, pp. 1-6.
Communication dated Dec. 6, 2012 from European Patent Application No. 10 162 066.4, pp. 1-6.
Holewijn, S. et al. Apolipoprotein B, non-HDL cholesterol and LD cholesterol for identifying individuals at increased cardiovascular risk. Journal of Internal Medicine, 2010, pp. 547-577.
Ramjee, Vimal et al. Non-High-Density Lipoprotein Cholesterol Versus Apolipoprotein B in Cardiovascular Risk Stratification, Do the Math. Journal of American College of Cardiology, vol. 58, Nov. 5, 2011, pp. 457-463.
Sniderman, Allan D. et al. A Meta-Analysis of Low-Density Lipoprotein Cholesterol, Non-High-Density Lipoprotein Cholesterol and Apolipoprotein B as Markers of Cardiovascular Risk. Circ. Cardiovasc. Qual Outcomes, May 2011, pp. 337-345.
European Search Report dated Aug. 5, 2010 from European Patent Application No. 10 162 066.4, pp. 1-12.
Pocock, Stuart J. et al. A score for predicting risk of death from cardiovascular disease in adults with raised blood pressure, based on individual patient data from randomised controlled trials BMJ, Jul. 14, 2001, vol. 323, pp. 75-81.
D'Agostino, Ralph B. et al. Primary and subsequent coronary risk appraisal: New results from the Framingham Study. American Heart Journal, 2000, vol. 139, No. 2, Part 1, pp. 272-281.

(Continued)

*Primary Examiner* — Jacob Cheu
(74) *Attorney, Agent, or Firm* — MH2 Technology Law Group, LLP

(57) ABSTRACT

The present invention inter alia provides a method, and use thereof, of diagnosing and/or predicting atherosclerosis or CVD by detecting the lipid concentrations or lipid ratios of a biological sample and comparing it to a control and has identified specific lipid markers that are more specific and sensitive in detecting and predicting atherosclerosis and CVD than currently utilized clinical markers. Also provided is an antibody towards said lipids, and the use thereof for predicting, diagnosing, preventing and/or treating atherosclerosis or CVD. The invention additionally relates to kits comprising lipids and/or an antibody thereto, for use in the prediction and/or diagnosis of atherosclerosis or CVD.

15 Claims, 3 Drawing Sheets

(56) References Cited

OTHER PUBLICATIONS

Menotti, Alessandro et al. Comparison of multivariate predictive power of major risk factors for coronary heart diseases in different countries: results from eight nations of the Seven Countries Study, 25-year follow up. Journal of Cardiovascular Risk, Feb. 1996, vol. 3, No. 1, pp. 69-75.
Cheng, Jin M. et al. In vivo detection of high-risk coronary plaques by radiofrequency intravascular ultrasound and cardiovascular outcomes: results of the ATHEROREMC-IVUS study. European Heart Journal, Nov. 19, 2013, pp. 1-9.
Coppola, W.G.T. et al. Scoring system to identify men at high risk of stroke: a strategy for general practice. British Journal of General Practice, Apr. 1995, pp. 185-189.
Allonen, Jaakko et al. Mortality Rate Increases Steeply With Nonadherence to Statin Therapy in Patients With Acute Coronary Syndrome. Clin. Cardiol., 2012, vol. 35, No. 11, pp. 22-27.
Hu, Chunxiu et al., Analytical strategies in lipidomics and applications in disease biomarker discovery, Journal of Chromatography B, 877 (2009) 2836-2846, XP026422757.
Stahlman, Marcus et al., High-throughput shotgun lipidomics by quadrupole time-of-flight mass spectrometry, Jounral of Chromatography B, 877 (2009) 2664-2672, XP026422742.
Kaddurah-Daouk, Rima et al., Lipidomic analysis of variation in response to simvastatin in the Cholestrol and Pharamcogenetics Study, Metabolomics, (2010) 6:191-201, XP002592438.
Laaksonen, R., Lipidomics as a tool for atherosclerosis research, New Biotechnology, vol. 27, Apr. 1, 2010, S18-S19, XP026965681.
Ekroos, Kim et al., Lipidomics: A Tool for Studies of Atherosclerosis, Current Atherosclerosis Reports, Jul. 2010, vol. 12, No. 4, pp. 273-281, XP008124463.
Janis, Minna T, et al., Metabolomic strategies to identify tissue-specific effects of cardiovascular drugs, Expert Opinion on Drug Metabolism & Toxicology, Jun. 2008, vol. 4, No. 6, pp. 665-680, XP008124464.
Waterman, Claire L. et al., Metabolomic strategies to study lipotoxicity in cardiovascular disease, Biochimica and Biophysica Acta., vol. 1801, No. 3, Mar. 1, 2010, pp. 230-234, XP026904840.
International Search Report dated Jul. 15, 2011 issued from the European Patent Office for International Application No. PCT/EP2011/057254.
Christin Stegemann et al., "Comparative Lipidomics Profiling of Human Atherosclerotic Plaques", Circulation Cardiovascular Genetics, vol. 4, 2011, pp. 232-242.
Menard M. Gertler et al., "The Interrelationships of Serum Cholesterol, Cholesterol Esters and Phospholipids in Health and in Coronary Artery Disease", Circulation, vol. 11, 1950, pp. 205-214.
Peter J. Meikle et al., "Plasma Lipidomic Analysis of Stable and Unstable Coronary Artery Disease", Arteriosclerosis, Thrombosis, and Vascular Biology, vol. 31, 2011, pp. 2723-2732.
Masahiro Sugano et al., "Effects of diltiazem on suppression and regression of experimental atherosclerosis", Br. J. exp. Path., vol. 69, 1988, pp. 515-523.
Peter John Meikle et al., "Diagnostic and Prognostic Assay", U.S. Appl. No. 61/264,767, filed Nov. 27, 2009, pp. 1-121.
Wikipedia Entry, "Cholesterinester", http://de.wikipedia.org/w/index.php?title=Cholesterinester&oldid=124171453, Version of Oct. 28, 2009, pp. 1-4 (Includes English Language Translation).
Subroto B. Chatterjee et al., "Accumulation of glycosphingolipids in human atherosclerotic plaque and unaffected aorta tissues", Glycobiology, vol. 7, No. 1, 1997, pp. 57-65.
Christin Stegemann et al., "Lipidomics Profiling and Risks of Cardiovascular Disease in the Prospective Population-Based Bruneck Study", Circulation, vol. 129, 2014, pp. 1821-1831.
Ikuyo Ichi et al., "Association of Ceramides in Human Plasma with Risk Factors of Atherosclerosis", vol. 41, No. 9, 2006, pp. 859-863.
Dieter M. Kramsch et al., "The Protein and Lipid Composition of Arterial Elastin and Its Relationship to Lipid Accumulation in the Atherosclerotic Plaque", The Journal of Clinical Investigation, vol. 50, 1971, pp. 1666-1677.

G. A. Gribanov et al., "Blood Lipid Changes in Hypoxic Rats", Space Biology and Aerospace Medicine (Russian Journal), No. 6, 1978, pp. 67-71.
A. Beresewicz et al., "Accumulation of Specific Ceramides in Ischemic/Reperfused Rat Heart; Effect of Ischemic Preconditioning", Journal of Physiology and Pharmacology, vol. 53, No. 3, 2002, pp. 371-382.
Yu. N. Borinsky et al., "The Lipid Spectrum of Various Zones of Infarction-Damaged Myocardium as a Reflection of Its Metabolic and Functional Activity in the Period Preceding Fatal Outcome of the Disease", Voprosy Medicinskoj Himii (Russian), vol. 39, No. 6, pp. 20-22, 1993.
T. A. Miettinen et al., "Fatty-acid composition of serum lipids predicts myocardial infarction", British Medical Journal, vol. 285, 1982, pp. 993-996.
Joseph H. Rapp et al., "Lipids of human atherosclerotic plaques and xanthomas: clues to the mechanism of plaque progression", Journal of Lipid Research, vol. 24, 1983, pp. 1329-1335.
J. McLaurin et al., "Reactivity of two anti-galactosyl ceramide antibodies towards myelin basic protein", Journal of Neurological Sciences, vol. 108, 1992, pp. 73-79.
Notice of Opposition dated Oct. 8, 2014 filed against European Patent No. EP 2385374 B1, pp. 1-21.
Maria Lankinen et al., "Fatty Fish Intake Decreases Lipids Related to Inflammation and Insulin Signaling—A Lipidomics Approach", PLoS ONE, vol. 4, Issue 4, Apr. 2009, pp. 1-9.
Non-Final Office Action dated Aug. 11, 2014, U.S. Appl. No. 13/805,319, filed Feb. 13, 2013, pp. 1-57.
Fahumiya Samad et al., "Altered Adipose and Plasma Sphingolipid Metabolism in Obesity: A Potential Mechanism for Cardiovascular and Metabolic Risk", Diabetes, vol. 55, Sep. 2006, pp. 2579-2587.
Richard G. Melvin et al., "Torpor induction in mammals: recent discoveries fueling new ideas", Trends in Endocrinology and Metabolism, vol. 20, No. 10, 2009, pp. 490-498.
Mohammad Iqbal Hossain Bhuiyan et al., "Involvement of Ceramide in Ischemic Tolerance Induced by Preconditioning with Sublethal Oxygen-Glucose Deprivation in Primary Cultured Cortical Neurons in Rats", Biological and Pharmaceutical Bulletin, vol. 33., No. 1, Jan. 2010, pp. 11-17.
Guang Yang et al., "Central role of ceramide biosynthesis in body weight regulation, energy metabolism, and the metabolic syndrome", AJP—Endocrinology and Metabolism, vol. 297, Jul. 2009, pp. E211-E224.
Hye Hyun Yoo et al., "Liquid chromatography-tandem mass spectrometric determination of ceramides and related lipid species in cellular extracts", Journal of Chromatography B, vol. 843, 2006, pp. 327-333.
Alfred H. Merril, Jr. et al., "Sphingolipidomics: High-throughput, structure-specific, and quantitative analysis of sphingolipids by liquid chromatography tandem mass spectrometry", Methods, vol. 36, 2005, pp. 207-224.
Ikuyo Ichi et al., "Effect of dietary cholesterol and high fat ceramide concentration in rat tissues", Nutrition, vol. 23, 2007, pp. 570-574.
Lama Noureddine et al., "Modulation of total ceramide and constituent ceramide species in the acutely and chronically hypoxic mouse heart at different ages", Prostaglandis and Other Lipid Mediators, vol. 86, 2008, pp. 49-55.
Subroto Chatterjee et al., "Increased urinary excretion of glycosphingolipids in familial hypercholesterolemia", Journal of Lipid Research, vol. 23, 1982, pp. 513-522.
Wenjing Zheng et al., "Ceramides and other bioactive sphingolipid backbones in health and disease: Lipidomic analysis, metabolism and roles in membrane structure, dynamics, signaling and autophagy", Biochimica et Biophysica Acta, vol. 1758, 2006, pp. 1864-1884.
Jacek Bielawski et al., "Simultaneous quantitative analysis of bioactive sphingolipids by high-performance liquid chromatography-tandem mass spectrometry", Methods, vol. 39, 2006, pp. 82-91.
International Search Report and Written Opinion dated May 11, 2012, International Application No. PCT/EP2011/060253 filed Jun. 20, 2011, pp. 1-32.
Canadian Office Action dated Jun. 16, 2014, Canadian Application No. 2,798,238, pp. 1-4.

(56) References Cited

OTHER PUBLICATIONS

Canadian Office Action dated Jun. 16, 2014, Canadian Application No. 2,801,459, pp. 1-4.
Japanese Office Action dated Jan. 7, 2015, Japanese Patent Application No. 2013-515841, pp. 1-4.
Japanese Office Action dated Jan. 21, 2015 for Japanese Patent Application No. 2013-508512, pp. 1-6.
Chinese Second Office Action dated Jan. 20, 2015 for Chinese Patent Application No. 201180032921.0, pp. 1-11.
Chinese Search Report dated Jan. 20, 2015, Chinese Patent Application No. 201180032921.0, pp. 1-5.
Zhan-qun Pan et al. "Treatment for High-Density Lipoprotein Deficiency", Department of Cardiology, The Second Affliated Hospital of Nanchang University, Adv Cardiovasc D, vol. 30, No. 3, May 2009, pp. 521-525 (English Translation of Abstract).
Yongzong Yang, Book Titled: Basis and clinic for atherosclerotic cardio-cerebrovascular diseases, Apr. 30, 2004, pp. 277-281.
Lijun Chen, Book Titled: Metabolism (3), Lipid Biochemistry, Nov. 30, 1988, pp. 93-94.

\* cited by examiner

LIPIDOMIC BIOMARKERS FOR ATHEROSCLEROSIS AND CARDIOVASCULAR DISEASE

CROSS-REFERENCE TO RELATED APPLICATIONS

This application is a U.S. National Stage application of PCT/EP2011/057254 filed 5 May 2011, which claims priority to European patent application 10162066.4 filed 5 May 2010 and U.S. Provisional Patent Application 61/331,463 filed 5 May 2010, the entire disclosures of which are hereby incorporated herein by reference in their entireties.

FIELD OF THE INVENTION

This invention relates to methods and uses involving lipid levels to diagnose, predict, prevent and/or treat atherosclerosis or cardiovascular disease (CVD) and their fatal and non-fatal complications including e.g. acute myocardial infarction and death. The methods include analyzing lipid levels of a biological sample, and comparing it to a control.

BACKGROUND OF THE INVENTION

Worldwide, cardiovascular diseases are among the leading causes of mortality and morbidity with ever-increasing prevalence. Early targeted initiation of preventive measures would be of great benefit and can provide a major opportunity in reducing mortality and morbidity. To this end, accurate identification of individuals who are still asymptomatic but at elevated risk is essential. However, traditional risk assessment fails to recognize a substantial proportion of patients at high risk while a large proportion of individuals are classified as having intermediate risk, leaving patient management uncertain. Additional strategies to further refine risk assessment are therefore highly needed. To this end, the inventors have evaluated the role of novel lipidomic biomarkers as diagnostic tool for atherosclerosis. These new biomarkers can be used to identify an individual at elevated risk for CVD events such as angina pectoris, myocardial infarction, stroke and cardiovascular death.

Plasma or serum total cholesterol, LDL-cholesterol or HDL-cholesterol concentrations have been used as gold standard biomarkers for CVD/CAD risk prediction. However, a number of coronary artery disease (CAD) or acute myocardial infarction (AMI) patients have LDL-C levels within the recommended range suggesting the need for additional diagnostic measures of the residual risk. It is evident from earlier large scale population studies that these measurements associate with the CAD risk and CAD endpoints such as AMI or cardiovascular death. Therefore, preventive treatment strategies have so far been addressed to lower LDL-C concentrations (mainly by statin treatment) and more recently also attempts to raise HDL-C have been made (e.g. by CETP-inhibitors). On the other hand, it has also been observed that one half of the AMI patients actually do have normal LDL cholesterol levels and that there is a substantial residual risk in statin treated patients despite a LDL-C lowering. Furthermore, recent publications have demonstrated that plasma levels of apolipoprotein B (apoB), the main surface protein on LDL particles, and LDL-C, the amount of cholesterol in those particles, are correlated and, considered separately, as positive risk factors. Plasma levels of apolipoprotein $A_1$, the main surface protein on HDL particles, and HDL-C, the amount of cholesterol in those particles, are also correlated with each other and, considered separately, as negative risk factors. Importantly, for a given usual apoB, lower LDL-C has been observed to associate with a higher risk of AMI supporting the view that, on average, LDL particles with low cholesterol content per particle (small, dense LDL particles) are particularly hazardous. Thus, it seems possible that LDL-C associates directly with the more dangerous molecules carried by LDL-particle and that LDL-C is only an indirect measurement of the risk. Therefore, it is of importance to search for molecules e.g. lipid species that play an active role in the CAD development.

Lipid metabolite imbalance is a probable cause of dyslipidemia and the ensuing atherosclerosis manifested in its gravest form as the vulnerable atherosclerotic plaque. Atherosclerotic plaques are complex molecular formations that contain numerous lipids. However, there are other factors than lipid rich plaques or LDL cholesterol that make lipids an attractive group of molecules for CVD studies. Lipids are tightly regulated which makes Lipidomic data robust and informative on the current state of the studied organism. Also, lipids are one of the culmination points of a biological system, more the true outcome than the predictor. Combining Lipidomic data with appropriate biobanked clinical material presents a good opportunity for biomarker discovery. Moreover, lipidomics can be used as a gauge of efficacy and safety in drug development and evolving theragnostics. Lipidomic biomarkers are prime candidates for true companion diagnostics in the CVD area and present many opportunities for improved translational medicine as well.

The plaque building blocks and lipoprotein components that are thought to traffic the lipids to the site of lesion formation can now be resolved with Lipidomic studies correlating lipid structure and composition to function and thereby disease pathogenesis. While the number of lipid mediators in the human body is overwhelming their identification and quantification is facilitated by the advances in mass spectrometry and lipid biochemistry, which today enable the simultaneous high throughput identification and quantification of hundreds of molecular lipid species in several lipid classes (Ejsing C S, et al: *Global analysis of the yeast lipidome by quantitative shotgun mass spectrometry. Proc Natl Acad Sci USA* 2009, 106:2136-2141; Stahlman M, et al: *High-throughput shotgun lipidomics by quadrupole time-of-flight mass spectrometry. J Chromatogr B Analyt Technol Biomed Life Sci* 2009 Hiukka A, et al: *ApoCIII-enriched LDL in type 2 diabetes displays altered lipid composition, increased susceptibility for sphingomyelinase, and increased binding to biglycan. Diabetes* 2009, 58:2018-2026; Linden D, et al: *Liver-directed overexpression of mitochondrial glycerol*-3-*phosphate acyltransferase results in hepatic steatosis, increased triacylglycerol secretion and reduced fatty acid oxidation. FASEB J*2006, 20:434-443.) collectively referred to as the lipidome. Lipidomic studies identify lipid cellular distribution and describe their biochemical mechanisms, interactions and dynamics. Importantly, lipidomics quantifies the exact chemical composition of lipidomes (Han X, Gross R W: *Global analyses of cellular lipidomes directly from crude extracts of biological samples by ESI mass spectrometry: a bridge to lipidomics. J Lipid Res* 2003, 44:1071-1079).

Due to both high sensitivity and selectivity of lipidomics, even the smallest sample amounts can be analyzed today. The bulk of the lipid data in the art today presents lipids in a sum composition format, i.e. phosphatidylcholine (PC) 34:1 (Brugger B, et al: *Quantitative analysis of biological membrane lipids at the low picomole level by nano-electrospray ionization tandem mass spectrometry. Proc Natl Acad Sci USA* 1997, 94:2339-2344) where the molecular lipid and the attached fatty acid tails remain unidentified. The identification of molecular lipid species, e.g., PC 16:0/18:1 (Ekroos K, et al: *Charting molecular composition of phosphatidylcholines by fatty acid scanning and ion trap MS3 fragmentation.* J Lipid Res 2003, 44:2181-2192) is the main feature of advanced lipidomics, which delivers highly resolved molecular lipid species rather than summed fatty acid information. For example, the information of the type of fatty acids and their positions of attachment to the glycerol backbone making up the particular PC molecule is revealed. There are conventional techniques such as thin-layer chromatography combined with gas chromatography but they not only require considerably larger sample amounts and laborious sample preparation, but they do not deliver the molecular lipid species. Despite multiple mass spectrometry techniques capable of characterizing lipid entities, most of them are still unable to deliver reliable high-quality quantitative data in terms of absolute or close-to absolute concentrations. In the context of the present invention, electrospray ionization mass spectrometry based lipidomics is the preferred technology and can utilize both shotgun and targeted lipidomics for exhaustive deciphering and precise quantification of molecular lipidomes. The superior quality and specificity of shotgun and targeted lipidomics will meet stringent regulatory standards, such as good laboratory practice guidelines (GLP) when set-up in the proper environment. Using these technologies quantification of up to two thousand molecular lipids is possible even in a high throughput format.

Lipidomics is a tool for differentiating patients based on their molecular lipid profiles. Personalized medicine and diagnostics enabled by lipidomics will facilitate the mission of the right individual receiving the right drug at the right time and dose. Several works employing analytes consisting of lipids, proteins and hydrophilic molecules among many others have been conducted to meet the needs of personalized medicine.

Recently, non-hypothesis-driven metabolomic screenings have been used to identify novel CVD biomarkers.

For example, WO2004/038381 discloses a method for metabolomically facilitating the diagnosis of a disease state of a subject, or for predicting whether a subject is predisposed to having a disease state wherein the small molecule profile from a subject is obtained and compared to a standard small molecule profile.

Additionally, Zhang et al. utilized an ultra fast liquid chromatography coupled with IT-TOF mass spectrometry (UFLC/MS-IT-TOF) to study plasma and urine metabolic profiles of atherosclerosis rats (Zhang F, et al: *Metabonomics study of atherosclerosis rats by ultra fast liquid chromatography coupled with ion trap-time offlight mass spectrometry.* Talanta 2009, 79:836-844). Their observations suggest that abnormal metabolism of phenylalanine, tryptophan, bile acids, and amino acids might be related to atherosclerosis development. Furthermore, Zha et al. identified a metabolic fingerprint of twenty-one compounds in hamsters that could be a potential marker for the development of atherosclerosis (Zha W, et al: *Metabonomic characterization of early atherosclerosis in hamsters with induced cholesterol. Biomarkers* 2009, 14:372-380).

More specifically, US2008/0085939 relates to the use of specific sphingolipids, especially phytosphingosine, sphingosine and/or sphinganine for prevention and/or treating inflammatory processes associated with atherosclerosis. This is based on the observation that sphingolipids have an anti-inflammatory effect. Similarly, WO2008/148857 discloses a method to assess the risk of cardiovascular disease in a patient (including atherosclerosis) by isolating the HDL fraction and sub-fraction from a blood sample of the patient. The components of the HDL fraction or sub-fraction to be measured were Sphingosine-1-Phosphate (S1P), sphingomyelin (SM) and Apolipoprotein A-I (apoA-1).

WO2008/11943 further discloses markers for detecting coronary artery disease that can indicate a patient at risk of having or developing coronary artery disease. These include 15 "first-choice" molecules which were: C18:3 Cholesterol ester, C32:1 Phosphatidylcholine, Alanine, Lipid (mainly VLDL), Lysine, Hexadecanoic acid, C36:2 Phosphatidylcholine, Formate, C32:2 Phosphatidylcholine, C18:2 (Linoleic Acid), Cholesterol, C18:2 Lyso-phosphatidylcholine, C36:3 Phosphatidylcholine, C34:4 Phosphatidylcholine and C34:3 Phosphatidylcholine.

Furthermore, US2007/0099242 describes a method to determine if a subject is at risk to develop, or is suffering from cardiovascular disease. The method involves determining a change in the amount of a biomarker in the biological sample or HDL sub-fraction thereof, compared to a control sample, wherein the biomarker is at least one of Apolipoprotein C-IV ("ApoC-IV"), Paraoxonase 1 ("PON-1"), Complement Factor 3 ("C3"), Apolipoprotein A-IV ("ApoA-IV"), Apolipoprotein E ("ApoE"), Apolipoprotein LI ("ApoL1"), Complement Factor C4 ("C4"), Complement Factor C4B1 ("C4B1"), Histone H2A, Apolipoprotein C-II ("ApoC-II"), Apolipoprotein M ("ApoM"), Vitronectin, Haptoglobin-related Protein and Clusterin. The document also discloses a method for detecting the presence of one or more atherosclerotic lesions wherein a change in the amount of a biomarker in the biological sample or HDL sub-fraction thereof is detected, compared to a control sample and wherein the biomarker is selected from PON-1, C3, C4, ApoE, ApoM and C4B1. All biomarkers mentioned in this document are protein or lipoprotein biomarkers.

From previous work it cannot be extrapolated that lipid analysis will yield by default a CVD biomarker. Earlier analytical attempts to find specific biomarkers, which have also included some lipid analytes did not generate novel lipid biomarker findings of clinical value. The present invention identifies CVD biomarkers by absolute, or close to absolute, quantification of defined molecular lipid species instead of profiling multiple analytes. Importantly, while many of the existing biomarker candidates are composite fingerprints of multiple factors, the lipidomics approach herein shows value already at a level of single species or ratios thereof. The present invention herein is the first one where the lipid biomarker concentrations have been measured and quantified, therefore adding more accuracy to the findings and enabling accurate usage of the lipid based biomarker. The lipid biomarkers herein have not been linked to CVD risk predicton in the above publications. Another layer of accuracy was reached through a careful patient selection as it is important to take into account those factors which may affect the measured lipid concentrations. Thus, we excluded statin users, matched cases and controls for apoB levels (major lipid carrier particle in blood) and included only males. Unlike the previous efforts described above we used specific targeted platforms on a singular technology set-up to analyze lipid species in particular.

The technology and the way it was applied in the context of the inventive teaching presented herein is set apart from similar efforts in the field inter alia due to the following criteria. In sample preparation, samples are strictly controlled and treated identically to avoid potential artifacts that could arise from improper handling. In connection with the present invention, samples were carefully thawed slowly on ice and directly thereafter subjected to a custom made automated lipid extraction which possesses currently the highest precision in liquid handling, therefore minimizing potential errors. Furthermore, sample freeze-thaw cycles were strictly controlled since this can dramatically affect the lipid stabilities. The automated lipid extraction is based on the method by Folch and colleagues (Folch J, et al: *A simple method for the isolation and purification of total lipids from animal tissues. J Biol Chem* 1957, 226(1):497-509) which uses chloroform and methanol. This method is preferred when a wide range, from polar to non-polar, of lipid classes are to be extracted with optimal recoveries thus preventing the loss of lipid species. Lipid class specific non-endogenous lipids, when applicable, were used as internal standards to gain highest precision in identification (minimizing false positives) and quantification of monitored molecular lipid species. In this way absolute or semi-absolute amounts of endogenous molecular lipids were determined with the highest precision that can be achieved with today's technologies. The endogenous lipids and respective standards were monitored at the molecular lipid level. In this way, not only false positive identifications were minimized, but molecular lipids could be precisely determined and quantified. Analysis quality was strictly controlled using a novel quality control system. This was mainly controlled by multiple internal standards (IS), external standards (ES), IS/ES ratios, and instrument control samples. By stringently controlling these components, technical and biological outliers were readily identified and rejected from further analysis. To obtain best precision in sensitivity, selectivity and quantification for each molecular lipid different targeted platforms were used. Some lipids are best analyzed using high performance liquid chromatography (HPLC) or ultra high performance liquid chromatography (UHPLC) combined with mass spectrometry based multiple reaction monitoring (MRM) whereas others are best analyzed by direct infusion in combination with mass spectrometry based precursor ion scanning and neutral loss scanning techniques.

SUMMARY OF THE INVENTION

The present invention provides novel lipidomic markers for predicting the development of atherosclerosis or cardiovascular disease (CVD). Specifically, it has been found that the lipid molecules, lipid-lipid ratios and lipid-clinical concentration ratios provided herein, when displaying an increased or decreased level—as the case may be—in samples from atherosclerotic or CVD patients, are useful lipidomic markers for the methods and uses in accordance with the present invention. These sensitive and specific markers were specifically tested to display superior diagnostic and prognostic value compared to the current clinically-used markers predictive of atherosclerosis and CVD. The present invention therefore represents a significant advantage to other markers which are currently used to diagnose and/or predict atherosclerosis or CVD, which markers include LDL-C, total plasma/serum cholesterol and Apolipoprotein B and A1. Thus, the lipidomic markers provided herein allow better diagnosis of or assessment of the risk to develop atherosclerosis or CVD and/or major CVD complications such as AMI or CVD death.

In accordance with the present invention, methods are inter alia disclosed herein for determining the risk of a patient to develop CVD, determining early warning signs of CVD in said patient, determining or predicting the occurrence of atherosclerosis in a patient; and/or predicting and/or diagnosing CVD and/or CVD complications, including death, myocardial infarction (MI), angina pectoris, transischemic attack (TIA) and stroke.

Methods according to the invention typically comprise the steps of: a) providing a biological sample from a subject prior to or during atherosclerosis; b) determining a lipid concentration, lipid-lipid ratio, or lipid-clinical concentration ratio or (a) corresponding profile(s) from said sample (i.e., determining information on a lipidomic marker in accordance with the invention); and c) comparing said determined lipid concentration, lipid-lipid ratio, or lipid-clinical concentration ratio or said corresponding profile(s) to the corresponding lipid concentration, lipid-lipid ratio, or lipid-clinical concentration ratio or the corresponding profile(s) in a control.

The control may be a sample from a healthy individual. It may also be a sample that represents a combination of samples from a generalized population of healthy individuals. Alternatively, the control may be a set of data concerning a lipidomic marker in accordance with the present invention, e.g., information on the concentration of (a) lipid(s), lipid-lipid ratio(s), or lipid-clinical concentration ratio(s) in accordance with the present invention in a sample when taken from a healthy individual, or in a combination of samples when taken from a generalized population of healthy individuals. Said information, and thus the corresponding set of data, may have been previously determined, calculated or extrapolated, or may have yet to be determined, calculated or extrapolated, or may also be taken from the literature.

As mentioned above, the lipidomic marker to be compared between the subject sample and the control (or control sample) may be one or more of the lipid concentration(s), lipid-lipid ratio(s), or lipid-clinical concentration ratio(s) or combinations thereof, i.e., the corresponding profile(s), as described and claimed herein. In this regard, the control or control sample allows establishment of the lipidomic marker baseline or starting point.

In connection with all aspects and embodiments of the invention described and claimed herein, the determination of the lipid concentration(s), the lipid-lipid ratio(s) or the lipid-clinical concentration ratio(s) is typically performed using an assay. Collecting information on a lipidomic marker (i.e., the concentration(s) of (a) lipid(s), lipid-lipid ratio(s), or lipid-clinical concentration ratio(s) or combinations thereof, i.e., corresponding profile(s)) from the sample of a patient and, where appropriate, a corresponding control sample, can be performed with various chemical and high-resolution analytical techniques. Suitable analytical techniques include, but are not limited to, mass spectrometry and nuclear resonance spectroscopy. Any high-resolution technique capable of resolving individual lipids or lipid classes and providing structural information of the same can be used to collect the information on the lipidomic marker in question, e.g., lipid profile from the biological sample. Collecting the information on the lipidomic marker with mass spectrometry (MS) is one of the preferred embodiments of the current invention. The MS instrument can be coupled to a direct sample infusion method, such as a robotic nanoflow ion source device, or to a high performance separation method such as high performance liquid chromatography (HPLC) or ultra performance liquid chromatography (HPLC).

Again in accordance with all aspects and embodiments described and claimed herein, both the sample from the subject and the control sample is preferably a blood sample, more preferably a blood plasma sample, or also preferably a blood serum sample. It may also be a fraction of blood, blood plasma or blood serum, e.g., a lipoprotein fraction. A blood sample can be prepared and plasma or serum, or fractions thereof, can be separated therefrom with techniques well known to the person skilled in the art. Alternatively, both the sample from the subject and the control sample may also be a tissue sample, e.g., artery tissue, such as carotid artery tissue, or artery plaque material, such as carotid artery plaque material.

The lipidomic markers of the present invention allow for earlier prediction of atherosclerosis or CVD or fatal or nonfatal CVD complications. This will facilitate earlier intervention, less symptom development and suffering and decreased morbidity associated with CVD. Thus, the lipidomic markers described and claimed herein allow for individual tailoring of drug intervention for patients suffering from or being at risk to develop atherosclerosis or CVD or their complications.

In other words, the present invention discloses diagnostic and/or predictive lipid markers and lipid-lipid or lipid-clinical concentration ratios for use in diagnosing or predicting atherosclerosis or CVD or their complication such as AMI or CVD death. The invention uses the measurement of lipid concentrations, lipid-lipid and/or lipid-clinical concentration ratios to determine the risk of said subject to develop CVD; determine early warning signs of CVD in said subject; determine or predict atherosclerosis in a subject; and/or predict and/or diagnose CVD. The subject may have previously suffered from a cardiovascular disease event such as angina pectoris, myocardial infarction, stroke and cardiovascular death. The CVD may or may not be a result of atherosclerosis.

Accordingly, in one aspect of the invention, a method is provided for determining whether a subject is at risk to develop, or is suffering from atherosclerosis or cardiovascular disease (CVD) and/or one or more of their complications, such as AMI or CVD death, said method comprising determining in a sample from said subject the concentration(s) of one or more lipid(s), wherein (an) increased or decreased concentration(s) in said sample, when compared to a control sample, is (are) indicative of said subject suffering from or having an increased risk of developing atherosclerosis or CVD and/or one or more of their complications, such as AMI or CVD death, wherein the one or more lipid(s) whose increase in concentration is (are) compared to the control is (are) selected from:

Cer(d18:0/22:0), Cer(d18:0/24:0), Cer(d18:0/24:1), Cer(d18:1/16:0), Cer(d18:1/18:0), Cer(d18:1/20:0), Cer(d18:1/24:1), GlcCer(d18:1/16:0), GlcCer(d18:1/18:0), LacCer(d18:1/18:0), LacCer(d18:1/20:0), LacCer(d18:1/22:0), LacCer(d18:1/24:1), Total LacCer, LacCer(d18:1/24:0), Total Cer, GlcCer(d18:1/24:0), Total GlcCer and LacCer (d18:1/16:0);

and wherein the one or more lipid(s) whose decrease(s) in concentration is (are) compared to the control is (are) selected from:

CE 14:0, CE 16:0, CE 17:1, CE 20:3, PC 35:3 (PC O-34:3), Cer(d18:0/24:0), GD3-d18:1/16:0, PC 16:0/16:1, PC 37:5 (PC O-38:5), SM (d18:1/16:1) (d18:1/15:2-OH), SM (d18:1/18:1), SM (d18:1/23:1) (d18:1/22:2-OH), Total CE, Total GD3, Total PC 0, Total PC, PC 16:0/20:4, CE 18:0, Cer(d18:1/26:1), CE 15:0, SM (d18:1/15:0)(d18:1/14:1-OH), GM3-d18:1/18:0, PC 37:5 (PC O-36:5), GM3-d18:1/21:0, PC 16:0/18:2, Total PI, SM (d18:1/17:0) (d18:1/16:1-OH), Cer(d18:1/26:0), PC 18:0/20:5, PI 38:3, PC 40:5, GM2-d18:1/18:0, Total GM2, GD1-d18:1/16:0, PC 16:0/20:5, PC 16:0/22:5, PC 18:0/20:3, PC 16:0/22:6, PI 38:4, and PC 16:0/20:4 (see Tables 2, 5, 8 and 11).

In a preferred embodiment, the one or more lipid(s) whose increase(s) in concentration is (are) compared to the control is (are) selected from:

Cer(d18:0/22:0), Cer(d18:0/24:0), Cer(d18:0/24:1), Cer(d18:1/16:0), Cer(d18:1/18:0), Cer(d18:1/24:1), GlcCer(d18:1/16:0), GlcCer(d18:1/18:0), LacCer(d18:1/18:0), LacCer(d18:1/20:0), LacCer(d18:1/22:0), and LacCer(d18:1/24:1).

In another preferred embodiment, the one or more lipid(s) whose decrease(s) in concentration is (are) compared to the control is (are) selected from:

CE 16:0, CE 17:1, PC 35:3 (PC O-34:3), CE 14:0, CE 20:3, Total CE, Cer(d18:0/24:0), GD3-d18:1/16:0, PC 16:0/16:1, PC 37:5 (PC O-38:5), SM (d18:1/18:1), SM (d18:1/23:1) (d18:1/22:2-OH), SM (d18:1/16:1) (d18:1/15:2-OH), Total GD3, and Total PC (see Tables 14 and 15).

In a particularly preferred embodiment, the one or more lipid(s) whose increase(s) in concentration is (are) compared to the control is (are) selected from:

Cer(d18:1/16:0), LacCer(d18:1/22:0), and LacCer(d18:1/24:1).

In another particularly preferred embodiment, the one or more lipid(s) whose decrease(s) in concentration is (are) compared to the control is (are) selected from:

CE 14:0 and CE 20:3 (see Table 20).

In an alternative embodiment the present invention relates to a method for determining whether a subject is at risk to develop, or is suffering from atherosclerosis or cardiovascular disease (CVD) and/or one or more of their complications such as AMI or CVD death, comprising determining in a sample from said subject one or more lipid-lipid ratio(s), wherein (an) increased or decreased lipid-lipid ratio(s) in said sample, when compared to a control sample, is (are) indicative of said subject suffering from or having an increased risk of developing atherosclerosis or CVD and/or one or more of their complications, such as AMI or CVD death, wherein the one or more lipid-lipid ratio(s) whose increase(s) is (are) compared to the control is (are) selected from:

CE 19:1/LPC 20:4, Cer(d18:1/16:0)/LPC 16:0, Cer(d18:1/16:0)/LPC 18:1, Cer(d18:1/16:0)/LPC 18:2, Cer(d18:1/16:0)/PC 16:0/20:4, Cer(d18:1/16:0)/PC 18:1/18:2, Cer(d18:1/16:0)/PC 33:2 (PC O-34:2), Cer(d18:1/16:0)/PC 35:3 (PC 0-36:3), Cer(d18:1/16:0)/PC 35:4 (PC O-36:4), Cer(d18:1/16:0)/PC 36:3, Cer(d18:1/16:0)/PC 36:4, Cer(d18:1/16:0)/PC 33:3 (PC O-34:3), Cer(d18:1/16:0)/SM (d18:1/18:0), Cer(d18:1/16:0)/SM (d18:1/23:0) (d18:1/22:1-OH), Cer(d18:1/16:0)/SM (d18:1/24:0) (d18:1/23:1-OH), Cer(d18:1/16:0)/SM (d18:1/24:1) (d18:1/23:2-OH), Cer(d18:1/16:0)/SM (d18:1/25:1) (d18:1/24:2-OH), Cer(d18:1/16:0)/Total CE, Cer(d18:1/16:0)/Total LPC, Cer(d18:1/16:0)/Total PC, Cer(d18:1/20:0)/LPC 18:2, Cer(d18:1/22:0)/LPC 18:2, Cer(d18:1/22:0)/PC 33:3 (PC O-34:3), Cer(d18:1/22:0)/SM (d18:1/24:0)(d18:1/23:1-OH), Cer(d18:1/24:1)/LPC 18:2, Cer(d18:1/24:1)/PC 33:3 (PC 0-34:3), Cer(d18:1/24:1)/SM (d18:1/23:0) (d18:1/22:1-OH), Cer(d18:1/24:1)/SM (d18:1/24:0) (d18:1/23:1-OH), Cer(d18:1/24:1)/SM (d18:1/25:1) (d18:1/24:2-OH), GlcCer(d18:1/16:0)/LPC 18:2, GlcCer(d18:1/18:0)/LPC 18:2, GlcCer(d18:1/26:1)/SM (d18:1/25:1) (d18:1/24:2-OH), LacCer(d18:1/18:0)/PC 36:4, LacCer(d18:1/22:0)/PC 16:0/20:4, LacCer(d18:1/22:0)/PC 18:0/20:4, LacCer(d18:1/22:0)/PC 35:4 (PC 0-36:4), LacCer(d18:1/22:0)/PC 36:4, LacCer(d18:1/22:0)/SM (d18:1/24:0) (d18:1/23:1-OH), LacCer(d18:1/22:0)/SM (d18:1/25:1) (d18:1/24:2-OH), LacCer(d18:1/22:0)/Total CE, LacCer(d18:1/24:1)/PC 16:0/20:4, LacCer(d18:1/24:1)/PC 18:0/20:4, LacCer(d18:1/24:1)/PC 36:4, LacCer(d18:1/24:1)/Total CE, PC 38:0/PC 38:5, Cer(d18:1/16:0)/Cer(d18:1/26:0), DAG 16:1/16:1/PC 32:1, DAG 16:1/16:1/PI 38:4, GM3-d18:1/24:1/SM (d18:1/16:1) (d18:1/15:2-OH), GM3-d18:1/24:1/SM (d18:1/18:1), GlcCer(d18:1/24:1)/SM (d18:1/23:1) (d18:1/22:2-OH), and SM (d18:1/16:0) (d18:1/15:1-OH)/

SM (d18:1/16:1) (d18:1/15:2-OH), PC 18:0/20:3/PC33:3 (PC O-34:3), GlcCer(d18:1/26:1)/LPC 18:2, LacCer(d18:1/24:1)/Total CE, Cer(d18:1/24:1)/Total CE, LacCer(d18:1/22:0)/Total CE, CE 22:2/LPC 20:4, Cer(d18:1/20:0)/SM (d18:1/23:0) (d18:1/22:1-OH), Cer(d18:1/22:0)/Total CE, LacCer(d18:1/18:0)/PC 40:7, GlcCer(d18:1/16:0)/SM (d18:1/24:0) (d18:1/23:1-OH), Cer(d18:1/24:1)/PC35:4 (PC O-36:4), Cer(d18:1/22:0)/SM (d18:1/23:0) (d18:1/22:1-OH), Cer(d18:1/20:0)/Total CE, Cer(d18:1/16:0)/PC 36:2, Cer(d18:1/16:0)/PC 18:0/18:2, Cer(d18:1/22:0)/PC 40:7, Cer(d18:1/22:0)/PC 39:0 (PC O-40:0), GlcCer(d18:1/18:0)/LPC 18:1, CE 20:0/PC 40:4, GlcCer(d18:1/16:0)/PC 36:2, LacCer(d18:1/16:0)/PC 35:2 (PC O-36:2), PC 39:7 (PC O-40:7)/Total CE, PC 38:0/Total CE, PC 38:0/PC 35:6 (PC O-36:5), Total LacCer/Total PC O, SM (d18:1/14:0) (d18:1/13:1-OH)/SM (d18:1/23:0) (d18:1/22:1-OH), LPC 18:1/PC 32:1, Cer(d18:1/24:1)/PC 32:1, GM3-d18:1/24:1/SM (d18:1/23:1) (d18:1/22:2-OH), GM3-d18:1/24:1/PC 32:1, DAG 16:1/16:1/PC 30:0, Cer(d18:1/24:1)/SM (d18:1/18:1), GM3-d18:1/24:1/SM (d18:1/18:1), GM3-d18:1/24:1/SM (d18:1/16:1) (d18:1/15:2-OH), Cer(d18:1/16:0)/PC 32:1, LacCer(d18:1/16:0)/PC 40:6, Cer(d18:1/24:1)/PC 38:4, LPC 18:0/PC 32:1, Cer(d18:1/24:1)/PC 34:2, GM3-d18:1/24:2/SM (d18:1/23:1) (d18:1/22:2-OH), GM3-d18:1/24:2/PC 32:1, GM3-d18:1/24:1/PC 34:2, GlcCer(d18:1/16:0)/PC 32:1, GM3-d18:1/24:1/PC 36:4, GM3-d18:1/16:0/SM (d18:1/23:1) (d18:1/22:2-OH), GM3-d18:1/24:1/PC 34:1, Cer(d18:1/16:0)/PC 34:2, GlcCer(d18:1/16:0)/PC 34:2, GM3-d18:1/16:0/PC 32:1, Cer(d18:1/16:0)/PC 34:1, Cer(d18:1/24:1)/PC 34:3, GlcCer(d18:1/16:0)/PC 34:1, GM3-d18:1/18:0/PC 32:1, Cer(d18:1/16:0)/PC 34:3, GlcCer(d18:1/16:0)/PC 34:3, LPC 16:0/SM (d18:1/14:0) (d18:1/13:1-OH), GlcCer(d18:1/20:0)/PC 34:3 and GlcCer(d18:1/18:0)/PC 34:3;

and wherein the one or more lipid-lipid ratio(s) whose decrease(s) is (are) compared to the control is (are) selected from:

LPC 20:4/PC 35:1 (PC O-36:1), CE 20:4/GlcCer(d18:1/26:1), CE 16:1/Total LacCer, CE 22:6/LacCer(d18:1/22:0), CE 16:1/PC 37:2 (PC O-38:2), CE 16:0/GlcCer(d18:1/16:0), CE 22:6/Cer(d18:1/16:0), CE 14:0/PC 37:2 (PC O-38:2), CE 16:0/Total LacCer, CE 18:2/Cer(d18:1/16:0), CE 16:0/LacCer(d18:1/22:0), CE 20:4/GlcCer(d18:1/24:1), CE 18:1/GlcCer(d18:1/16:0), CE 20:4/GlcCer(d18:1/16:0), CE 18:0/Cer(d18:1/16:0), LPC 20:4/PC 37:2 (PC O-38:2), CE 16:0/Cer(d18:1/24:1), CE 17:1/LacCer(d18:1/22:0), CE 18:2/GlcCer(d18:1/16:0), CE 22:6/GlcCer(d18:1/16:0), Total CE/Total LacCer, CE 14:0/Cer(d18:1/24:1), CE 20:4/LacCer(d18:1/16:0), CE 22:6/Total LacCer, CE 22:6/LacCer(d18:1/24:1), CE 18:1/Cer(d18:1/16:0), CE 16:1/Cer(d18:1/16:0), CE 16:1/LacCer(d18:1/22:0), CE 16:0/LacCer(d18:1/16:0), CE 16:1/CE 22:2, CE 16:1/Cer(d18:1/24:1), CE 22:6/LacCer(d18:1/18:0), CE 22:6/LacCer(d18:1/20:0), CE 20:4/LacCer(d18:1/22:0), CE 20:4/Cer(d18:1/24:1), CE 16:1/CE 20:0, CE 20:4/Cer(d18:1/16:0), LPC 20:4/PC 37:2 (PC O-38:2), CE 20:4/Total GlcCer, CE 20:4/Total LacCer, CE 20:4/SM (d18:1/14:0) (d18:1/13:1-OH), LPC 20:4/PC 35:1 (PC O-36:1), CE 14:0/Cer(d18:1/16:0), CE 17:1/Cer(d18:1/16:0), CE 17:1/Cer(d18:1/24:1), CE 20:4/GlcCer(d18:1/18:0), CE 16:0/Cer(d18:1/16:0), CE 18:1/Cer(d18:1/24:1), CE 16:0/Cer(d18:1/24:1), CE 16:0/DAG 16:1/16:1, CE 16:1/CE 20:3, CE 16:1/DAG 16:1/16:1, CE 16:1/GM3-d18:1/24:1, CE 16:1/LPC 16:0, CE 18:2/Cer(d18:1/24:1), CE 18:2/DAG 16:1/16:1, CE 18:2/GlcCer(d18:1/24:1), CE 18:2/GM3-d18:1/24:1, CE 18:3/Cer(d18:1/24:1), CE 20:4/DAG 16:1/16:1, Cer(d18:0/22:0)/PE 36:2, Cer(d18:0/24:0)/Cer(d18:1/16:0), Cer(d18:0/24:0)/DAG 16:1/16:1, Cer(d18:1/24:0)/Cer(d18:1/24:1), GD3-d18:1/16:0/GlcCer(d18:1/24:1), GlcCer(d18:1/26:0)/GlcCer(d18:1/26:1), GM3-d18:1/18:0/GlcCer(d18:1/24:1), GM3-d18:1/18:0/GM3-d18:1/24:1, GM3-d18:1/20:0/GM3-d18:1/24:1, GM3-d18:1/21:0/GM3-d18:1/24:1, GM3-d18:1/22:1/GM3-d18:1/24:1, GM3-d18:1/23:0/GM3-d18:1/24:1, PC 16:0/18:2/PE 36:2, PC 32:1/PC 36:1, PC 34:1/PE 36:2, PC 34:2/PE 36:2, PC 34:3/PE 36:2, PC 36:2/PE 36:2, SM (d18:1/16:1) (d18:1/15:2-OH)/SM (d18:1/24:1)(d18:1/23:2-OH), SM (d18:1/18:1)/SM (d18:1/24:1) (d18:1/23:2-OH), SM (d18:1/23:1) (d18:1/22:2-OH)/SM (d18:1/24:1) (d18:1/23:2-OH), SM (d18:1/23:0) (d18:1/22:1-OH)/Total Cer, CE 18:2/Cer(d18:1/22:0), PC 36:4/PC 38:0, CE 18:2/Total Cer, CE 20:4/Cer(d18:1/22:0), CE 18:1/LacCer(d18:1/16:0), CE 18:1/GlcCer(d18:1/18:0), CE 18:1/LacCer(d18:1/22:0), Total CE/Total LacCer, CE 18:1/Total LacCer, CE 18:1/LacCer(d18:1/24:1), CE 20:4/Cer(d18:1/24:1), LPC 18:2/LacCer(d18:1/22:0), CE 20:4/Total LacCer, CE 17:1/LacCer(d18:1/20:0), CE 20:4/LacCer(d18:1/24:1), CE 16:1/GlcCer(d18:1/18:0), LPC 20:4/PC 38:0, GM3-d18:1/20:0/GM3-d18:1/22:0, GM3-d18:1/22:1/GM3-d18:1/24:1, Cer(d18:1/26:0)/GlcCer(d18:1/16:0), GM3-d18:1/20:0/GM3-d18:1/24:1, CE 18:2/GlcCer(d18:1/26:1), CE 18:3/Cer(d18:1/16:0), CE 18:2/Cer(d18:1/24:1), GD3-d18:1/16:0/GM3-d18:1/24:1, Cer(d18:1/26:0)/GlcCer(d18:1/24:1), CE 16:1/LPC 16:0, CE 16:1/CE 20:3, CE 16:1/LPC 18:1, CE 16:1/DAG 16:1/16:1 and CE 16:1/LacCer(d18:1/16:0) (see Tables 3, 6, 9 and 12).

In a preferred embodiment, the one or more lipid-lipid ratio(s) whose increase is (are) compared to the control is (are) selected from:

CE 19:1/LPC 20:4, Cer(d18:1/24:1)/LPC 18:2, Cer(d18:1/16:0)/LPC 18:2, PC 38:0/PC 38:5, LacCer(d18:1/24:1)/PC 16:0/20:4, GlcCer(d18:1/26:1)/SM (d18:1/24:2-OH) (d18:1/25:1), Cer(d18:1/16:0)/SM (d18:1/24:1) (d18:1/23:2-OH), Cer(d18:1/16:0)/PC 18:1/18:2, Cer(d18:1/16:0)/PC 35:3 (PC O-34:3), GlcCer(d18:1/16:0)/LPC 18:2, LacCer(d18:1/22:0)/SM (d18:1/24:0) (d18:1/23:1-OH), LacCer(d18:1/22:0)/PC 35:4 (PC O-36:4), LacCer(d18:1/24:1)/Total CE, Cer(d18:1/16:0)/PC 36:3, Cer(d18:1/16:0)/LPC 18:1, LacCer(d18:1/22:0)/PC 16:0/20:4, Cer(d18:1/16:0)/Cer(d18:1/26:0), DAG 16:1/16:1/PC 32:1, GM3-d18:1/24:1/SM (d18:1/16:1) (d18:1/15:2-OH), and GM3-d18:1/24:1/SM (d18:1/18:1).

In another preferred embodiment, the one or more lipid-lipid ratio(s) whose decrease is (are) compared to the control is (are) selected from:

CE 16:0/Cer(d18:1/16:0), CE 18:2/Cer(d18:1/16:0), CE 20:4/GlcCer(d18:1/16:0), CE 18:1/Cer(d18:1/16:0), CE 22:6/Cer(d18:1/16:0), CE 16:1/PC 37:2 (PC O-38:2), CE 18:0/Cer(d18:1/16:0), CE 18:2/GlcCer(d18:1/16:0), CE 16:0/GlcCer(d18:1/16:0), LPC 20:4/PC 35:1 (PC O-36:1), Total CE/Total LacCer, CE 20:4/Cer(d18:1/24:1), CE 16:1/DAG 16:1/16:1, CE 18:2/Cer(d18:1/24:1), CE 18:2/Cer(d18:1/16:0), Cer(d18:1/24:0)/Cer(d18:1/24:1), Cer(d18:0/24:0)/DAG 16:1/16:1, Cer(d18:0/24:0)/Cer(d18:1/16:0), GD3-d18:1/16:0/GlcCer(d18:1/24:1), GlcCer(d18:1/26:0)/GlcCer(d18:1/26:1), GM3-d18:1/22:1/GM3-d18:1/24:1, GM3-d18:1/20:0/GM3-d18:1/24:1, GM3-d18:1/18:0/GlcCer(d18:1/24:1), PC 16:0/18:2/PE 36:2, SM (d18:1/23:1) (d18:1/22:2-OH)/SM (d18:1/24:1) (d18:1/23:2-OH), CE 16:1/CE 20:3, CE 16:1/Cer(d18:1/16:0), and CE 16:1/LPC 16:0 (see Tables 16 and 17).

In a particularly preferred embodiment, the one or more lipid-lipid ratio(s) whose increase is (are) compared to the control is (are) selected from:
Cer(d18:1/16:0)/LPC 18:1, LacCer(d18:1/24:1)/Total CE, CE 19:1/LPC 20:4, and Cer(d18:1/16:0)/PC 36:3;
and the lipid-lipid ratio whose decrease is compared to the control is:
CE 20:4/Cer(18:1/24:1) (see Table 20).

In yet another alternative embodiment the present invention relates to a method for determining whether a subject is at risk to develop, or is suffering from atherosclerosis or cardiovascular disease (CVD) and/or one or more of their complications, such as AMI or CVD death, comprising determining in a sample from said subject one or more lipid-clinical concentration ratio(s), wherein (an) increased or decreased lipid-clinical concentration ratio(s) in said sample, when compared to a control sample, is (are) indicative of said subject suffering from or having an increased risk of developing atherosclerosis or CVD and/or one or more of their complications, such as AMI or CVD death, wherein the one or more lipid-clinical concentration ratio(s) whose increase is (are) compared to the control is (are) selected from:
Cer(d18:0/22:0)/apolipoprotein A-I (mg/dL), Cer(d18:0/22:0)/apolipoprotein A-II (mg/dL), Cer(d18:0/22:0)/HDL cholesterol ester (mg/dL), Cer(d18:0/24:1)/apolipoprotein A-II (mg/dL), Cer(d18:0/24:1)/cholesterol ester (mg/dL), Cer(d18:0/24:1)/HDL cholesterol ester (mg/dL), Cer(d18:1/16:0)/apolipoprotein A-I (mg/dL), Cer(d18:1/16:0)/apolipoprotein A-II (mg/dL), Cer(d18:1/16:0)/apolipoprotein B (mg/dL), Cer(d18:1/16:0)/apolipoprotein E (mg/dL), Cer(d18:1/16:0)/body mass index (kg/m2), Cer(d18:1/16:0)/cholesterol ester (mg/dL), Cer(d18:1/16:0)/free cholesterol (mg/dL), Cer(d18:1/16:0)/HDL cholesterol (EDTA) (mg/dL), Cer(d18:1/16:0)/HDL cholesterol ester (mg/dL), Cer(d18:1/16:0)/HDL phospholipid (mg/dL), Cer(d18:1/16:0)/LDL phospholipid (mg/dL), Cer(d18:1/16:0)/phospholipid (mg/dL), Cer(d18:1/16:0)/total cholesterol (EDTA) (mg/dL), Cer(d18:1/22:0)/apolipoprotein A-I (mg/dL), Cer(d18:1/22:0)/apolipoprotein A-II (mg/dL), Cer(d18:1/24:1)/apolipoprotein A-I (mg/dL), Cer(d18:1/24:1)/apolipoprotein A-II (mg/dL), Cer(d18:1/24:1)/cholesterol ester (mg/dL), Cer(d18:1/24:1)/HDL cholesterol ester (mg/dL), Cer(d18:1/24:1)/total cholesterol (EDTA) (mg/dL), GlcCer(d18:1/16:0)/apolipoprotein A-I (mg/dL), GlcCer(d18:1/16:0)/apolipoprotein A-II (mg/dL), GlcCer(d18:1/16:0)/cholesterol ester (mg/dL), GlcCer(d18:1/18:0)/apolipoprotein A-I (mg/dL), GlcCer(d18:1/18:0)/apolipoprotein A-II (mg/dL), GlcCer(d18:1/18:0)/cholesterol ester (mg/dL), GlcCer(d18:1/26:1)/apolipoprotein A-II (mg/dL), GlcCer(d18:1/26:1)/cholesterol ester (mg/dL), LacCer(d18:1/22:0)/apolipoprotein A-I (mg/dL), LacCer(d18:1/22:0)/apolipoprotein A-II (mg/dL), LacCer(d18:1/22:0)/cholesterol ester (mg/dL), LacCer(d18:1/22:0)/HDL cholesterol (EDTA) (mg/dL), LacCer(d18:1/22:0)/HDL cholesterol ester (mg/dL), LacCer(d18:1/22:0)/LDL free cholesterol (mg/dL), LacCer(d18:1/22:0)/total cholesterol (EDTA) (mg/dL), LacCer(d18:1/24:1)/apolipoprotein A-I (mg/dL), LacCer(d18:1/24:1)/apolipoprotein A-II (mg/dL), LacCer(d18:1/24:1)/cholesterol ester (mg/dL), LacCer(d18:1/24:1)/HDL cholesterol ester (mg/dL), PC 18:0/20:3/VLDL apolipoprotein B (mg/dL), Total Cer/apolipoprotein A-I (mg/dL), Total Cer/apolipoprotein A-II (mg/dL), Total LacCer/apolipoprotein A-I (mg/dL), Total LacCer/apolipoprotein A-II (mg/dL), DAG 16:1/16:1/HDL, GM3-d18:1/24:2/HDL, GlcCer(d18:1/26:1)/HDL, Cer(d18:1/24:1)/LDL, GM3-d18:1/16:0/HDL, Cer(d18:1/24:1)/Chol, Cer(d18:1/16:0)/Chol, Cer(d18:1/24:1)/HDL, GM3-d18:1/24:1/HDL, GlcCer(d18:1/24:1)/HDL, Cer(d18:1/16:0)/HDL, Cer(d18:1/16:0)/apolipoprotein A-II (mg/dL), LacCer(d18:1/24:1)/apolipoprotein E (mg/dL), Cer(d18:1/24:1)/HDL cholesterol ester (mg/dL), LacCer(d18:1/22:0)/HDL cholesterol ester (mg/dL), LacCer(d18:1/24:0)/HDL cholesterol ester (mg/dL), LacCer(d18:1/24:0)/apolipoprotein C-II (mg/dL), GlcCer(d18:1/16:0)/HDL cholesterol ester (mg/dL), LacCer(d18:1/24:1)/apolipoprotein A-I (mg/dL), Total LacCer/HDL cholesterol ester (mg/dL), Cer(d18:1/22:0)/apolipoprotein A-II (mg/dL), LacCer(d18:1/22:0)/HDL cholesterol (EDTA) (mg/dL), Cer(d18:1/20:0)/apolipoprotein A-I (mg/dL), LacCer(d18:1/24:0)/HDL cholesterol (EDTA) (mg/dL), LacCer(d18:1/18:0)/LDL cholesterol (EDTA) (mg/dL), Cer(d18:1/22:0)/apolipoprotein A-I (mg/dL), GlcCer(d18:1/18:0)/apolipoprotein A-I (mg/dL), LacCer(d18:1/16:0)/HDL cholesterol ester (mg/dL), Cer(d18:1/24:1)/cholesterol ester (mg/dL), Total LacCer/apolipoprotein A-I (mg/dL), Cer(d18:1/20:0)/HDL phospholipid (mg/dL), Total LacCer/cholesterol ester (mg/dL), LacCer(d18:1/24:1)/LDL cholesterol ester (mg/dL), Cer(d18:1/24:1)/total cholesterol (EDTA) (mg/dL), GlcCer(d18:1/24:0)/apolipoprotein A-I (mg/dL), LacCer(d18:1/24:1)/LDL cholesterol (EDTA) (mg/dL), Cer(d18:1/24:1)/LDL phospholipid (mg/dL), Total GlcCer/apolipoprotein A-I (mg/dL), LacCer(d18:1/24:1)/LDL free cholesterol (mg/dL), Cer(d18:1/22:0)/cholesterol ester (mg/dL), LacCer(d18:1/24:1)/apolipoprotein B (mg/dL), Cer(d18:1/22:0)/LDL cholesterol (EDTA) (mg/dL), Total Cer/cholesterol ester (mg/dL), LacCer(d18:1/16:0)/cholesterol ester (mg/dL), Cer(d18:1/22:0)/total cholesterol (EDTA) (mg/dL), LacCer(d18:1/24:1)/HDL free cholesterol (mg/dL), Total LacCer/LDL cholesterol ester (mg/dL), Total LacCer/LDL cholesterol (EDTA) (mg/dL), Total Cer/total cholesterol (EDTA) (mg/dL), Total LacCer/phospholipid (mg/dL), GlcCer(d18:1/20:0)/cholesterol ester (mg/dL), Total LacCer/HDL free cholesterol (mg/dL), Total LacCer/apolipoprotein B (mg/dL), LacCer(d18:1/16:0)/LDL cholesterol ester (mg/dL), Total LacCer/LDL phospholipid (mg/dL), LacCer(d18:1/16:0)/LDL cholesterol (EDTA) (mg/dL), GlcCer(d18:1/24:1)/HDL, DAG 16:1/16:1/HDL, Cer(d18:1/24:1)/LDL, Cer(d18:1/24:1)/Chol, and Cer(d18:1/16:0)/Chol;
and wherein the one or more lipid-clinical concentration ratio(s) whose decrease is (are) compared to the control is (are) selected from:
CE 14:0/free fatty acids (mmol/L), CE 16:0/apolipoprotein C-III (mg/dL), CE 17:1/apolipoprotein C-III (mg/dL), CE 17:1/free fatty acids (mmol/L), CE 17:1/free glycerol (mg/dL), CE 18:0/apolipoprotein C-III (mg/dL), CE 18:1/apolipoprotein C-III (mg/dL), CE 18:2/apolipoprotein C-III (mg/dL), CE 20:3/free fatty acids (mmol/L), CE 20:4/apolipoprotein C-III (mg/dL), CE 20:4/free fatty acids (mmol/L), LPC 18:2/apolipoprotein C-III (mg/dL), PC 18:1/18:2/apolipoprotein C-III (mg/dL), PC 39:0 (PC O-40:0)/free fatty acids (mmol/L), PC 40:7/free fatty acids (mmol/L), SM (d18:1/23:0) (d18:1/22:1-OH)/apolipoprotein C-III (mg/dL), SM (d18:1/23:0) (d18:1/22:1-OH)/free fatty acids (mmol/L), SM (d18:1/25:1) (d18:1/24:2-OH)/free fatty acids (mmol/L), Total CE/apolipoprotein C-III (mg/dL), CE 14:0/TG, CE 16:0/TG, CE 16:1/Chol, CE 16:1/TG, CE 18:0/TG, CE 18:2/TG, CE 18:3/TG, CE 20:4/TG, Cer(d18:0/22:0)/TG, Cer(d18:0/24:0)/TG, Cer(d18:0/24:1)/TG, Cer(d18:1/24:0)/TG, Cer(d18:1/26:0)/TG, DAG 18:1/18:2/TG, GD1-d18:1/16:0/TG, GD3-d18:1/16:0/TG, GM3-d18:1/18:0/TG, GM3-d18:1/21:0/TG, LacCer(d18:1/22:0)/TG, PC 16:0/16:1/TG, PC 16:0/18:1/TG, PC 16:0/

18:2/TG, PC 16:0/20:4/TG, PC 16:0/22:5/TG, PC 16:0/22: 6/TG, PC 18:0/18:2/TG, PC 18:0/20:3/TG, PC 18:2/18:2/ TG, PC 30:0/TG, PC 32:1/TG, PC 34:1/TG, PC 34:2/TG, PC 34:3/TG, PC 35:2/TG, PC 36:2/TG, PC 36:4/TG, PC 38:3/TG, PC 38:4/TG, PC 40:6/TG, PC 35:2 (PC O-36:2)/ TG, PI 36:2/TG, PI 38:3/TG, PI 38:4/TG, SM (d18:1/14:0) (d18:1/13:1-OH)/TG, SM (d18:1/16:1) (d18:1/15:2-OH)/ TG, SM (d18:1/17:0) (d18:1/16:1-OH)/TG, SM (d18:1/ 18:1)/TG, SM (d18:1/23:1) (d18:1/22:2-OH)/TG, SM (d18:1/24:0) (d18:1/23:1-OH)/TG, CE 20:4/apolipoprotein C-III (mg/dL), CE 14:0/apolipoprotein C-III (mg/dL), CE 20:4/free fatty acids (mmol/L), LPC 20:4/free fatty acids (mmol/L), Total PC 0/C-reactive protein (mg/dL), Cer(d18:1/24:0)/Chol, CE 18:0/LDL, CE 18:2/LDL, Cer (d18:1/26:0)/Chol, CE 18:2/Chol, CE 20:5/LDL, CE 18:3/ Chol, CE 20:5/Chol, PE 38:5/TG, CE 17:0/TG, CE 16:1/ Chol, Cer(d18:1/22:0)/TG, PE 38:4/TG, Cer(d18:1/18:0)/ TG, CE 22:6/TG, CE 15:0/TG, DAG 18:1/18:2/TG, PC 18:0/20:5/TG, PC 32:0/TG, CE 16:0/TG, Cer(d18:1/24:0)/ TG, CE 20:5/TG, PC 40:6/TG, GM3-d18:1/21:0/TG, SM (d18:1/24:0) (d18:1/23:1-OH)/TG, PC 35:2 (PC O-36:2)/ TG, CE 18:3/TG, PC 35:2 (PC O-34:2)/TG, PC 16:0/20: 5/TG, CE 18:2/TG, CE 18:0/TG, PC 16:0/18:2/TG, PC 16:0/22:6/TG, CE 14:0/TG, PC 34:1/TG, SM (d18:1/17:0) (d18:1/16:1-OH)/TG, PC 36:5/TG, PC 38:3/TG, PC 18:0/ 20:3/TG, SM (d18:1/14:0) (d18:1/13:1-OH)/TG, PC 34:2/ TG, SM (d18:1/23:1) (d18:1/22:2-OH)/TG, CE 16:1/TG, PC 18:2/18:2/TG and PC 32:1/TG. (see Tables 4, 7, 10 and 13).

In a preferred embodiment, the one or more lipid-clinical concentration ratio(s) whose increase is (are) compared to the control is (are) selected from:

Cer(d18:0/22:0)/apolipoprotein A-I (mg/dL), Cer(d18:0/24: 1)/cholesterol ester (mg/dL), Cer(d18:1/16:0)/apolipoprotein A-I (mg/dL), Cer(d18:1/24:1)/apolipoprotein A-I (mg/ dL), GlcCer(d18:1/16:0)/apolipoprotein A-I (mg/dL), GlcCer(d18:1/18:0)/apolipoprotein A-I (mg/dL), LacCer (d18:1/22:0)/apolipoprotein A-I (mg/dL), LacCer(d18:1/ 22:0)/HDL cholesterol ester (mg/dL), Cer(d18:1/24:1)/ HDL cholesterol ester (mg/dL), LacCer(d18:1/22:0)/total cholesterol (EDTA) (mg/dL), Cer(d18:1/24:1)/total cholesterol (EDTA) (mg/dL), Cer(d18:1/16:0)/apolipoprotein A-II (mg/dL), Cer(d18:1/22:0)/apolipoprotein A-II (mg/ dL), LacCer(d18:1/24:1)/apolipoprotein A-I (mg/dL), Cer (d18:1/16:0)/HDL, Cer(d18:1/24:1)/HDL, DAG 16:1/16: 1/HDL, GlcCer(d18:1/24:1)/HDL, GlcCer(d18:1/26:1)/ HDL, GM3-d18:1/16:0/HDL, GM3-d18:1/24:1/HDL, Cer (d18:1/24:1)/Chol, and GM3-d18:1/24:2/HDL.

In another preferred embodiment, the one or more lipid-clinical concentration ratio(s) whose decrease is (are) compared to the control is (are) selected from:

LPC 18:2/apolipoprotein C-III (mg/dL), SM (d18:1/25:1) (d18:1/24:2-OH)/free fatty acids (mmol/L), CE 18:2/apolipoprotein C-III (mg/dL), CE 20:4/apolipoprotein C-III (mg/dL), Cer(d18:0/24:0)/TG, DAG 18:1/18:2/TG, PC 18:0/20:3/TG, CE 18:2/TG, SM (d18:1/18:1)/TG, Cer (d18:1/24:0)/TG, PI 38:3/TG, GD3-d18:1/16:0/TG, LacCer(d18:1/22:0)/TG, GM3-d18:1/21:0/TG, GD1-d18:1/ 16:0/TG, GM3-d18:1/18:0/TG, PC 16:0/18:2/TG, CE 16:1/TG, SM (d18:1/14:0) (d18:1/13:1-OH)/TG, SM (d18:1/23:1) (d18:1/22:2-OH)/TG, PC 18:2/18:2/TG, and CE 16:1/Chol. (see Tables 18 and 19).

In a particularly preferred embodiment, the lipid-clinical concentration ratio whose increase is compared to the control is: GlcCer(d18:1/18:0)/apolipoprotein A-I (mg/dL) (see Table 20).

In another aspect the present invention relates to a method for evaluating the effectiveness of a treatment of atherosclerosis or CVD and/or one or more of their complications, such as AMI or CVD death, in a subject, comprising determining in a sample from said subject the concentration(s) of one or more lipid(s), wherein (an) increased or decreased concentration(s) in said sample, when compared to a control sample, is (are) indicative of effectiveness of said treatment, wherein the one or more lipid(s) whose increase(s) in concentration is (are) compared to the control is (are) selected from:

Cer(d18:0/22:0), Cer(d18:0/24:0), Cer(d18:0/24:1), Cer (d18:1/16:0), Cer(d18:1/18:0), Cer(d18:1/20:0), Cer(d18: 1/24:1), GlcCer(d18:1/16:0), GlcCer(d18:1/18:0), LacCer (d18:1/18:0), LacCer(d18:1/20:0), LacCer(d18:1/22:0), LacCer(d18:1/24:1), Total LacCer; LacCer(d18:1/24:0), Total Cer, GlcCer(d18:1/24:0), Total GlcCer and LacCer (d18:1/16:0);

and wherein the one or more lipid(s) whose decrease(s) in concentration is (are) compared to the control is (are) selected from:

CE 14:0, CE 16:0, CE 17:1, CE 20:3, PC 35:3 (PC O-34:3), Cer(d18:0/24:0), GD3-d18:1/16:0, PC 16:0/16:1, PC 37:5 (PC O-38:5), SM (d18:1/16:1) (d18:1/15:2-OH), SM (d18: 1/18:1), SM (d18:1/23:1) (d18:1/22:2-OH), Total CE, Total GD3, Total PC 0, Total PC, PC 16:0/20:4, CE 18:0, Cer(d18:1/26:1), CE 15:0, SM (d18:1/15:0)(d18:1/14:1-OH), GM3-d18:1/18:0, PC 37:5 (PC O-36:5), GM3-d18: 1/21:0, PC 16:0/18:2, Total PI, SM (d18:1/17:0) (d18:1/16: 1-OH), Cer(d18:1/26:0), PC 18:0/20:5, PI 38:3, PC 40:5, GM2-d18:1/18:0, Total GM2, GD1-d18:1/16:0, PC 16:0/ 20:5, PC 16:0/22:5, PC 18:0/20:3, PC 16:0/22:6, PI 38:4, and PC 16:0/20:4 (see Tables 2 and 5, 8 and 11).

In a preferred embodiment, the one or more lipid(s) whose increase in concentration is (are) compared to the control is (are) selected from:

Cer(d18:0/22:0), Cer(d18:0/24:0), Cer(d18:0/24:1), Cer (d18:1/16:0), Cer(d18:1/18:0), Cer(d18:1/24:1), GlcCer (d18:1/16:0), GlcCer(d18:1/18:0), LacCer(d18:1/18:0), LacCer(d18:1/20:0), LacCer(d18:1/22:0), and LacCer (d18:1/24:1).

In another preferred embodiment, the one or more lipid(s) whose decrease in concentration is (are) compared to the control is (are) selected from:

CE 16:0, CE 17:1, PC 35:3 (PC O-34:3), CE 14:0, CE 20:3, Total CE, Cer(d18:0/24:0), GD3-d18:1/16:0, PC 16:0/16: 1, PC 37:5 (PC O-38:5), SM (d18:1/18:1), SM (d18:1/23: 1) (d18:1/22:2-OH), SM (d18:1/16:1) (d18:1/15:2-OH), Total GD3, and Total PC (see Tables 14 and 15).

In a particularly preferred embodiment, the one or more lipid(s) whose increase in concentration is (are) compared to the control is (are) selected from:

Cer(d18:1/16:0), LacCer(d18:1/22:0), and LacCer(d18:1/24: 1);

and the one or more lipid(s) whose decrease in concentration is (are) compared to the control is (are) selected from:

CE 14:0 and CE 20:3 (see Table 20).

In another alternative embodiment the invention relates to a method for evaluating the effectiveness of a treatment of atherosclerosis or CVD and/or one or more of their complications, such as AMI or CVD death, in a subject, comprising determining in a sample from said subject one or more lipid-lipid ratio(s), wherein (an) increased or decreased lipid-lipid ratio(s) in said sample, when compared to a control sample, is (are) indicative of effectiveness of said treatment, wherein the one or more lipid-lipid ratio(s) whose increase(s) is (are) compared to the control is (are) selected from:

CE 19:1/LPC 20:4, Cer(d18:1/16:0)/LPC 16:0, Cer(d18:1/16:0)/LPC 18:1, Cer(d18:1/16:0)/LPC 18:2, Cer(d18:1/16:0)/PC 16:0/20:4, Cer(d18:1/16:0)/PC 18:1/18:2, Cer(d18:1/16:0)/PC 33:2 (PC O-34:2), Cer(d18:1/16:0)/PC 35:3 (PC 0-36:3), Cer(d18:1/16:0)/PC 35:4 (PC O-36:4), Cer(d18:1/16:0)/PC 36:3, Cer(d18:1/16:0)/PC 36:4, Cer(d18:1/16:0)/PC 33:3 (PC O-34:3), Cer(d18:1/16:0)/SM (d18:1/18:0), Cer(d18:1/16:0)/SM (d18:1/23:0) (d18:1/22:1-OH), Cer(d18:1/16:0)/SM (d18:1/24:0) (d18:1/23:1-OH), Cer(d18:1/16:0)/SM (d18:1/24:1) (d18:1/23:2-OH), Cer(d18:1/16:0)/SM (d18:1/25:1) (d18:1/24:2-OH), Cer(d18:1/16:0)/Total CE, Cer(d18:1/16:0)/Total LPC, Cer(d18:1/16:0)/Total PC, Cer(d18:1/20:0)/LPC 18:2, Cer(d18:1/22:0)/LPC 18:2, Cer(d18:1/22:0)/PC 33:3 (PC O-34:3), Cer(d18:1/22:0)/SM (d18:1/24:0)(d18:1/23:1-OH), Cer(d18:1/24:1)/LPC 18:2, Cer(d18:1/24:1)/PC 33:3 (PC 0-34:3), Cer(d18:1/24:1)/SM (d18:1/23:0) (d18:1/22:1-OH), Cer(d18:1/24:1)/SM (d18:1/24:0) (d18:1/23:1-OH), Cer(d18:1/24:1)/SM (d18:1/25:1) (d18:1/24:2-OH), GlcCer(d18:1/16:0)/LPC 18:2, GlcCer(d18:1/18:0)/LPC 18:2, GlcCer(d18:1/26:1)/SM (d18:1/25:1) (d18:1/24:2-OH), LacCer(d18:1/18:0)/PC 36:4, LacCer(d18:1/22:0)/PC 16:0/20:4, LacCer(d18:1/22:0)/PC 18:0/20:4, LacCer(d18:1/22:0)/PC 35:4 (PC 0-36:4), LacCer(d18:1/22:0)/PC 36:4, LacCer(d18:1/22:0)/SM (d18:1/24:0) (d18:1/23:1-OH), LacCer(d18:1/22:0)/SM (d18:1/25:1) (d18:1/24:2-OH), LacCer(d18:1/22:0)/Total CE, LacCer(d18:1/24:1)/PC 16:0/20:4, LacCer(d18:1/24:1)/PC 18:0/20:4, LacCer(d18:1/24:1)/PC 36:4, LacCer(d18:1/24:1)/Total CE, PC 38:0/PC 38:5, Cer(d18:1/16:0)/Cer(d18:1/26:0), DAG 16:1/16:1/PC 32:1, DAG 16:1/16:1/PI 38:4, GM3-d18:1/24:1/SM (d18:1/16:1) (d18:1/15:2-OH), GM3-d18:1/24:1/SM (d18:1/18:1), GlcCer(d18:1/24:1)/SM (d18:1/23:1) (d18:1/22:2-OH), SM (d18:1/16:0) (d18:1/15:1-OH)/SM (d18:1/16:1) (d18:1/15:2-OH); PC 18:0/20:3/PC33:3(PC 0-34:3), GlcCer(d18:1/26:1)/LPC 18:2, LacCer(d18:1/24:1)/Total CE, Cer(d18:1/24:1)/Total CE, LacCer(d18:1/22:0)/Total CE, CE 22:2/LPC 20:4, Cer(d18:1/20:0)/SM (d18:1/23:0) (d18:1/22:1-OH), Cer(d18:1/22:0)/Total CE, LacCer(d18:1/18:0)/PC 40:7, GlcCer(d18:1/16:0)/SM (d18:1/24:0) (d18:1/23:1-OH), Cer(d18:1/24:1)/PC35:4 (PC O-36:4), Cer(d18:1/22:0)/SM (d18:1/23:0) (d18:1/22:1-OH), Cer(d18:1/20:0)/Total CE, Cer(d18:1/16:0)/PC 36:2, Cer(d18:1/16:0)/PC 18:0/18:2, Cer(d18:1/22:0)/PC 40:7, Cer(d18:1/22:0)/PC 39:0 (PC O-40:0), GlcCer(d18:1/18:0)/LPC 18:1, CE 20:0/PC 40:4, GlcCer(d18:1/16:0)/PC 36:2, LacCer(d18:1/16:0)/PC 35:2 (PC O-36:2), PC 39:7 (PC O-40:7)/Total CE, PC 38:0/Total CE, PC 38:0/PC 35:6 (PC O-36:5), Total LacCer/Total PC O, SM (d18:1/14:0) (d18:1/13:1-OH)/SM (d18:1/23:0) (d18:1/22:1-OH), LPC 18:1/PC 32:1, Cer(d18:1/24:1)/PC 32:1, GM3-d18:1/24:1/SM (d18:1/23:1) (d18:1/22:2-OH), GM3-d18:1/24:1/PC 32:1, DAG 16:1/16:1/PC 30:0, Cer(d18:1/24:1)/SM (d18:1/18:1), GM3-d18:1/24:1/SM (d18:1/18:1), GM3-d18:1/24:1/SM (d18:1/16:1) (d18:1/15:2-OH), Cer(d18:1/16:0)/PC 32:1, LacCer(d18:1/16:0)/PC 40:6, Cer(d18:1/24:1)/PC 38:4, LPC 18:0/PC 32:1, Cer(d18:1/24:1)/PC 34:2, GM3-d18:1/24:2/SM (d18:1/23:1) (d18:1/22:2-OH), GM3-d18:1/24:2/PC 32:1, GM3-d18:1/24:1/PC 34:2, GlcCer(d18:1/16:0)/PC 32:1, GM3-d18:1/24:1/PC 36:4, GM3-d18:1/16:0/SM (d18:1/23:1) (d18:1/22:2-OH), GM3-d18:1/24:1/PC 34:1, Cer(d18:1/16:0)/PC 34:2, GlcCer(d18:1/16:0)/PC 34:2, GM3-d18:1/16:0/PC 32:1, Cer(d18:1/16:0)/PC 34:1, Cer(d18:1/24:1)/PC 34:3, GlcCer(d18:1/16:0)/PC 34:1, GM3-d18:1/18:0/PC 32:1, Cer(d18:1/16:0)/PC 34:3, GlcCer(d18:1/16:0)/PC 34:3, LPC 16:0/SM (d18:1/14:0) (d18:1/13:1-OH), GlcCer(d18:1/20:0)/PC 34:3 and GlcCer(d18:1/18:0)/PC 34:3;

and wherein one or more lipid-lipid ratio(s) whose decrease is (are) compared to the control is (are) selected from:

LPC 20:4/PC 35:1 (PC O-36:1), CE 20:4/GlcCer(d18:1/26:1), CE 16:1/Total LacCer, CE 22:6/LacCer(d18:1/22:0), CE 16:1/PC 37:2 (PC O-38:2), CE 16:0/GlcCer(d18:1/16:0), CE 22:6/Cer(d18:1/16:0), CE 14:0/PC 37:2 (PC O-38:2), CE 16:0/Total LacCer, CE 18:2/Cer(d18:1/16:0), CE 16:0/LacCer(d18:1/22:0), CE 20:4/GlcCer(d18:1/24:1), CE 18:1/GlcCer(d18:1/16:0), CE 20:4/GlcCer(d18:1/16:0), CE 18:0/Cer(d18:1/16:0), LPC 20:4/PC 37:2 (PC O-38:2), CE 16:0/Cer(d18:1/24:1), CE 17:1/LacCer(d18:1/22:0), CE 18:2/GlcCer(d18:1/16:0), CE 22:6/GlcCer(d18:1/16:0), Total CE/Total LacCer, CE 14:0/Cer(d18:1/24:1), CE 20:4/LacCer(d18:1/16:0), CE 22:6/Total LacCer, CE 22:6/LacCer(d18:1/24:1), CE 18:1/Cer(d18:1/16:0), CE 16:1/Cer(d18:1/16:0), CE 16:1/LacCer(d18:1/22:0), CE 16:0/LacCer(d18:1/16:0), CE 16:1/CE 22:2, CE 16:1/Cer(d18:1/24:1), CE 22:6/LacCer(d18:1/18:0), CE 22:6/LacCer(d18:1/20:0), CE 20:4/LacCer(d18:1/22:0), CE 20:4/Cer(d18:1/24:1), CE 16:1/CE 20:0, CE 20:4/Cer(d18:1/16:0), LPC 20:4/PC 37:2 (PC O-38:2), CE 20:4/Total GlcCer, CE 20:4/Total LacCer, CE 20:4/SM (d18:1/14:0) (d18:1/13:1-OH), LPC 20:4/PC 35:1 (PC O-36:1), CE 14:0/Cer(d18:1/16:0), CE 17:1/Cer(d18:1/16:0), CE 17:1/Cer(d18:1/24:1), CE 20:4/GlcCer(d18:1/18:0), CE 16:0/Cer(d18:1/16:0), CE 18:1/Cer(d18:1/24:1), CE 16:0/Cer(d18:1/24:1), CE 16:0/DAG 16:1/16:1, CE 16:1/CE 20:3, CE 16:1/DAG 16:1/16:1, CE 16:1/GM3-d18:1/24:1, CE 16:1/LPC 16:0, CE 18:2/Cer(d18:1/24:1), CE 18:2/DAG 16:1/16:1, CE 18:2/GlcCer(d18:1/24:1), CE 18:2/GM3-d18:1/24:1, CE 18:3/Cer(d18:1/24:1), CE 20:4/DAG 16:1/16:1, Cer(d18:0/22:0)/PE 36:2, Cer(d18:0/24:0)/Cer(d18:1/16:0), Cer(d18:0/24:0)/DAG 16:1/16:1, Cer(d18:1/24:0)/Cer(d18:1/24:1), GD3-d18:1/16:0/GlcCer(d18:1/24:1), GlcCer(d18:1/26:0)/GlcCer(d18:1/26:1), GM3-d18:1/18:0/GlcCer(d18:1/24:1), GM3-d18:1/18:0/GM3-d18:1/24:1, GM3-d18:1/20:0/GM3-d18:1/24:1, GM3-d18:1/21:0/GM3-d18:1/24:1, GM3-d18:1/22:1/GM3-d18:1/24:1, GM3-d18:1/23:0/GM3-d18:1/24:1, PC 16:0/18:2/PE 36:2, PC 32:1/PC 36:1, PC 34:1/PE 36:2, PC 34:2/PE 36:2, PC 34:3/PE 36:2, PC 36:2/PE 36:2, SM (d18:1/16:1) (d18:1/15:2-OH)/SM (d18:1/24:1)(d18:1/23:2-OH), SM (d18:1/18:1)/SM (d18:1/24:1) (d18:1/23:2-OH), SM (d18:1/23:1) (d18:1/22:2-OH)/SM (d18:1/24:1) (d18:1/23:2-OH), SM (d18:1/23:0) (d18:1/22:1-OH)/Total Cer, CE 18:2/Cer(d18:1/22:0), PC 36:4/PC 38:0, CE 18:2/Total Cer, CE 20:4/Cer(d18:1/22:0), CE 18:1/LacCer(d18:1/16:0), CE 18:1/GlcCer(d18:1/18:0), CE 18:1/LacCer(d18:1/22:0), Total CE/Total LacCer, CE 18:1/Total LacCer, CE 18:1/LacCer(d18:1/24:1), CE 20:4/Cer(d18:1/24:1), LPC 18:2/LacCer(d18:1/22:0), CE 20:4/Total LacCer, CE 17:1/LacCer(d18:1/20:0), CE 20:4/LacCer(d18:1/24:1), CE 16:1/GlcCer(d18:1/18:0), LPC 20:4/PC 38:0, GM3-d18:1/20:0/GM3-d18:1/22:0, GM3-d18:1/22:1/GM3-d18:1/24:1, Cer(d18:1/26:0)/GlcCer(d18:1/16:0), GM3-d18:1/20:0/GM3-d18:1/24:1, CE 18:2/GlcCer(d18:1/26:1), CE 18:3/Cer(d18:1/16:0), CE 18:2/Cer(d18:1/24:1), GD3-d18:1/16:0/GM3-d18:1/24:1, Cer(d18:1/26:0)/GlcCer(d18:1/24:1), CE 16:1/LPC 16:0, CE 16:1/CE 20:3, CE 16:1/LPC 18:1, CE 16:1/DAG 16:1/16:1 and CE 16:1/LacCer(d18:1/16:0) (see Tables 3 and 6).

In a preferred embodiment, the one or more lipid-lipid ratio(s) whose increase is (are) compared to the control is (are) selected from:

CE 19:1/LPC 20:4, Cer(d18:1/24:1)/LPC 18:2, Cer(d18:1/16:0)/LPC 18:2, PC 38:0/PC 38:5, LacCer(d18:1/24:1)/PC 16:0/20:4, GlcCer(d18:1/26:1)/SM (d18:1/24:2-OH) (d18:1/25:1), Cer(d18:1/16:0)/SM (d18:1/24:1) (d18:1/23:2-OH), Cer(d18:1/16:0)/PC 18:1/18:2, Cer(d18:1/16:0)/PC 35:3 (PC O-34:3), GlcCer(d18:1/16:0)/LPC 18:2, LacCer(d18:1/22:0)/SM (d18:1/24:0) (d18:1/23:1-OH), LacCer(d18:1/22:0)/PC 35:4 (PC O-36:4), LacCer(d18:1/24:1)/Total CE, Cer(d18:1/16:0)/PC 36:3, Cer(d18:1/16:0)/LPC 18:1, LacCer(d18:1/22:0)/PC 16:0/20:4, Cer(d18:1/16:0)/Cer(d18:1/26:0), DAG 16:1/16:1/PC 32:1, GM3-d18:1/24:1/SM (d18:1/16:1) (d18:1/15:2-OH), and GM3-d18:1/24:1/SM (d18:1/18:1).

In another preferred embodiment, the one or more lipid-lipid ratio(s) whose decrease is (are) compared to the control is (are) selected from:

CE 16:0/Cer(d18:1/16:0), CE 18:2/Cer(d18:1/16:0), CE 20:4/GlcCer(d18:1/16:0), CE 18:1/Cer(d18:1/16:0), CE 22:6/Cer(d18:1/16:0), CE 16:1/PC 37:2 (PC O-38:2), CE 18:0/Cer(d18:1/16:0), CE 18:2/GlcCer(d18:1/16:0), CE 16:0/GlcCer(d18:1/16:0), LPC 20:4/PC 35:1 (PC O-36:1), Total CE/Total LacCer, CE 20:4/Cer(d18:1/24:1), CE 16:1/DAG 16:1/16:1, CE 18:2/Cer(d18:1/24:1), CE 18:2/Cer(d18:1/16:0), Cer(d18:1/24:0)/Cer(d18:1/24:1), Cer(d18:0/24:0)/DAG 16:1/16:1, Cer(d18:0/24:0)/Cer(d18:1/16:0), GD3-d18:1/16:0/GlcCer(d18:1/24:1), GlcCer(d18:1/26:0)/GlcCer(d18:1/26:1), GM3-d18:1/22:1/GM3-d18:1/24:1, GM3-d18:1/20:0/GM3-d18:1/24:1, GM3-d18:1/18:0/GlcCer(d18:1/24:1), PC 16:0/18:2/PE 36:2, SM (d18:1/23:1) (d18:1/22:2-OH)/SM (d18:1/24:1) (d18:1/23:2-OH), CE 16:1/CE 20:3, CE 16:1/Cer(d18:1/16:0), and CE 16:1/LPC 16:0 (see Tables 16 and 17).

In a particularly preferred embodiment, the one or more lipid-lipid ratio(s) whose increase is (are) compared to the control is (are) selected from:

Cer(d18:1/16:0)/LPC 18:1, LacCer(d18:1/24:1)/Total CE, CE 19:1/LPC 20:4, and Cer(d18:1/16:0)/PC 36:3;

and the lipid-lipid ratio whose decrease is compared to the control is:

CE 20:4/Cer(18:1/24:1) (see Table 20).

In yet another alternative embodiment the invention relates to a method for evaluating the effectiveness of a treatment of atherosclerosis or CVD and/or one or more of their complications, such as AMI or CVD death, in a subject, comprising determining in a sample from said subject one or more lipid-clinical concentration ratio(s), wherein (an) increased or decreased lipid-clinical concentration ratio(s) in said sample, when compared to a control sample, is (are) indicative of effectiveness of said treatment, wherein the one or more lipid-clinical concentration ratio(s) whose increase(s) is (are) compared to the control is (are) selected from:

Cer(d18:0/22:0)/apolipoprotein A-I (mg/dL), Cer(d18:0/22:0)/apolipoprotein A-II (mg/dL), Cer(d18:0/22:0)/HDL cholesterol ester (mg/dL), Cer(d18:0/24:1)/apolipoprotein A-II (mg/dL), Cer(d18:0/24:1)/cholesterol ester (mg/dL), Cer(d18:0/24:1)/HDL cholesterol ester (mg/dL), Cer(d18:1/16:0)/apolipoprotein A-I (mg/dL), Cer(d18:1/16:0)/apolipoprotein A-II (mg/dL), Cer(d18:1/16:0)/apolipoprotein B (mg/dL), Cer(d18:1/16:0)/apolipoprotein E (mg/dL), Cer(d18:1/16:0)/body mass index (kg/m2), Cer(d18:1/16:0)/cholesterol ester (mg/dL), Cer(d18:1/16:0)/free cholesterol (mg/dL), Cer(d18:1/16:0)/HDL cholesterol (EDTA) (mg/dL), Cer(d18:1/16:0)/HDL cholesterol ester (mg/dL), Cer(d18:1/16:0)/HDL phospholipid (mg/dL), Cer(d18:1/16:0)/LDL phospholipid (mg/dL), Cer(d18:1/16:0)/phospholipid (mg/dL), Cer(d18:1/16:0)/total cholesterol (EDTA) (mg/dL), Cer(d18:1/22:0)/apolipoprotein A-I (mg/dL), Cer(d18:1/22:0)/apolipoprotein A-II (mg/dL), Cer(d18:1/24:1)/apolipoprotein A-I (mg/dL), Cer(d18:1/24:1)/apolipoprotein A-II (mg/dL), Cer(d18:1/24:1)/cholesterol ester (mg/dL), Cer(d18:1/24:1)/HDL cholesterol ester (mg/dL), Cer(d18:1/24:1)/total cholesterol (EDTA) (mg/dL), GlcCer(d18:1/16:0)/apolipoprotein A-I (mg/dL), GlcCer(d18:1/16:0)/apolipoprotein A-II (mg/dL), GlcCer(d18:1/16:0)/cholesterol ester (mg/dL), GlcCer(d18:1/18:0)/apolipoprotein A-I (mg/dL), GlcCer(d18:1/18:0)/apolipoprotein A-II (mg/dL), GlcCer(d18:1/18:0)/cholesterol ester (mg/dL), GlcCer(d18:1/26:1)/apolipoprotein A-II (mg/dL), GlcCer(d18:1/26:1)/cholesterol ester (mg/dL), LacCer(d18:1/22:0)/apolipoprotein A-I (mg/dL), LacCer(d18:1/22:0)/apolipoprotein A-II (mg/dL), LacCer(d18:1/22:0)/cholesterol ester (mg/dL), LacCer(d18:1/22:0)/HDL cholesterol (EDTA) (mg/dL), LacCer(d18:1/22:0)/HDL cholesterol ester (mg/dL), LacCer(d18:1/22:0)/LDL free cholesterol (mg/dL), LacCer(d18:1/22:0)/total cholesterol (EDTA) (mg/dL), LacCer(d18:1/24:1)/apolipoprotein A-I (mg/dL), LacCer(d18:1/24:1)/apolipoprotein A-II (mg/dL), LacCer(d18:1/24:1)/cholesterol ester (mg/dL), LacCer(d18:1/24:1)/HDL cholesterol ester (mg/dL), PC 18:0/20:3/VLDL apolipoprotein B (mg/dL), Total Cer/apolipoprotein A-I (mg/dL), Total Cer/apolipoprotein A-II (mg/dL), Total LacCer/apolipoprotein A-I (mg/dL), Total LacCer/apolipoprotein A-II (mg/dL), DAG 16:1/16:1/HDL, GM3-d18:1/24:2/HDL, GlcCer(d18:1/26:1)/HDL, Cer(d18:1/24:1)/LDL, GM3-d18:1/16:0/HDL, Cer(d18:1/24:1)/Chol, Cer(d18:1/16:0)/Chol, Cer(d18:1/24:1)/HDL, GM3-d18:1/24:1/HDL, GlcCer(d18:1/24:1)/HDL, Cer(d18:1/16:0)/HDL, Cer(d18:1/16:0)/apolipoprotein A-II (mg/dL), LacCer(d18:1/24:1)/apolipoprotein E (mg/dL), Cer(d18:1/24:1)/HDL cholesterol ester (mg/dL), LacCer(d18:1/22:0)/HDL cholesterol ester (mg/dL), LacCer(d18:1/24:0)/HDL cholesterol ester (mg/dL), LacCer(d18:1/24:0)/apolipoprotein C-II (mg/dL), GlcCer(d18:1/16:0)/HDL cholesterol ester (mg/dL), LacCer(d18:1/24:1)/apolipoprotein A-I (mg/dL), Total LacCer/HDL cholesterol ester (mg/dL), Cer(d18:1/22:0)/apolipoprotein A-II (mg/dL), LacCer(d18:1/22:0)/HDL cholesterol (EDTA) (mg/dL), Cer(d18:1/20:0)/apolipoprotein A-I (mg/dL), LacCer(d18:1/24:0)/HDL cholesterol (EDTA) (mg/dL), LacCer(d18:1/18:0)/LDL cholesterol (EDTA) (mg/dL), Cer(d18:1/22:0)/apolipoprotein A-I (mg/dL), GlcCer(d18:1/18:0)/apolipoprotein A-I (mg/dL), LacCer(d18:1/16:0)/HDL cholesterol ester (mg/dL), Cer(d18:1/24:1)/cholesterol ester (mg/dL), Total LacCer/apolipoprotein A-I (mg/dL), Cer(d18:1/20:0)/HDL phospholipid (mg/dL), Total LacCer/cholesterol ester (mg/dL), LacCer(d18:1/24:1)/LDL cholesterol ester (mg/dL), Cer(d18:1/24:1)/total cholesterol (EDTA) (mg/dL), GlcCer(d18:1/24:0)/apolipoprotein A-I (mg/dL), LacCer(d18:1/24:1)/LDL cholesterol (EDTA) (mg/dL), Cer(d18:1/24:1)/LDL phospholipid (mg/dL), Total GlcCer/apolipoprotein A-I (mg/dL), LacCer(d18:1/24:1)/LDL free cholesterol (mg/dL), Cer(d18:1/22:0)/cholesterol ester (mg/dL), LacCer(d18:1/24:1)/apolipoprotein B (mg/dL), Cer(d18:1/22:0)/LDL cholesterol (EDTA) (mg/dL), Total Cer/cholesterol ester (mg/dL), LacCer(d18:1/16:0)/cholesterol ester (mg/dL), Cer(d18:1/22:0)/total cholesterol (EDTA) (mg/dL), LacCer(d18:1/24:1)/HDL free cholesterol (mg/dL), Total LacCer/LDL cholesterol ester (mg/dL), Total LacCer/LDL cholesterol (EDTA) (mg/dL), Total Cer/total cholesterol (EDTA) (mg/dL), Total LacCer/phospholipid (mg/dL), GlcCer(d18:1/20:0)/cholesterol ester (mg/dL), Total Lac-Cer/HDL free cholesterol (mg/dL), Total LacCer/apolipoprotein B (mg/dL), LacCer(d18:1/16:0)/LDL cholesterol ester (mg/dL), Total LacCer/LDL phospholipid (mg/dL), LacCer(d18:1/16:0)/LDL cholesterol (EDTA) (mg/dL), GlcCer(d18:1/24:1)/HDL, DAG 16:1/16:1/HDL, Cer(d18:1/24:1)/LDL, Cer(d18:1/24:1)/Chol, and Cer(d18:1/16:0)/Chol;

and wherein the one or more lipid-clinical concentration ratio(s) whose decrease is (are) compared to the control is (are) selected from: CE 14:0/free fatty acids (mmol/L), CE 16:0/apolipoprotein C-III (mg/dL), CE 17:1/apolipoprotein C-III (mg/dL), CE 17:1/free fatty acids (mmol/L), CE 17:1/free glycerol (mg/dL), CE 18:0/apolipoprotein C-III (mg/dL), CE 18:1/apolipoprotein C-III (mg/dL), CE 18:2/apolipoprotein C-III (mg/dL), CE 20:3/free fatty acids (mmol/L), CE 20:4/apolipoprotein C-III (mg/dL), CE 20:4/free fatty acids (mmol/L), LPC 18:2/apolipoprotein C-III (mg/dL), PC 18:1/18:2/apolipoprotein C-III (mg/dL), PC 39:0 (PC O-40:0)/free fatty acids (mmol/L), PC 40:7/free fatty acids (mmol/L), SM (d18:1/23:0) (d18:1/22:1-OH)/apolipoprotein C-III (mg/dL), SM (d18:1/23:0) (d18:1/22:1-OH)/free fatty acids (mmol/L), SM (d18:1/25:1) (d18:1/24:2-OH)/free fatty acids (mmol/L), Total CE/apolipoprotein C-III (mg/dL), CE 14:0/TG, CE 16:0/TG, CE 16:1/Chol, CE 16:1/TG, CE 18:0/TG, CE 18:2/TG, CE 18:3/TG, CE 20:4/TG, Cer(d18:0/22:0)/TG, Cer(d18:0/24:0)/TG, Cer(d18:0/24:1)/TG, Cer(d18:1/24:0)/TG, Cer(d18:1/26:0)/TG, DAG 18:1/18:2/TG, GD1-d18:1/16:0/TG, GD3-d18:1/16:0/TG, GM3-d18:1/18:0/TG, GM3-d18:1/21:0/TG, LacCer(d18:1/22:0)/TG, PC 16:0/16:1/TG, PC 16:0/18:1/TG, PC 16:0/18:2/TG, PC 16:0/20:4/TG, PC 16:0/22:5/TG, PC 16:0/22:6/TG, PC 18:0/18:2/TG, PC 18:0/20:3/TG, PC 18:2/18:2/TG, PC 30:0/TG, PC 32:1/TG, PC 34:1/TG, PC 34:2/TG, PC 34:3/TG, PC 35:2/TG, PC 36:2/TG, PC 36:4/TG, PC 38:3/TG, PC 38:4/TG, PC 40:6/TG, PC 35:2 (PC O-36:2)/TG, PI 36:2/TG, PI 38:3/TG, PI 38:4/TG, SM (d18:1/14:0) (d18:1/13:1-OH)/TG, SM (d18:1/16:1) (d18:1/15:2-OH)/TG, SM (d18:1/17:0) (d18:1/16:1-OH)/TG, SM (d18:1/18:1)/TG, SM (d18:1/23:1) (d18:1/22:2-OH)/TG, SM (d18:1/24:0) (d18:1/23:1-OH)/TG, CE 20:4/apolipoprotein C-III (mg/dL), CE 14:0/apolipoprotein C-III (mg/dL), CE 20:4/free fatty acids (mmol/L), LPC 20:4/free fatty acids (mmol/L), Total PC 0/C-reactive protein (mg/dL), Cer(d18:1/24:0)/Chol, CE 18:0/LDL, CE 18:2/LDL, Cer(d18:1/26:0)/Chol, CE 18:2/Chol, CE 20:5/LDL, CE 18:3/Chol, CE 20:5/Chol, PE 38:5/TG, CE 17:0/TG, CE 16:1/Chol, Cer(d18:1/22:0)/TG, PE 38:4/TG, Cer(d18:1/18:0)/TG, CE 22:6/TG, CE 15:0/TG, DAG 18:1/18:2/TG, PC 18:0/20:5/TG, PC 32:0/TG, CE 16:0/TG, Cer(d18:1/24:0)/TG, CE 20:5/TG, PC 40:6/TG, GM3-d18:1/21:0/TG, SM (d18:1/24:0) (d18:1/23:1-OH)/TG, PC 35:2 (PC O-36:2)/TG, CE 18:3/TG, PC 35:2 (PC O-34:2)/TG, PC 16:0/20:5/TG, CE 18:2/TG, CE 18:0/TG, PC 16:0/18:2/TG, PC 16:0/22:6/TG, CE 14:0/TG, PC 34:1/TG, SM (d18:1/17:0) (d18:1/16:1-OH)/TG, PC 36:5/TG, PC 38:3/TG, PC 18:0/20:3/TG, SM (d18:1/14:0) (d18:1/13:1-OH)/TG, PC 34:2/TG, SM (d18:1/23:1) (d18:1/22:2-OH)/TG, CE 16:1/TG, PC 18:2/18:2/TG and PC 32:1/TG (see Tables 4, 7, 10 and 13).

In a preferred embodiment, the one or more lipid-clinical concentration ratio(s) whose increase is (are) compared to the control is (are) selected from:
Cer(d18:0/22:0)/apolipoprotein A-I (mg/dL), Cer(d18:0/24:1)/cholesterol ester (mg/dL), Cer(d18:1/16:0)/apolipoprotein A-I (mg/dL), Cer(d18:1/24:1)/apolipoprotein A-I (mg/dL), GlcCer(d18:1/16:0)/apolipoprotein A-I (mg/dL), GlcCer(d18:1/18:0)/apolipoprotein A-I (mg/dL), LacCer(d18:1/22:0)/apolipoprotein A-I (mg/dL), LacCer(d18:1/22:0)/HDL cholesterol ester (mg/dL), Cer(d18:1/24:1)/HDL cholesterol ester (mg/dL), LacCer(d18:1/22:0)/total cholesterol (EDTA) (mg/dL), Cer(d18:1/24:1)/total cholesterol (EDTA) (mg/dL), Cer(d18:1/16:0)/apolipoprotein A-II (mg/dL), Cer(d18:1/22:0)/apolipoprotein A-II (mg/dL), LacCer(d18:1/24:1)/apolipoprotein A-I (mg/dL), Cer(d18:1/16:0)/HDL, Cer(d18:1/24:1)/HDL, DAG 16:1/16:1/HDL, GlcCer(d18:1/24:1)/HDL, GlcCer(d18:1/26:1)/HDL, GM3-d18:1/16:0/HDL, GM3-d18:1/24:1/HDL, Cer(d18:1/24:1)/Chol, and GM3-d18:1/24:2/HDL.

In another preferred embodiment, the one or more lipid-clinical concentration ratio(s) whose decrease is (are) compared to the control is (are) selected from:
LPC 18:2/apolipoprotein C-III (mg/dL), SM (d18:1/25:1) (d18:1/24:2-OH)/free fatty acids (mmol/L), CE 18:2/apolipoprotein C-III (mg/dL), CE 20:4/apolipoprotein C-III (mg/dL), Cer(d18:0/24:0)/TG, DAG 18:1/18:2/TG, PC 18:0/20:3/TG, CE 18:2/TG, SM (d18:1/18:1)/TG, Cer(d18:1/24:0)/TG, PI 38:3/TG, GD3-d18:1/16:0/TG, LacCer(d18:1/22:0)/TG, GM3-d18:1/21:0/TG, GD1-d18:1/16:0/TG, GM3-d18:1/18:0/TG, PC 16:0/18:2/TG, CE 16:1/TG, SM (d18:1/14:0) (d18:1/13:1-OH)/TG, SM (d18:1/23:1) (d18:1/22:2-OH)/TG, PC 18:2/18:2/TG, and CE 16:1/Chol. (see Tables 18 and 19).

In a particularly preferred embodiment, the lipid-clinical concentration ratio whose increased is compared to the control GlcCer(d18:1/18:0)/apolipoprotein A-I(mg/dL) (see Table 20).

In yet another aspect the invention relates to a method of choosing an appropriate treatment of atherosclerosis or CVD and/or one or more of their complications, such as AMI or CVD death, in a subject, comprising determining in a sample from said subject the concentration of one or more lipid(s), wherein (an) increased or decreased concentration(s) in said sample, when compared to a control sample, is (are) indicative of said subject being in need of treatment or a change in, or supplementation of, an already administered treatment, wherein the one or more lipid(s) whose increase(s) in concentration is (are) compared to the control is (are) selected from:
Cer(d18:0/22:0), Cer(d18:0/24:0), Cer(d18:0/24:1), Cer(d18:1/16:0), Cer(d18:1/18:0), Cer(d18:1/20:0), Cer(d18:1/24:1), GlcCer(d18:1/16:0), GlcCer(d18:1/18:0), LacCer(d18:1/18:0), LacCer(d18:1/20:0), LacCer(d18:1/22:0), LacCer(d18:1/24:1), Total LacCer; LacCer(d18:1/24:0), Total Cer, GlcCer(d18:1/24:0), Total GlcCer and LacCer(d18:1/16:0);
and wherein the one or more lipid(s) whose decrease(s) in concentration is (are) compared to the control is (are) selected from:
CE 14:0, CE 16:0, CE 17:1, CE 20:3, PC 35:3 (PC O-34:3), Cer(d18:0/24:0), GD3-d18:1/16:0, PC 16:0/16:1, PC 37:5 (PC O-38:5), SM (d18:1/16:1) (d18:1/15:2-OH), SM (d18:1/18:1), SM (d18:1/23:1) (d18:1/22:2-OH), Total CE, Total GD3, Total PC 0, Total PC, PC 16:0/20:4, CE 18:0, Cer(d18:1/26:1), CE 15:0, SM (d18:1/15:0)(d18:1/14:1-OH), GM3-d18:1/18:0, PC 37:5 (PC O-36:5), GM3-d18:1/21:0, PC 16:0/18:2, Total PI, SM (d18:1/17:0) (d18:1/16:1-OH), Cer(d18:1/26:0), PC 18:0/20:5, PI 38:3, PC 40:5, GM2-d18:1/18:0, Total GM2, GD1-d18:1/16:0, PC 16:0/20:5, PC 16:0/22:5, PC 18:0/20:3, PC 16:0/22:6, PI 38:4, and PC 16:0/20:4 (see Tables 2, 5, 8 and 11).

In a preferred embodiment, the one or more lipid(s) whose increase in concentration is (are) compared to the control is (are) selected from:
Cer(d18:0/22:0), Cer(d18:0/24:0), Cer(d18:0/24:1), Cer(d18:1/16:0), Cer(d18:1/18:0), Cer(d18:1/24:1), GlcCer (d18:1/16:0), GlcCer(d18:1/18:0), LacCer(d18:1/18:0), LacCer(d18:1/20:0), LacCer(d18:1/22:0), and LacCer (d18:1/24:1).

In another preferred embodiment, the one or more lipid(s) whose decrease in concentration is (are) compared to the control is (are) selected from:

CE 16:0, CE 17:1, PC 35:3 (PC O-34:3), CE 14:0, CE 20:3, Total CE, Cer(d18:0/24:0), GD3-d18:1/16:0, PC 16:0/16: 1, PC 37:5 (PC O-38:5), SM (d18:1/18:1), SM (d18:1/23: 1) (d18:1/22:2-OH), SM (d18:1/16:1) (d18:1/15:2-OH), Total GD3, and Total PC (see Tables 14 and 15).

In a particularly preferred embodiment, the one or more lipid(s) whose increase in concentration is (are) compared to the control is (are) selected from:

Cer(d18:1/16:0), LacCer(d18:1/22:0), and LacCer(d18:1/24: 1);

and the one or more lipid(s) whose decrease in concentration is (are) compared to the control is (are) selected from:

CE 14:0 and CE 20:3 (see Table 20).

In an alternative embodiment the invention relates to a method of choosing an appropriate treatment of atherosclerosis or CVD and/or one or more of their complications, such as AMI or CVD death, in a subject, comprising determining in a sample from said subject one or more lipid-lipid ratio(s), wherein (an) increased or decreased lipid-lipid ratio(s) in said sample, when compared to a control sample, is (are) indicative of said subject being in need of treatment or a change in, or supplementation of, an already administered treatment, wherein the one or more lipid-lipid ratio(s) whose increase(s) is (are) compared to the control is (are) selected from:

CE 19:1/LPC 20:4, Cer(d18:1/16:0)/LPC 16:0, Cer(d18:1/16:0)/LPC 18:1, Cer(d18:1/16:0)/LPC 18:2, Cer(d18:1/16:0)/PC 16:0/20:4, Cer(d18:1/16:0)/PC 18:1/18:2, Cer (d18:1/16:0)/PC 33:2 (PC O-34:2), Cer(d18:1/16:0)/PC 35:3 (PC 0-36:3), Cer(d18:1/16:0)/PC 35:4 (PC O-36:4), Cer(d18:1/16:0)/PC 36:3, Cer(d18:1/16:0)/PC 36:4, Cer (d18:1/16:0)/PC 33:3 (PC O-34:3), Cer(d18:1/16:0)/SM (d18:1/18:0), Cer(d18:1/16:0)/SM (d18:1/23:0) (d18:1/22:1-OH), Cer(d18:1/16:0)/SM (d18:1/24:0) (d18:1/23:1-OH), Cer(d18:1/16:0)/SM (d18:1/24:1) (d18:1/23:2-OH), Cer(d18:1/16:0)/SM (d18:1/25:1) (d18:1/24:2-OH), Cer (d18:1/16:0)/Total CE, Cer(d18:1/16:0)/Total LPC, Cer (d18:1/16:0)/Total PC, Cer(d18:1/20:0)/LPC 18:2, Cer (d18:1/22:0)/LPC 18:2, Cer(d18:1/22:0)/PC 33:3 (PC O-34:3), Cer(d18:1/22:0)/SM (d18:1/24:0)(d18:1/23:1-OH), Cer(d18:1/24:1)/LPC 18:2, Cer(d18:1/24:1)/PC 33:3 (PC 0-34:3), Cer(d18:1/24:1)/SM (d18:1/23:0) (d18:1/22:1-OH), Cer(d18:1/24:1)/SM (d18:1/24:0) (d18:1/23:1-OH), Cer(d18:1/24:1)/SM (d18:1/25:1) (d18:1/24:2-OH), GlcCer(d18:1/16:0)/LPC 18:2, GlcCer(d18:1/18:0)/LPC 18:2, GlcCer(d18:1/26:1)/SM (d18:1/25:1) (d18:1/24:2-OH), LacCer(d18:1/18:0)/PC 36:4, LacCer(d18:1/22:0)/ PC 16:0/20:4, LacCer(d18:1/22:0)/PC 18:0/20:4, LacCer (d18:1/22:0)/PC 35:4 (PC 0-36:4), LacCer(d18:1/22:0)/ PC 36:4, LacCer(d18:1/22:0)/SM (d18:1/24:0) (d18:1/23:1-OH), LacCer(d18:1/22:0)/SM (d18:1/25:1) (d18:1/24:2-OH), LacCer(d18:1/22:0)/Total CE, LacCer(d18:1/24:1)/ PC 16:0/20:4, LacCer(d18:1/24:1)/PC 18:0/20:4, LacCer (d18:1/24:1)/PC 36:4, LacCer(d18:1/24:1)/Total CE, PC 38:0/PC 38:5, Cer(d18:1/16:0)/Cer(d18:1/26:0), DAG 16:1/16:1/PC 32:1, DAG 16:1/16:1/PI 38:4, GM3-d18:1/24:1/SM (d18:1/16:1) (d18:1/15:2-OH), GM3-d18:1/24: 1/SM (d18:1/18:1), GlcCer(d18:1/24:1)/SM (d18:1/23:1) (d18:1/22:2-OH), SM (d18:1/16:0) (d18:1/15:1-OH)/SM (d18:1/16:1) (d18:1/15:2-OH), PC 18:0/20:3/PC33:3(PC 0-34:3), GlcCer(d18:1/26:1)/LPC 18:2, LacCer(d18:1/24: 1)/Total CE, Cer(d18:1/24:1)/Total CE, LacCer(d18:1/22: 0)/Total CE, CE 22:2/LPC 20:4, Cer(d18:1/20:0)/SM (d18:1/23:0) (d18:1/22:1-OH), Cer(d18:1/22:0)/Total CE, LacCer(d18:1/18:0)/PC 40:7, GlcCer(d18:1/16:0)/SM (d18:1/24:0) (d18:1/23:1-OH), Cer(d18:1/24:1)/PC35:4 (PC O-36:4), Cer(d18:1/22:0)/SM (d18:1/23:0) (d18:1/22: 1-OH), Cer(d18:1/20:0)/Total CE, Cer(d18:1/16:0)/PC 36:2, Cer(d18:1/16:0)/PC 18:0/18:2, Cer(d18:1/22:0)/PC 40:7, Cer(d18:1/22:0)/PC 39:0 (PC O-40:0), GlcCer(d18: 1/18:0)/LPC 18:1, CE 20:0/PC 40:4, GlcCer(d18:1/16:0)/ PC 36:2, LacCer(d18:1/16:0)/PC 35:2 (PC O-36:2), PC 39:7 (PC O-40:7)/Total CE, PC 38:0/Total CE, PC 38:0/PC 35:6 (PC O-36:5), Total LacCer/Total PC O, SM (d18:1/ 14:0) (d18:1/13:1-OH)/SM (d18:1/23:0) (d18:1/22:1-OH), LPC 18:1/PC 32:1, Cer(d18:1/24:1)/PC 32:1, GM3-d18:1/24:1/SM (d18:1/23:1) (d18:1/22:2-OH), GM3-d18: 1/24:1/PC 32:1, DAG 16:1/16:1/PC 30:0, Cer(d18:1/24: 1)/SM (d18:1/18:1), GM3-d18:1/24:1/SM (d18:1/18:1), GM3-d18:1/24:1/SM (d18:1/16:1) (d18:1/15:2-OH), Cer (d18:1/16:0)/PC 32:1, LacCer(d18:1/16:0)/PC 40:6, Cer (d18:1/24:1)/PC 38:4, LPC 18:0/PC 32:1, Cer(d18:1/24: 1)/PC 34:2, GM3-d18:1/24:2/SM (d18:1/23:1) (d18:1/22: 2-OH), GM3-d18:1/24:2/PC 32:1, GM3-d18:1/24:1/PC 34:2, GlcCer(d18:1/16:0)/PC 32:1, GM3-d18:1/24:1/PC 36:4, GM3-d18:1/16:0/SM (d18:1/23:1) (d18:1/22:2-OH), GM3-d18:1/24:1/PC 34:1, Cer(d18:1/16:0)/PC 34:2, GlcCer(d18:1/16:0)/PC 34:2, GM3-d18:1/16:0/PC 32:1, Cer(d18:1/16:0)/PC 34:1, Cer(d18:1/24:1)/PC 34:3, GlcCer(d18:1/16:0)/PC 34:1, GM3-d18:1/18:0/PC 32:1, Cer(d18:1/16:0)/PC 34:3, GlcCer(d18:1/16:0)/PC 34:3, LPC 16:0/SM (d18:1/14:0) (d18:1/13:1-OH), GlcCer(d18: 1/20:0)/PC 34:3 and GlcCer(d18:1/18:0)/PC 34:3;

and wherein one or more lipid-lipid ratio(s) whose decrease is (are) compared to the control is (are) selected from:

LPC 20:4/PC 35:1 (PC O-36:1), CE 20:4/GlcCer(d18:1/26: 1), CE 16:1/Total LacCer, CE 22:6/LacCer(d18:1/22:0), CE 16:1/PC 37:2 (PC O-38:2), CE 16:0/GlcCer(d18:1/16: 0), CE 22:6/Cer(d18:1/16:0), CE 14:0/PC 37:2 (PC O-38: 2), CE 16:0/Total LacCer, CE 18:2/Cer(d18:1/16:0), CE 16:0/LacCer(d18:1/22:0), CE 20:4/GlcCer(d18:1/24:1), CE 18:1/GlcCer(d18:1/16:0), CE 20:4/GlcCer(d18:1/16: 0), CE 18:0/Cer(d18:1/16:0), LPC 20:4/PC 37:2 (PC O-38: 2), CE 16:0/Cer(d18:1/24:1), CE 17:1/LacCer(d18:1/22: 0), CE 18:2/GlcCer(d18:1/16:0), CE 22:6/GlcCer(d18:1/ 16:0), Total CE/Total LacCer, CE 14:0/Cer(d18:1/24:1), CE 20:4/LacCer(d18:1/16:0), CE 22:6/Total LacCer, CE 22:6/LacCer(d18:1/24:1), CE 18:1/Cer(d18:1/16:0), CE 16:1/Cer(d18:1/16:0), CE 16:1/LacCer(d18:1/22:0), CE 16:0/LacCer(d18:1/16:0), CE 16:1/CE 22:2, CE 16:1/Cer (d18:1/24:1), CE 22:6/LacCer(d18:1/18:0), CE 22:6/LacCer(d18:1/20:0), CE 20:4/LacCer(d18:1/22:0), CE 20:4/ Cer(d18:1/24:1), CE 16:1/CE 20:0, CE 20:4/Cer(d18:1/ 16:0), LPC 20:4/PC 37:2 (PC O-38:2), CE 20:4/Total GlcCer, CE 20:4/Total LacCer, CE 20:4/SM (d18:1/14:0) (d18:1/13:1-OH), LPC 20:4/PC 35:1 (PC O-36:1), CE 14:0/Cer(d18:1/16:0), CE 17:1/Cer(d18:1/16:0), CE 17:1/ Cer(d18:1/24:1), CE 20:4/GlcCer(d18:1/18:0), CE 16:0/ Cer(d18:1/16:0), CE 18:1/Cer(d18:1/24:1), CE 16:0/Cer (d18:1/24:1), CE 16:0/DAG 16:1/16:1, CE 16:1/CE 20:3, CE 16:1/DAG 16:1/16:1, CE 16:1/GM3-d18:1/24:1, CE 16:1/LPC 16:0, CE 18:2/Cer(d18:1/24:1), CE 18:2/DAG 16:1/16:1, CE 18:2/GlcCer(d18:1/24:1), CE 18:2/GM3-d18:1/24:1, CE 18:3/Cer(d18:1/24:1), CE 20:4/DAG 16:1/ 16:1, Cer(d18:0/22:0)/PE 36:2, Cer(d18:0/24:0)/Cer(d18: 1/16:0), Cer(d18:0/24:0)/DAG 16:1/16:1, Cer(d18:1/24: 0)/Cer(d18:1/24:1), GD3-d18:1/16:0/GlcCer(d18:1/24:1), GlcCer(d18:1/26:0)/GlcCer(d18:1/26:1), GM3-d18:1/18: 0/GlcCer(d18:1/24:1), GM3-d18:1/18:0/GM3-d18:1/24:

1, GM3-d18:1/20:0/GM3-d18:1/24:1, GM3-d18:1/21:0/ GM3-d18:1/24:1, GM3-d18:1/22:1/GM3-d18:1/24:1, GM3-d18:1/23:0/GM3-d18:1/24:1, PC 16:0/18:2/PE 36:2, PC 32:1/PC 36:1, PC 34:1/PE 36:2, PC 34:2/PE 36:2, PC 34:3/PE 36:2, PC 36:2/PE 36:2, SM (d18:1/16:1) (d18: 1/15:2-OH)/SM (d18:1/24:1)(d18:1/23:2-OH), SM (d18: 1/18:1)/SM (d18:1/24:1) (d18:1/23:2-OH), SM (d18:1/23: 1) (d18:1/22:2-OH)/SM (d18:1/24:1) (d18:1/23:2-OH), SM (d18:1/23:0) (d18:1/22:1-OH)/Total Cer, CE 18:2/Cer (d18:1/22:0), PC 36:4/PC 38:0, CE 18:2/Total Cer, CE 20:4/Cer(d18:1/22:0), CE 18:1/LacCer(d18:1/16:0), CE 18:1/GlcCer(d18:1/18:0), CE 18:1/LacCer(d18:1/22:0), Total CE/Total LacCer, CE 18:1/Total LacCer, CE 18:1/ LacCer(d18:1/24:1), CE 20:4/Cer(d18:1/24:1), LPC 18:2/ LacCer(d18:1/22:0), CE 20:4/Total LacCer, CE 17:1/Lac-Cer(d18:1/20:0), CE 20:4/LacCer(d18:1/24:1), CE 16:1/ GlcCer(d18:1/18:0), LPC 20:4/PC 38:0, GM3-d18:1/20:0/ GM3-d18:1/22:0, GM3-d18:1/22:1/GM3-d18:1/24:1, Cer (d18:1/26:0)/GlcCer(d18:1/16:0), GM3-d18:1/20:0/ GM3-d18:1/24:1, CE 18:2/GlcCer(d18:1/26:1), CE 18:3/ Cer(d18:1/16:0), CE 18:2/Cer(d18:1/24:1), GD3-d18:1/ 16:0/GM3-d18:1/24:1, Cer(d18:1/26:0)/GlcCer(d18:1/ 24:1), CE 16:1/LPC 16:0, CE 16:1/CE 20:3, CE 16:1/LPC 18:1, CE 16:1/DAG 16:1/16:1 and CE 16:1/LacCer(d18: 1/16:0) (see Tables 3, 6, 9 and 12).

In a preferred embodiment, the one or more lipid-lipid ratio(s) whose increase is (are) compared to the control is (are) selected from:

CE 19:1/LPC 20:4, Cer(d18:1/24:1)/LPC 18:2, Cer(d18:1/ 16:0)/LPC 18:2, PC 38:0/PC 38:5, LacCer(d18:1/24:1)/PC 16:0/20:4, GlcCer(d18:1/26:1)/SM (d18:1/24:2-OH) (d18:1/25:1), Cer(d18:1/16:0)/SM (d18:1/24:1) (d18:1/ 23:2-OH), Cer(d18:1/16:0)/PC 18:1/18:2, Cer(d18:1/16: 0)/PC 35:3 (PC O-34:3), GlcCer(d18:1/16:0)/LPC 18:2, LacCer(d18:1/22:0)/SM (d18:1/24:0) (d18:1/23:1-OH), LacCer(d18:1/22:0)/PC 35:4 (PC O-36:4), LacCer(d18:1/ 24:1)/Total CE, Cer(d18:1/16:0)/PC 36:3, Cer(d18:1/16: 0)/LPC 18:1, LacCer(d18:1/22:0)/PC 16:0/20:4, Cer(d18: 1/16:0)/Cer(d18:1/26:0), DAG 16:1/16:1/PC 32:1, GM3-d18:1/24:1/SM (d18:1/16:1) (d18:1/15:2-OH), GM3-d18: 1/24:1/SM (d18:1/18:1).

In another preferred embodiment, the one or more lipid-lipid ratio(s) whose decrease is (are) compared to the control is (are) selected from:

CE 16:0/Cer(d18:1/16:0), CE 18:2/Cer(d18:1/16:0), CE 20:4/GlcCer(d18:1/16:0), CE 18:1/Cer(d18:1/16:0), CE 22:6/Cer(d18:1/16:0), CE 16:1/PC 37:2 (PC O-38:2), CE 18:0/Cer(d18:1/16:0), CE 18:2/GlcCer(d18:1/16:0), CE 16:0/GlcCer(d18:1/16:0), LPC 20:4/PC 35:1 (PC O-36:1), Total CE/Total LacCer, CE 20:4/Cer(d18:1/24:1), CE 16:1/DAG 16:1/16:1, CE 18:2/Cer(d18:1/24:1), CE 18:2/ Cer(d18:1/16:0), Cer(d18:1/24:0)/Cer(d18:1/24:1), Cer (d18:0/24:0)/DAG 16:1/16:1, Cer(d18:0/24:0)/Cer(d18:1/ 16:0), GD3-d18:1/16:0/GlcCer(d18:1/24:1), GlcCer(d18: 1/26:0)/GlcCer(d18:1/26:1), GM3-d18:1/22:1/GM3-d18: 1/24:1, GM3-d18:1/20:0/GM3-d18:1/24:1, GM3-d18:1/ 18:0/GlcCer(d18:1/24:1), PC 16:0/18:2/PE 36:2, SM (d18:1/23:1) (d18:1/22:2-OH)/SM (d18:1/24:1) (d18:1/ 23:2-OH), CE 16:1/CE 20:3, CE 16:1/Cer(d18:1/16:0), and CE 16:1/LPC 16:0 (see Tables 16 and 17).

In a particularly preferred embodiment, the one or more lipid-lipid ratio(s) whose increase is (are) compared to the control is (are) selected from:

Cer(d18:1/16:0)/LPC 18:1, LacCer(d18:1/24:1)/Total CE, CE 19:1/LPC 20:4, and Cer(d18:1/16:0)/PC 36:3;

and the lipid-lipid ratio whose decrease is compared to the control is:

CE 20:4/Cer(18:1/24:1) (see Table 20).

In yet another embodiment the invention relates to a method of choosing an appropriate treatment of atherosclerosis or CVD and/or one or more of their complications, such as AMI or CVD death, in a subject, comprising determining in a sample from said subject one or more lipid-clinical concentration ratio(s), wherein (an) increased or decreased lipid-clinical concentration ratio(s) in said sample, when compared to a control sample, is (are) indicative of said subject being in need of treatment or a change in, or supplementation of, an already administered treatment, wherein the one or more lipid-clinical concentration ratio(s) whose increase is (are) compared to the control is (are) selected from:

Cer(d18:0/22:0)/apolipoprotein A-I (mg/dL), Cer(d18:0/22: 0)/apolipoprotein A-II (mg/dL), Cer(d18:0/22:0)/HDL cholesterol ester (mg/dL), Cer(d18:0/24:1)/apolipoprotein A-II (mg/dL), Cer(d18:0/24:1)/cholesterol ester (mg/dL), Cer(d18:0/24:1)/HDL cholesterol ester (mg/dL), Cer(d18: 1/16:0)/apolipoprotein A-I (mg/dL), Cer(d18:1/16:0)/apolipoprotein A-II (mg/dL), Cer(d18:1/16:0)/apolipoprotein B (mg/dL), Cer(d18:1/16:0)/apolipoprotein E (mg/dL), Cer(d18:1/16:0)/body mass index (kg/m2), Cer(d18:1/16: 0)/cholesterol ester (mg/dL), Cer(d18:1/16:0)/free cholesterol (mg/dL), Cer(d18:1/16:0)/HDL cholesterol (EDTA) (mg/dL), Cer(d18:1/16:0)/HDL cholesterol ester (mg/dL), Cer(d18:1/16:0)/HDL phospholipid (mg/dL), Cer(d18:1/ 16:0)/LDL phospholipid (mg/dL), Cer(d18:1/16:0)/phospholipid (mg/dL), Cer(d18:1/16:0)/total cholesterol (EDTA) (mg/dL), Cer(d18:1/22:0)/apolipoprotein A-I (mg/dL), Cer(d18:1/22:0)/apolipoprotein A-II (mg/dL), Cer(d18:1/24:1)/apolipoprotein A-I (mg/dL), Cer(d18:1/ 24:1)/apolipoprotein A-II (mg/dL), Cer(d18:1/24:1)/cholesterol ester (mg/dL), Cer(d18:1/24:1)/HDL cholesterol ester (mg/dL), Cer(d18:1/24:1)/total cholesterol (EDTA) (mg/dL), GlcCer(d18:1/16:0)/apolipoprotein A-I (mg/dL), GlcCer(d18:1/16:0)/apolipoprotein A-II (mg/dL), GlcCer (d18:1/16:0)/cholesterol ester (mg/dL), GlcCer(d18:1/18: 0)/apolipoprotein A-I (mg/dL), GlcCer(d18:1/18:0)/apolipoprotein A-II (mg/dL), GlcCer(d18:1/18:0)/cholesterol ester (mg/dL), GlcCer(d18:1/26:1)/apolipoprotein A-II (mg/dL), GlcCer(d18:1/26:1)/cholesterol ester (mg/dL), LacCer(d18:1/22:0)/apolipoprotein A-I (mg/dL), LacCer (d18:1/22:0)/apolipoprotein A-II (mg/dL), LacCer(d18:1/ 22:0)/cholesterol ester (mg/dL), LacCer(d18:1/22:0)/HDL cholesterol (EDTA) (mg/dL), LacCer(d18:1/22:0)/HDL cholesterol ester (mg/dL), LacCer(d18:1/22:0)/LDL free cholesterol (mg/dL), LacCer (d18:1/22:0)/total cholesterol (EDTA) (mg/dL), LacCer(d18: 1/24:1)/apolipoprotein A-I (mg/dL), LacCer(d18:1/24:1)/ apolipoprotein A-II (mg/dL), LacCer(d18:1/24:1)/ cholesterol ester (mg/dL), LacCer(d18:1/24:1)/HDL cholesterol ester (mg/dL), PC 18:0/20:3/VLDL apolipoprotein B (mg/dL), Total Cer/apolipoprotein A-I (mg/dL), Total Cer/apolipoprotein A-II (mg/dL), Total LacCer/apolipoprotein A-I (mg/dL), Total LacCer/apolipoprotein A-II (mg/dL), DAG 16:1/16:1/HDL, GM3-d18:1/24:2/HDL, GlcCer(d18: 1/26:1)/HDL, Cer(d18:1/24:1)/LDL, GM3-d18:1/16:0/ HDL, Cer(d18:1/24:1)/Chol, Cer(d18:1/16:0)/Chol, Cer(d18:1/24: 1)/HDL, GM3-d18:1/24:1/HDL, GlcCer(d18:1/24:1)/HDL, Cer(d18:1/16:0)/HDL, Cer(d18:1/16:0)/apolipoprotein A-II (mg/dL), LacCer(d18:1/24:1)/apolipoprotein E (mg/dL), Cer (d18:1/24:1)/HDL cholesterol ester (mg/dL), LacCer(d18:1/ 22:0)/HDL cholesterol ester (mg/dL), LacCer(d18:1/24:0)/ HDL cholesterol ester (mg/dL), LacCer(d18:1/24:0)/ apolipoprotein C-II (mg/dL), GlcCer(d18:1/16:0)/HDL cholesterol ester (mg/dL), LacCer(d18:1/24:1)/apolipoprotein A-I (mg/dL), Total LacCer/HDL cholesterol ester (mg/dL), Cer(d18:1/22:0)/apolipoprotein A-II (mg/dL), LacCer (d18:1/22:0)/HDL cholesterol (EDTA) (mg/dL), Cer(d18:1/20:0)/apolipoprotein A-I (mg/dL), LacCer(d18:1/24:0)/HDL cholesterol (EDTA) (mg/dL), LacCer(d18:1/18:0)/LDL cholesterol (EDTA) (mg/dL), Cer(d18:1/22:0)/apolipoprotein A-I (mg/dL), GlcCer(d18:1/18:0)/apolipoprotein A-I (mg/dL), LacCer(d18:1/16:0)/HDL cholesterol ester (mg/dL), Cer(d18:1/24:1)/cholesterol ester (mg/dL), Total LacCer/apolipoprotein A-I (mg/dL), Cer(d18:1/20:0)/HDL phospholipid (mg/dL), Total LacCer/cholesterol ester (mg/dL), LacCer(d18:1/24:1)/LDL cholesterol ester (mg/dL), Cer(d18:1/24:1)/total cholesterol (EDTA) (mg/dL), GlcCer(d18:1/24:0)/apolipoprotein A-I (mg/dL), LacCer(d18:1/24:1)/LDL cholesterol (EDTA) (mg/dL), Cer(d18:1/24:1)/LDL phospho lipid (mg/dL), Total GlcCer/apolipoprotein A-I (mg/dL), LacCer(d18:1/24:1)/LDL free cholesterol (mg/dL), Cer(d18:1/22:0)/cholesterol ester (mg/dL), LacCer(d18:1/24:1)/apolipoprotein B (mg/dL), Cer(d18:1/22:0)/LDL cholesterol (EDTA) (mg/dL), Total Cer/cholesterol ester (mg/dL), LacCer(d18:1/16:0)/cholesterol ester (mg/dL), Cer(d18:1/22:0)/total cholesterol (EDTA) (mg/dL), LacCer(d18:1/24:1)/HDL free cholesterol (mg/dL), Total LacCer/LDL cholesterol ester (mg/dL), Total LacCer/LDL cholesterol (EDTA) (mg/dL), Total Cer/total cholesterol (EDTA) (mg/dL), Total LacCer/phospholipid (mg/dL), GlcCer(d18:1/20:0)/cholesterol ester (mg/dL), Total LacCer/HDL free cholesterol (mg/dL), Total LacCer/apolipoprotein B (mg/dL), LacCer(d18:1/16:0)/LDL cholesterol ester (mg/dL), Total LacCer/LDL phospholipid (mg/dL), LacCer(d18:1/16:0)/LDL cholesterol (EDTA) (mg/dL), GlcCer(d18:1/24:1)/HDL, DAG 16:1/16:1/HDL, Cer (d18:1/24:1)/LDL, Cer(d18:1/24:1)/Chol, and Cer(d18:1/16:0)/Chol;

and wherein the one or more lipid-clinical concentration ratio(s) whose decrease is (are) compared to the control is (are) selected from:

CE 14:0/free fatty acids (mmol/L), CE 16:0/apolipoprotein C-III (mg/dL), CE 17:1/apolipoprotein C-III (mg/dL), CE 17:1/free fatty acids (mmol/L), CE 17:1/free glycerol (mg/dL), CE 18:0/apolipoprotein C-III (mg/dL), CE 18:1/apolipoprotein C-III (mg/dL), CE 18:2/apolipoprotein C-III (mg/dL), CE 20:3/free fatty acids (mmol/L), CE 20:4/apolipoprotein C-III (mg/dL), CE 20:4/free fatty acids (mmol/L), LPC 18:2/apolipoprotein C-III (mg/dL), PC 18:1/18:2/apolipoprotein C-III (mg/dL), PC 39:0 (PC O-40:0)/free fatty acids (mmol/L), PC 40:7/free fatty acids (mmol/L), SM (d18:1/23:0) (d18:1/22:1-OH)/apolipoprotein C-III (mg/dL), SM (d18:1/23:0) (d18:1/22:1-OH)/free fatty acids (mmol/L), SM (d18:1/25:1) (d18:1/24:2-OH)/free fatty acids (mmol/L), Total CE/apolipoprotein C-III (mg/dL), CE 14:0/TG, CE 16:0/TG, CE 16:1/Chol, CE 16:1/TG, CE 18:0/TG, CE 18:2/TG, CE 18:3/TG, CE 20:4/TG, Cer(d18:0/22:0)/TG, Cer(d18:0/24:0)/TG, Cer(d18:0/24:1)/TG, Cer(d18:1/24:0)/TG, Cer(d18:1/26:0)/TG, DAG 18:1/18:2/TG, GD1-d18:1/16:0/TG, GD3-d18:1/16:0/TG, GM3-d18:1/18:0/TG, GM3-d18:1/21:0/TG, LacCer(d18:1/22:0)/TG, PC 16:0/16:1/TG, PC 16:0/18:1/TG, PC 16:0/18:2/TG, PC 16:0/20:4/TG, PC 16:0/22:5/TG, PC 16:0/22:6/TG, PC 18:0/18:2/TG, PC 18:0/20:3/TG, PC 18:2/18:2/TG, PC 30:0/TG, PC 32:1/TG, PC 34:1/TG, PC 34:2/TG, PC 34:3/TG, PC 35:2/TG, PC 36:2/TG, PC 36:4/TG, PC 38:3/TG, PC 38:4/TG, PC 40:6/TG, PC 35:2 (PC O-36:2)/TG, PI 36:2/TG, PI 38:3/TG, PI 38:4/TG, SM (d18:1/14:0) (d18:1/13:1-OH)/TG, SM (d18:1/16:1) (d18:1/15:2-OH)/TG, SM (d18:1/17:0) (d18:1/16:1-OH)/TG, SM (d18:1/18:1)/TG, SM (d18:1/23:1) (d18:1/22:2-OH)/TG, SM (d18:1/24:0) (d18:1/23:1-OH)/TG, CE 20:4/apolipoprotein C-III (mg/dL), CE 14:0/apolipoprotein C-III (mg/dL), CE 20:4/free fatty acids (mmol/L), LPC 20:4/free fatty acids (mmol/L), Total PC 0/C-reactive protein (mg/dL), Cer(d18:1/24:0)/Chol, CE 18:0/LDL, CE 18:2/LDL, Cer (d18:1/26:0)/Chol, CE 18:2/Chol, CE 20:5/LDL, CE 18:3/Chol, CE 20:5/Chol, PE 38:5/TG, CE 17:0/TG, CE 16:1/Chol, Cer(d18:1/22:0)/TG, PE 38:4/TG, Cer(d18:1/18:0)/TG, CE 22:6/TG, CE 15:0/TG, DAG 18:1/18:2/TG, PC 18:0/20:5/TG, PC 32:0/TG, CE 16:0/TG, Cer(d18:1/24:0)/TG, CE 20:5/TG, PC 40:6/TG, GM3-d18:1/21:0/TG, SM (d18:1/24:0) (d18:1/23:1-OH)/TG, PC 35:2 (PC O-36:2)/TG, CE 18:3/TG, PC 35:2 (PC O-34:2)/TG, PC 16:0/20:5/TG, CE 18:2/TG, CE 18:0/TG, PC 16:0/18:2/TG, PC 16:0/22:6/TG, CE 14:0/TG, PC 34:1/TG, SM (d18:1/17:0) (d18:1/16:1-OH)/TG, PC 36:5/TG, PC 38:3/TG, PC 18:0/20:3/TG, SM (d18:1/14:0) (d18:1/13:1-OH)/TG, PC 34:2/TG, SM (d18:1/23:1) (d18:1/22:2-OH)/TG, CE 16:1/TG, PC 18:2/18:2/TG and PC 32:1/TG (see Tables 4, 7, 10 and 13).

In a preferred embodiment, the one or more lipid-clinical concentration ratio(s) whose increase is (are) compared to the control is (are) selected from:
Cer(d18:0/22:0)/apolipoprotein A-I (mg/dL), Cer(d18:0/24:1)/cholesterol ester (mg/dL), Cer(d18:1/16:0)/apolipoprotein A-I (mg/dL), Cer(d18:1/24:1)/apolipoprotein A-I (mg/dL), GlcCer(d18:1/16:0)/apolipoprotein A-I (mg/dL), GlcCer(d18:1/18:0)/apolipoprotein A-I (mg/dL), LacCer (d18:1/22:0)/apolipoprotein A-I (mg/dL), LacCer(d18:1/22:0)/HDL cholesterol ester (mg/dL), Cer(d18:1/24:1)/HDL cholesterol ester (mg/dL), LacCer(d18:1/22:0)/total cholesterol (EDTA) (mg/dL), Cer(d18:1/24:1)/total cholesterol (EDTA) (mg/dL), Cer(d18:1/16:0)/apolipoprotein A-II (mg/dL), Cer(d18:1/22:0)/apolipoprotein A-II (mg/dL), LacCer(d18:1/24:1)/apolipoprotein A-I (mg/dL), Cer(d18:1/16:0)/HDL, Cer(d18:1/24:1)/HDL, DAG 16:1/16:1/HDL, GlcCer(d18:1/24:1)/HDL, GlcCer(d18:1/26:1)/HDL, GM3-d18:1/16:0/HDL, GM3-d18:1/24:1/HDL, Cer (d18:1/24:1)/Chol, and GM3-d18:1/24:2/HDL.

In another preferred embodiment, the one or more lipid-clinical concentration ratio(s) whose decrease is (are) compared to the control is (are) selected from:
LPC 18:2/apolipoprotein C-III (mg/dL), SM (d18:1/25:1) (d18:1/24:2-OH)/free fatty acids (mmol/L), CE 18:2/apolipoprotein C-III (mg/dL), CE 20:4/apolipoprotein C-III (mg/dL), Cer(d18:0/24:0)/TG, DAG 18:1/18:2/TG, PC 18:0/20:3/TG, CE 18:2/TG, SM (d18:1/18:1)/TG, Cer (d18:1/24:0)/TG, PI 38:3/TG, GD3-d18:1/16:0/TG, LacCer(d18:1/22:0)/TG, GM3-d18:1/21:0/TG, GD1-d18:1/16:0/TG, GM3-d18:1/18:0/TG, PC 16:0/18:2/TG, CE 16:1/TG, SM (d18:1/14:0) (d18:1/13:1-OH)/TG, SM (d18:1/23:1) (d18:1/22:2-OH)/TG, PC 18:2/18:2/TG, and CE 16:1/Chol. (see Tables 18 and 19).

In a particularly preferred embodiment, the lipid-clinical concentration ratio whose increase is compared to the control is: GlcCer(d18:1/18:0)/apolipoprotein A-I(mg/dL) (see Table 20).

In one embodiment of the invention, the treatment the effectiveness of which is to be evaluated or which is to be chosen as appropriate in accordance with the methods described and claimed herein, is a lipid modifying treatment.

For the purposes of the invention, at least one lipid concentration, lipid-lipid ratio or lipid-clinical concentration ratio from Tables 2-7 or 14-20, or combinations thereof, may be determined to assess whether the patient is at risk to develop, or suffering from atherosclerosis or cardiovascular disease (CVD) and/or one or more of their complications such as AMI or CVD death; to evaluate the effectiveness of the treatment of atherosclerosis or CVD and/or one or more of their complications, such as AMI or CVD death in a subject; or to choose an appropriate treatment of atherosclerosis or CVD and/or one or more of their complications, such as AMI or CVD death in a subject. However, it is also possible, and may be advantageous, to determine at least 2, at least 3, at least 4, at least 5, at least 6, at least 7, or at least 8 lipid concentrations, lipid-lipid ratios or lipid-clinical concentration ratios from Tables 2-7 or 14-20, or combinations thereof, in this regard. Where more than one lipidomic markers are determined and used for the assessment, it may be advantageous that a specific lipid concentration, lipid-lipid ratio, lipid-clinical concentration ratio or combination thereof, is given greater weight than others in the above-mentioned assessment, evaluation or choice.

Preferred embodiments of the invention are methods wherein the one or more lipid(s) or lipid ratio(s), or combination thereof, comprise(s) Cer(d18:1/16:0), LacCer(d18:1/22:0), LacCer(d18:1/24:1), CE 14:0, CE 20:3, Cer(d18:1/16:0)/LPC 18:1, LacCer(d18:1/24:1)/Total CE, CE 19:1/LPC 20:4, Cer(d18:1/16:0)/PC 36:3, CE 20:4/Cer(d18:1/24:1) and/or GlcCer(d18:1/18:0)/apolipoprotein A-I (mg/dL)) (see Table 20).

In the context of the present invention, CVD is typically characterized by coronary artery disease, peripheral artery disease, a stroke and/or CVD death. The CVD in the subject whose sample is analyzed in accordance with the invention may be atherosclerosis-induced. However, the invention also embodies methods involving subjects who are at risk of developing CVD, but who may or may not have atherosclerosis.

In a further embodiment, the methods of the invention may further comprise determining the serum level of total cholesterol, low-density lipoprotein cholesterol (LDL-C), high-density lipoprotein cholesterol (HDL-C), Apolipoprotein B (ApoB) and/or Apolipoprotein C-III in the subject's sample. In one embodiment of the invention, the subject does not have elevated serum levels of one or more of total cholesterol, low-density lipoprotein cholesterol (LDL-C), Apolipoprotein C-III or Apolipoprotein B (ApoB), or a decreased serum level of HDL-cholesterol (HDL-C).

As mentioned above, for the purposes of the present invention, a control sample may be taken from a healthy individual or created from a generalized population of healthy individuals, e.g., by mixing a variety of samples from said population. A healthy individual or a generalized population of healthy individuals means that none of these individuals have suffered from severe atherosclerosis or CVD. If a generalized population is used then several lipid profiles from a population are combined and the lipidomic marker is created from this combination. The control sample may alternatively be taken from (a) CAD patient(s) that has/have remained free of any major CVD complications or a group of CAD patients that has remained free of any major CVD complications. The levels or amounts of the individual lipids or the lipid-lipid ratios or lipid-clinical concentration rations in the sample from a subject are compared to the levels or amounts of the lipids or lipid ratios in the control for determining the risk of atherosclerosis or CVD and/or one or more of their complications, such as AMI or CVD death, in said subject.

The invention encompasses the analysis of lipid concentrations, lipid-lipid ratios and/or lipid-clinical concentration ratios in samples from a subject that has been or is being treated with one or more statins and/or any other HMG-CoA reductase inhibitor.

Alternatively, the invention encompasses the analysis of lipid concentrations, lipid-lipid ratios and/or lipid-clinical concentration ratios in samples from a subject that has not yet undergone statin therapy or therapy with any other HMG-CoA reductase inhibitor.

In accordance with the aspects and embodiments of the invention described and claimed herein, the statin may be one selected from the group consisting of atorvastatin, cerivastatin, fluvastatin, fluvastatin XL, lovastatin, pitavastatin, pravastatin, rosuvastatin, and simvastatin.

Collecting information on a lipidomic marker or a lipidomic profile from a subject's biological sample can be performed via various chemical and high resolution analytical techniques. Suitable analytical techniques include but are not limited to mass spectrometry and nuclear resonance spectroscopy. Any high resolution technique capable of resolving individual lipids or lipid classes and providing structural information of the same can be used to collect the lipid profile from the biological sample. For methods of the present invention the level of the lipid is determined by using mass spectrometry, nuclear magnetic resonance spectroscopy, fluorescence spectroscopy or dual polarisation interferometry, a high performance separation method such as HPLC or HPLC and/or an immunoassay such as an ELISA. According to an alternative or further embodiment an analyte in a sample can be detected and/or quantified by combining the analyte with a binding moiety capable of specifically binding the analyte. The binding moiety can include, for example, a member of a ligand-receptor pair, i.e., a pair of molecules capable of having a specific binding interaction. The binding moiety can also include, for example, a member of a specific binding pair, such as antibody-antigen, enzyme-substrate, nucleic acid-based ligands, other protein ligands, or other specific binding pairs known in the art. In a preferred embodiment, the lipidomic profile is collected with mass spectrometry (MS), wherein the MS instrument may be coupled to direct infusion methods and high performance separation methods such as HPLC or HPLC. The amount of the individual lipids or lipid classes in the collected lipidomic profile is used when comparing the collected lipid profile to a control.

The methods of the present invention may be used for determining a risk of said patient to develop CVD, determining early warning signs of CVD in said patient, determining or predicting the occurrence of atherosclerosis in a patient and/or predicting and/or diagnosing CVD and/or CVD complications including death, myocardial infarction (MI), angina pectoris, transischemic attack (TIA) and stroke.

In one embodiment of the invention, a method for treating or preventing atherosclerosis or CVD and/or one or more of their complications, such as AMI or CVD death, in a subject in need thereof is provided. The method comprises administering a therapeutically effective dose of a drug capable of modulating one or more of the lipid concentration(s), lipid-lipid ratio(s) or lipid-clinical concentration ratio(s) described in Tables 2-7 or 14-20, wherein the dose is such that said one or more lipid concentration(s), lipid-lipid ratio(s) or lipid-clinical concentration ratio(s) in a sample of said subject does not significantly change when compared to (a) corresponding lipid concentration(s), (a) corresponding lipid-lipid ratio(s) or (a) corresponding lipid-clinical concentration ratio(s) in a control, e.g., a control sample. In a preferred embodiment, the drug is a statin or another HMG CoA reductase inhibitor. Particularly preferred statins in this regard are atorvastatin, cerivastatin, fluvastatin, fluvastatin XL, lovastatin, pitavastatin, pravastatin, rosuvastatin or simvastatin. In another preferred embodiment, the drug is niacin (nicotinic acid); a cholesterol absorption inhibitor, such as ezetimibe or SCH-48461; a cholesteryl ester transfer protein (CETP) inhibitor, such as torcetrapib, anacetrapib or JTT-705; a bile acids sequestrant, such as colesevelam, cholestyramine and colestipol; or a fibrate, such as fenofibrate, gemfibrozil, clofibrate, and bezafibrate. Alternatively, it may also be a phytosterol.

Also embodied by the present invention is a lipid as described herein, e.g. a lipid from any of Tables 2, 5, 14, 15 or 20, for use in preventing or treating a subject at risk to develop or suffering from atherosclerosis or CVD and/or one or more of their complications such as AMI or CVD death, wherein the said lipid is to be taken as a dietary supplement or a medicament. A corresponding method of treatment is likewise encompassed. Likewise, the invention also encompasses a modulator for use for modulating a lipid concentration, lipid-lipid ratio or lipid-clinical concentration ratio as described herein, e.g., in Tables 2-7 or 14-20, in a subject at risk to develop, or suffering from atherosclerosis or CVD and/or one or more of their complications such as AMI or CVD death. A corresponding method of treatment is likewise encompassed. In a further embodiment, the said modulator is a small molecule, an antisense RNA, a small interfering RNA (siRNA) or a natural or modified lipid.

In one embodiment of the present invention, an antibody against any one of the lipids in Tables 2-7 or 14-20 is used for predicting and/or diagnosing atherosclerosis or CVD and/or one or more of their complications such as AMI or CVD death. In another embodiment of the invention, the antibody may be used for preventing or treating atherosclerosis or CVD and/or one or more of the above complications in a subject.

Any of the methods, drugs, lipids or antibodies of the present invention may be used for a subject which has suffered from a cardiovascular disease event such as angina pectoris, myocardial infarction and cardiovascular death.

Also encompassed by the present invention is a kit for predicting or detecting atherosclerosis or CVD or for performing any of the methods or uses of the present invention, wherein the kit comprises a lipid standard chosen from the lipids in Tables 2 or 5, or one of the lipids of Tables 2, 5, 14, 15 or 20, one or more control lipidomic markers, and optionally an antibody against one of the said lipids, and further optionally reagents for performing the methods or uses. In a preferred embodiment, the kit is used to predict or detect atherosclerosis or CVD, or to perform any of the methods encompassed by the present invention, wherein the lipid concentration(s), lipid ratio(s) or lipid-clinical concentration ratio(s) in a sample from a subject is (are) determined by using mass spectrometry. The one or more control marker(s) of the kit of the present invention may be, for example, (a) lipid(s) or (a) protein(s). One preferred embodiment is wherein the one or more control marker(s) of the claimed kit is/are (a) molecule(s) that is/are regularly measured in a clinical setting. For example, preferred are embodiments wherein the one more said control marker(s) is apoA, apoB, albumin or total PC, or a combination thereof.

DETAILED DESCRIPTION OF THE INVENTION

Definitions

Figure 1:
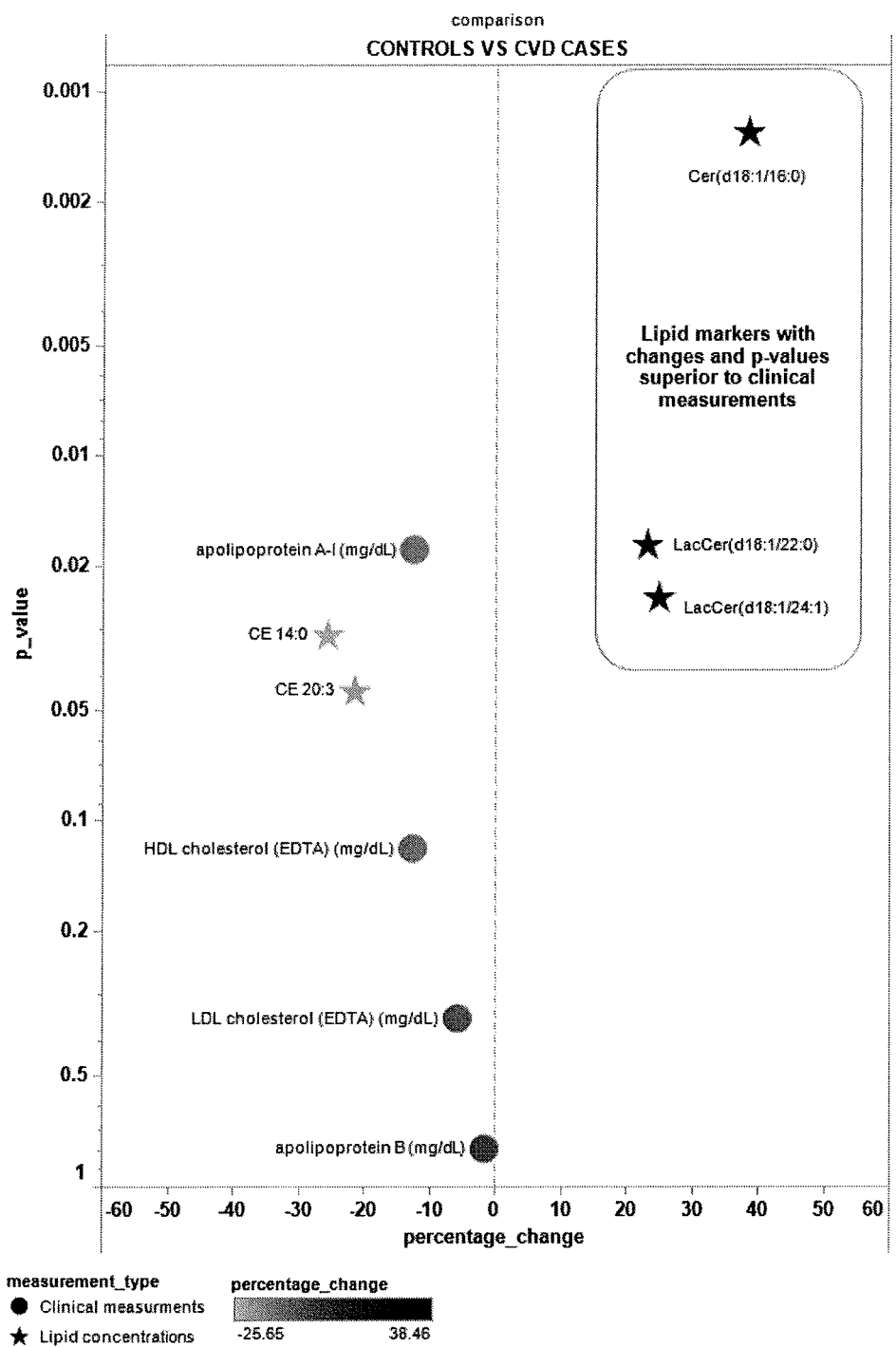
FIG. 1. Comparison of molecular lipid concentrations and traditional CVD biomarkers in control subjects and CVD patients. X-axis indicates the percentage change of a given lipid between cases and controls. Y-axis indicates the respective p-value for the change. The traditional biomarkers, such as LDL cholesterol, HDL cholesterol, apoB, apoA1, total cholesterol, are marked as filled circles. The quantified molecular lipids are marked as stars. The data shows that several molecular lipid markers are superior to traditional clinical markers.

Coronary vascular disease/cardiovascular disease (CVD) has its general meaning in the art and is used to classify numerous conditions that affect the heart, heart valves, blood, and vasculature of the body. Cardiovascular diseases include endothelial dysfunction, coronary artery disease, angina pectoris, myocardial infarction, atherosclerosis, congestive heart failure, hypertension, cerebrovascular disease, stroke, transient ischemic attacks, deep vein thrombosis, peripheral artery disease, cardiomyopathy, arrhythmias, aortic stenosis, and aneurysm. Such diseases frequently involve atherosclerosis. In a preferred embodiment of the invention, the cardiovascular disease is a cardiovascular disease associated with atherosclerosis.

CAD is coronary artery disease, AMI is acute myocardial infarction, ACS is acute coronary syndrome, CAC is coronary artery calcification, RCT is reverse cholesterol transport, LDL is low density lipoprotein, HDL is high density lipoprotein, LDL-C is low density lipoprotein cholesterol, HDL-C is high density lipoprotein cholesterol, ApoA is Apolipoprotein A, ApoB is Apolipoprotein B, ApoC is apolipoprotein C, MS is mass spectrometry, HPLC is high performance liquid chromatography, and HPLC is ultra performance liquid chromatography.

As used herein, "a subject" includes all mammals, including without limitation humans, but also non-human primates, dogs, cats, horses, sheep, goats, cows, rabbits, pigs and rodents.

A "sample" is defined as any biological sample obtained from a subject or a group or population of subjects. For the purposes of the present invention, the biological sample may be whole blood, blood serum, or blood plasma. It may also be a tissue sample. However, a preferred embodiment is wherein the biological sample is plasma or serum. Taking a blood sample of a patient is a part of normal clinical practice. The blood sample can be taken in connection with e.g. measuring the cholesterol levels in the patients. The collected blood sample can be prepared and serum or plasma can be separated with techniques well known to a person skilled in the art. Vena blood samples can be collected from patients using a needle and a BD Vacutainer® Plastic Tubes or Vacutainer® Plus Plastic Tubes (BD Vacutainer® SST™ Tubes contain spray-coated silia and a polymer gel for serum separation). Serum can be separated by centrifugation at 1300 RCF for 10 min at room temperature and stored in small plastic tubes at −80° C.

For the purposes of the present invention, lipids from the Lipidomic analysis were named according to the following nomenclature: CE is cholesteryl ester, Cer is ceramide, DAG is diacylglycerol, PC 0 is ether-linked PC, GD is disialogangliosides, GlcCer is galactosyl- and glucosylceramides, GM is monosialogangliosides, LacCer is lactosylceramides, LPC is lysophosphatidylcholine, PC is Phosphatidylcholine, PE is Phosphatidylethanolamine, PI is Phosphatidylinositol, SM is Sphingomyelin, S1P is sphingosine-1-phosphate.

The nomenclature X:Y indicates, X number of total carbon atoms in the fatty acid(s) portions of the molecule, and Y the total number of double bonds in the fatty acid portion(s) of the molecule.

The nomenclature A/B indicates, for a molecule of DAG and PC, A and B types of fatty acid moieties attached to the glycerol backbone of the molecule.

The nomenclature (dC/A) indicates, for a molecule of Cer, GD, GlcCer, GM, LacCer and SM, C the type of long-chain base with an amide-linked, A, fatty acid moiety.

For a molecule of GD and GM, the following number (e.g. GM2 and GM3) characterizes the carbohydrate sequence.

The wording "compared to a control sample" as used herein will be understood to include embodiments where control samples are actually analyzed in respect of a lipidomic marker of interest, i.e., in respect of the concentration of one or more of the lipid(s), the lipid-lipid ratios, or the lipid-clinical concentration ratios or combinations thereof as specifically described herein in connection with the various aspects and embodiments of the present invention. It will be appreciated, however, that the above wording also includes embodiments where the corresponding information on said lipidomic marker in said control sample is merely taken from the literature, or has been previously determined, calculated or extrapolated, or is yet to be determined, calculated or extrapolated.

As used herein, the term "antibody" includes monoclonal and polyclonal antibodies, whole antibodies, antibody fragments, and antibody sub-fragments that exhibit specific binding to a said lipid. Thus, suitable "antibodies" can be whole immunoglobulins of any class, e.g., IgG, IgM, IgA, IgD, IgE, chimeric antibodies or hybrid antibodies with dual or multiple antigen or epitope specificities, or fragments, e.g., $F(ab')_2$, Fab', Fab and the like, including hybrid fragments, and additionally includes any immunoglobulin or any natural, synthetic or genetically engineered protein that acts like an antibody by binding to a specific antigen to form a complex. The term "antibody" encompasses antigen-binding fragments of antibodies (e.g., single chain antibodies, Fab fragments, $F(ab')_2$, a Fd fragment, a Fv fragment and dAb fragments) as well as complete antibodies. For example, Fab molecules can be expressed and assembled in a genetically transformed host like *E. coli*. A lambda vector system is available thus to express a population of Fab's with a potential diversity equal to or exceeding that of subject generating the predecessor antibody. See Huse W D, et al., *Science* 1989, 246:1275-81. Such Fab' s are included in the definition of "antibody." The ability of a given molecule, including an antibody fragment or sub-fragment, to act like an antibody and specifically bind to a specific antigen can be determined by binding assays known in the art, for example, using the antigen of interest as the binding partner.

Antibodies against lipids in accordance with the present invention may be prepared by methods well known to those skilled in the art. For example, mice may be immunized with a lipid with adjuvant. Splenocytes are harvested as a pool from the mice that were administered 3 immunizations at 2-week intervals with test bleeds performed on alternate weeks for serum antibody titers. Splenocytes are prepared as 3 aliquots that are either used immediately in fusion experiments or stored in liquid nitrogen for use in future fusions.

Fusion experiments are then performed according to the procedure of Stewart & Fuller, *J. Immunol. Methods* 1989, 123:45-53. Supernatants from wells with growing hybrids are screened by enzyme-linked immunosorbent assay (ELISA) for monoclonal antibody (MAb) secretors on 96-well ELISA plates coated with the said lipid. ELISA positive cultures are cloned by limiting dilutions, typically resulting in hybridomas established from single colonies after 2 serial cloning experiments.

EXAMPLES

Example 1

Materials and Methods

1) The Ludwigshafen Risk and Cardiovascular Health (LURIC) study is an ongoing prospective study of currently >3800 individuals of German ancestry in whom the cardiovascular and metabolic phenotypes CAD, MI, dyslipidaemia, hypertension, metabolic syndrome and diabetes mellitus have been defined or ruled out using standardised methodologies in all study participants.

From 1997 to 2002 about 3800 patients were recruited at the cardiac centre in Ludwigshafen.

Inclusion criteria for LURIC were:
German ancestry (limitation of genetic heterogeneity)
clinical stability (except for acute coronary syndromes: ACS)
availability of a coronary angiogram
Exclusion criteria were:
any acute illness other than ACS
any chronic disease where non-cardiac disease predominated
a history of malignancy within the last five years After written informed consent baseline examination was done consisting of a standardized individual and family history questionnaire and extensive sampling of fasted venous blood in the early morning. To all individuals without known diabetes mellitus and insulin therapy an oral glucose tolerance test was offered. Blood samples from patients have been and will be used for biochemical and molecular genetic analyses.

The LURIC study aims to provide a well-defined resource for the study of environmental and genetic risk factors and their interactions as well as the study of functional relationships between gene variation and biochemical phenotype (functional genomics) or response to medication (pharmacogenomics). The ongoing long-term follow-up on clinical events allows studying the prognostic importance of common genetic variants (polymorphisms) and plasma biomarkers.

In the current biomarker study the inventors compared extreme diseased cases with controls, a total of 58 subjects. Subjects with minimal atherosclerosis level in the angiogram and no cardiovascular events during the follow-up were used as controls, while the case group had severe atherosclerosis based on the angiography at baseline and in addition they died during the follow-up due to acute cardiovascular events. Lipid lowering drug users were excluded from both groups in order to allow an unbiased lipidomic comparison between these two groups. LURIC study allows to compare subjects that do not have elevated serum levels of known lipid biomarkers including total cholesterol, low-density lipoprotein cholesterol (LDL-C) and/or Apolipoprotein B (ApoB). The subject selection is described in Table 1.

TABLE 1

Background characteristics for LURIC patients analyzed with lipidomics

| Variable | Controls (n = 40) | Cases (n = 18) |
|---|---|---|
| Age (average) | 64.5 | 65.2 |
| LDL-C (mg/dL) | 123 | 114 |
| HDL-C (mg/dL) | 42 | 37 |
| DM2 patients | 7 | 10 |
| Smokers (active or quit less than 3 years before sampling) | 5 | 4 |

Definition of Cases: All cases had a significant two (n=3) or three (n=15) vessel disease (>50% stenosis) in coronary angiogram and they all died due to CVD during the follow-up.

Definition of Controls: No clinically significant atherosclerosis in coronary angiograms (max stenosis %<=10%). No CVD events during the follow-up.

2) In the Sahlgrenska Hospital Atherosclerotic Plaque Study (SHAPS) 12 surgically removed carotid artery plaques and plasma samples obtained from the same individual were analyzed. Plasma samples from control subjects free of clinical atherosclerotic disease were analyzed as control samples.

Example 2

Analytical Methods
Mass Spectrometry Driven Lipidomics

Direct infusion coupled to tandem mass spectrometry, i.e. shotgun lipidomics, and two liquid chromatography tandem mass spectrometry (LC-MS/MS) approaches, i.e. ceramide and cerebroside lipidomics and ganglioside lipidomics, were used to identify lipid biomarkers for coronary artery disease (CVD) risk by analyzing molecular lipid species in human serum, plasma, and carotid artery plaques. The applied methods were optimized especially for quantification of molecular cholesteryl esters (CE), phosphatidylcholines (PC), lysophosphatidylcholines (LPC) and other lysophospholipids (LPL), ether-linked phosphatidylcholines (PC O) and other ether-linked phospholipids (PL O), phosphatidylserines (PS), phosphatidylethanolamines (PE), phosphatidylglycerols (PG), phosphatidylinositols (PI), phosphatidic acids (PA), diacylglycerols (DAG), ceramides (Cer), glucosylceramides (GlcCer), lactosylceramides (LacCer), monosialogangliosides (GM), disialogangliosides (GD), trisialogangliosides (GT), and quatrosialogangliosides (GQ).

The following materials were used according to the methods. HPLC or LC-MS grade of chloroform, methanol, water, acetonitrile, formic acid, methanol, isopropanol, ammonium acetate, acetic acid, potassium chloride and butylated hydroxytoluene (BHT) were purchased from Sigma-Aldrich (St. Louis, Mo., USA).

HPLC column (Acquity BEH C18, 2.1×50 mm id. 1.7 μm) was purchased from Waters (Milford, Mass., USA). HPLC pre-column (Widepore C18 4×2.0 mm) was purchased from Phenomenex (Torrance, Calif., USA). All labware used for the extraction were resistant to chloroform. Aerosol resistant filter tips (Molecular BioProducts) and Eppendorf 2 ml safe-lock tubes, 96-well twin.tec PCR plates, and Pierce-it-lite thermo-sealing foils were purchased from VWR International (West Chester, Pa., USA). CO-RE Filter Tips and 96-well 2 ml Whatman Uniplates were purchased from Hamilton Robotics (Bonaduz, Switzerland). Synthetic lipid standards were purchased from Avanti Polar Lipids (Alabaster, Ala., USA) and from Matreya (Pleasant Gap, Pa., USA).

Lipids were extracted in chloroform:methanol according to the following protocols. Samples were spiked with known amounts of non-endogenous synthetic internal standards for data normalization and endogenous lipid quantification. In shotgun lipidomics analysis; LPC 17:0, PC 17:0/17:0, PA 17:0/17:0, PE 17:0/17:0, PG 17:0/17:0, PS17:0/17:0, DAG 17:0/17:0, D6-CE 18:0, in ceramide and cerebroside lipidomics; Cer d18:1/17:0, D3-LacCer d18:1/16:0, and D3-GlcCer d18:1/16:0, and in ganglioside lipidomics; D3-GM1d18:1/18:0, were used as internal standards. Post-extract spiked non-endogenous synthetic external standards were used for quality controlling. Stock solutions of standards were prepared by dissolving appropriately weighed amounts of each standard in chloroform:methanol (2:1, V:V) to achieve a final concentration of 500 μM. An internal standard mixture containing each of the standard stock was created and used in lipid extraction.

Samples and quality control samples for each extraction batch were thawed on ice. The carotid artery plaque samples were weighed on ice by using a cryo-box and homogenized in ice-cold 70% methanol in water. The Mixer Mill 301 Teflon® adapters were kept at −20° C. Homogenization was performed at 15-25 Hz for 2-15 minutes with Mixer Mill 301 (Retch GmbH, Germany).

Lipid extraction of human samples was carried out in automated fashion using a Hamilton MICROLAB STAR system (Hamilton Robotics, Switzerland). Well-mixed samples were aliquoted into a 96-well 2 ml Whatman Uniplate containing ice-cold methanol and 0.1% BHT. 5 μl of serum and plasma and 30 μl of carotid artery plaques were used for shotgun- and ceramide and cerebroside lipidomics and 100 μl of serum and plasma and 200 μl of carotid artery plaques was used for ganglioside lipidomics. The samples were mixed thoroughly after each step in the extraction protocol. The extraction proceeded at room temperature by adding an appropriate volume of internal standard mixture and chloroform, and methanol and water in the case of ganglioside lipidomics. In shotgun and ceramide and cerebroside lipidomics, the organic phase separation was facilitated by adding 20 mM acetic acid and centrifuging the plate for 5 min at 500×g. The organic phase was transferred into a new 96-well 2 ml Whatman Uniplate. The remaining water-containing phase was washed by adding appropriate volume of chloroform followed by centrifugation. The two organic phases were pooled and evaporated under $N_2$ until dryness. The lipid extracts were then re-dissolved in chloroform:methanol (1:2, v:v) including the addition of the synthetic external standard. In ganglioside lipidomics, after thorough mixing the supernatant was collected after 30 min centrifugation at 2000×g. The remaining pellet was re-extracted with appropriate volume of water and chloroform:methanol (1:2, v:v) and the supernatant was collected in the same way as above. The pooled supernatant was subjected to solvent partitioning by addition of water and inversion of the sample tubes. The upper phase was collected after 30 min centrifugation at 2000×g. The lower phase was thoroughly re-extracted with potassium chloride and the produced upper phase was collected as mentioned above. The upper phases were pooled and evaporated under $N_2$ until dryness. The lipid extracts were then re-dissolved in chloroform:methanol (1:2, v:v). The extracts were stored in 2 ml safe-lock Eppendorf tubes at −20° C. prior to MS analysis. Required volumes of lipid extracts were aliquoted into an Eppendorf 96-well twin.tec PCR plate and the plate was heat-sealed with aluminum foil to avoid evaporation.

In shotgun lipidomics, lipid extracts were analyzed on a hybrid triple quadrupole/linear ion trap mass spectrometer (QTRAP 5500, AB Sciex) equipped with a robotic nanoflow ion source (NanoMate HD, Advion Biosciences). The instruments were operated in positive and negative ion modes. In positive ion the spray voltage was set to 1.0 to 1.4 kV and in negative ion mode to −1.0 to −1.4 kV. A gas pressure of 0.3-0.8 psi was used and the interface heater was set at 60° C. The collision energy (CE) and declustering potential (DP) was optimized for each lipid class using synthetic standards. The mass spectrometer was operated in unit resolution mode using a scan speed of 200 Da/s. Molecular lipids were analyzed in both positive and negative ion modes using multiple precursor ion scanning (MPIS) and neutral loss scanning (NLS) as described by Stahlman and colleagues (Stahlman M, et al. High-throughput shotgun lipidomics by quadrupole time-of-flight mass spectrometry. J Chromatogr B Analyt Technol Biomed Life Sci 2009).

In ceramide and cerebroside lipidomics and ganglioside lipidomics, the high performance liquid chromatography (HPLC) analyses were conducted in the following way. Chromatographic apparatus consisted of a CTC HTC PAL autosampler (CTC Analytics AG, Switzerland), a Rheos Allegro UHPLC pump (Flux Instruments AG, Switzerland), an external column heater set to 60° C. for ceramide and cerebroside lipidomics and 45° C. for ganglioside lipidomics, and the Acquity BEH C18 column with an in-line pre-column The extracted samples, 10 µl of each, were injected into the pre-column followed by the analytical column and delivered to the mass spectrometer at a flow rate of 500 µl/min. In ceramide and cerebroside lipidomics, A gradient was used for lipid analyte separation with solvent A comprising 10 mM ammonium acetate in HPLC grade water containing 0.1% formic acid and solvent B of 10 mM ammonium acetate in acetonitrile:isopropanol (4:3, V:V) containing 0.1% formic acid. The gradient was constructed in the following way: 0 min-65% B; 2 min-65% B; 2.5 min-75% B; 17.5 min-100% B; 22.5 min-100% B; 22.6 min-65% B; 25 min-65% B.

In ganglioside lipidomics, a gradient was used for lipid analyte separation with solvent A comprising 10 mM ammonium acetate in methanol containing 0.1% formic acid, solvent B of 10 mM ammonium acetate in isopropanol containing 0.1% formic acid and solvent C of 10 mM ammonium acetate in water containing 0.1% formic acid. The gradient was constructed in the following way: 0 min-45% A, 15% B, 40% C; 3 min-45% A, 15% B, 40% C, 3.5 min-55% A, 25% B, 20% C, 18.5 min-55% A, 35% B, 10% C, 18.6 min-60% A, 40% B, 0% C, 28.6 min-60% A, 40% B, 0% C; 29 min-45% A, 15% B, 40% C. The injection needle, loop, and syringe were washed with isopropanol/methanol between each sample.

The lipid extracts were analyzed by HPLC-MS/MS. The MS analysis was performed on a hybrid triple quadrupole/linear ion trap mass spectrometer equipped with the Turbo V™ Ion Source (4000 QTRAP, AB Sciex). The instrument was operating in positive and negative ion modes. The ion source voltage was set to 5500V for ceramide and cerebroside lipidomics and to −4500V for ganglioside lipidomics, and source temperature at 400° C. The collision energy (CE) and declustering potential (DP) was optimized for each lipid class using synthetic standards. A 20 sec dwell time was applied for each scan. Multiple reaction monitoring (MRM) scan mode was applied and based on the description by Sullards and colleagues (Sullards M C, et al: *Structure-specific, quantitative methods for analysis of sphingolipids by liquid chromatography-tandem mass spectrometry: "inside-out" sphingolipidomics. Methods Enzymol* 2007).

The data processing was done in the following way. Initially the retention time (in LC mode) and identification of each peak was done using endogenous standards and by Information Dependent Acquisition (IDA) experiments where applicable. The raw data were processed according to peak detected and retention time (in LC mode) in automated fashion. A stringent cutoff was applied for separating background noise from actual lipid peaks. Each sample was controlled and only accepted when fulfilling the stringent acceptance criteria. Peak area counts (cps) of detected peaks were converted into a list of corresponding lipid names. Lipids were normalized to their respective internal standard and sample volume or tissue weight to retrieve their concentrations.

Several quality controls were used in the lipidomic analyses. A calibration line using synthetic or isolated standards was obtained prior to sample analysis. Synthetic standards were chosen based on application and had similar properties to the endogenous lipids or analyte(s) of interest. The calibration line consisted of a minimum of five standards points covering the expected quantification range. A sample extracted without standard and standards extracted with no matrix, were included with the calibration line.

The calibration line was used to determine the dynamic quantification range for each lipid class monitored, e.g., the linear quantification limits. As the internal standards used behave in the same way as endogenous lipids they were used for quantifying endogenous lipid species. The calibration lines were based on the same internal standards that were used for quantification of the endogenous lipids.

In each sample extracted for lipids, the ratio of synthetic internal standards (1S) to corresponding post-extract spiked external standard (ES) was determined. The peak area (cps) ratio of internal to external standard (IS/ES) was used for calculating the Coefficient of Variation (CV) across all samples. The IS/ES ratio enabled the calculation of lipid extraction recovery.

Instrument control (IC) was included at the start, middle and end of each run. IC sample analyzed was an extracted reference plasma sample and a set of standards to monitor the instrument's performance, i.e., the intra- and inter-assay variation.

For each platform, a stringent cutoff was applied for separating background noise from actual lipid peaks. Each sample was controlled and only accepted when fulfilling the stringent acceptance criteria. Masses and counts of detected peaks were converted into a list of corresponding lipid names. Lipids were normalized to their respective internal standard and sample volume to retrieve their concentrations.

Statistical Analyses

Percentage changes in lipid concentrations between control and case groups were calculated as follows:

100*(AVG[C] in case group—AVG[C] in control group)/AVG[C] in control group Statistical significance was assigned based on standard t-test p-values.

In addition, ROC curves were used for finding lipid molecules and concentration cutoffs that separate the best cases from controls. Selectivity is calculated as a number of correctly identified cases divided by the total number of cases. Specificity is calculated as a number of correctly identified controls divided by the total number of controls. Selectivity and specificity was calculated for each lipid concentration, lipid to lipid ratio and ratio of lipid to clinical concentrations.

Example 3

Ethics

The LURIC study was approved by the ethics review committee at the "Landesärztekammer Rheinland-Pfalz" (Mainz, Germany). Written informed consent was obtained from each of the participants.

The SHAPS was approved by the Ethical Committee of the Sahlgrenska University hospital and informed consents were obtained from all patients.

Results

In the LURIC study LDL-cholesterol concentrations were practically identical in both groups and therefore this traditionally used lipid marker was not predictive or diagnostic for atherosclerotic disease in this study population. Baseline HDL-cholesterol concentrations were predictive for cardiovascular events; higher levels were related to better outcome and low levels associated with presence of cardiovascular events as established in earlier studies. The HDL-cholesterol levels were higher in the controls than in the case group, however the difference was not statistically significant.

Multiple lipidomic markers appeared as significant predictors of the atherosclerotic disease (Tables 2-20). As a total 289 molecular lipids were quantified. The significant predictors were selected based on the top fifty candidates from each category, when available. The biomarker candidates based on molecular lipid concentrations are presented in Tables 2, 5, 8 and 11. The candidates were selected according to the following criteria: t-test p-value ≤0.05 or sensitivity ≥60% and specificity ≥70%. Note that none of the traditional clinical chemistry measures reached statistical significance of risk prediction. The predictive value of new lipidomic biomarkers was increased when their levels were expressed as distinct lipid-lipid ratios or lipid-clinical chemistry measure ratios (e.g. LDL-C or HDL-C). The biomarker candidates based on ratios are listed in the Tables 3, 4, 6, 7, 9, 10, 12 and 13. The top five biomarker candidates are presented in Table 20. Top five candidates from each category, when available, were selected. Selection criteria: t-test p-value ≤0.05 and sensitivity ≥60% and specificity ≥70%. The top five biomarker candidates are presented in Table 20.

TABLE 2

Significant lipids in LURIC study. Lipid names, p-values and % change for negative correlation are presented.

| Lipid name | p-value | Percentage change |
|---|---|---|
| Positive correlation | | |
| Cer(d18:0/22:0) | 0.014687562 | 43.8 |
| Cer(d18:0/24:0) | 0.03339923 | 37.3 |
| Cer(d18:0/24:1) | 0.010517368 | 55.2 |
| Cer(d18:1/16:0) | 0.001269262 | 38.5 |
| Cer(d18:1/18:0) | 0.038490767 | 31.9 |
| Cer(d18:1/20:0) | 0.045662261 | 23.7 |
| Cer(d18:1/24:1) | 0.014565589 | 25.8 |
| GlcCer(d18:1/16:0) | 0.035689877 | 22.5 |
| GlcCer(d18:1/18:0) | 0.046657262 | 22.2 |
| LacCer(d18:1/18:0) | 0.046016525 | 28.5 |
| LacCer(d18:1/20:0) | 0.044453103 | 28.2 |
| LacCer(d18:1/22:0) | 0.017297489 | 23.2 |
| LacCer(d18:1/24:1) | 0.024132839 | 24.9 |
| Total LacCer | 0.049400032 | 18.8 |
| Negative correlation | | |
| CE 14:0 | 0.0305898 | −25.7 |
| CE 16:0 | 0.018719781 | −21.2 |
| CE 17:1 | 0.018922863 | −25.0 |
| CE 20:3 | 0.043641037 | −21.5 |
| PC 35:3 (PC O-34:3) | 0.049613882 | −23.9 |
| Total CE | 0.028926956 | −21.2 |

Second distinct molecular lipid ratios calculated and the most predictive molecular lipid ratios are shown in the table 3 and lipid to clinical ratios in table 4.

TABLE 3

Table of significant lipid to lipid ratios in LURIC. Lipid names, p-values, % change both for positive and negative correlation are presented.

| Lipid name | p-value | Percentage change |
|---|---|---|
| Positive correlation | | |
| CE 19:1/LPC 20:4 | 0.000471528 | 90.35934685 |
| Cer(d18:1/16:0)/LPC 16:0 | 0.000467595 | 49.36747677 |
| Cer(d18:1/16:0)/LPC 18:1 | 0.000199612 | 56.03521777 |
| Cer(d18:1/16:0)/LPC 18:2 | 0.000118204 | 90.10795901 |
| Cer(d18:1/16:0)/PC 16:0/20:4 | 0.000499877 | 83.81924555 |
| Cer(d18:1/16:0)/PC 18:1/18:2 | 0.000244291 | 66.68678964 |
| Cer(d18:1/16:0)/PC 33:2 (PC O-34:2) | 0.000655229 | 66.24801848 |
| Cer(d18:1/16:0)/PC 35:3 (PC O-36:3) | 0.000418086 | 64.92705203 |
| Cer(d18:1/16:0)/PC 35:4 (PC O-36:4) | 0.000353999 | 68.34396351 |
| Cer(d18:1/16:0)/PC 36:3 | 0.000834057 | 60.10383676 |
| Cer(d18:1/16:0)/PC 36:4 | 0.00071284 | 68.85058536 |
| Cer(d18:1/16:0)/PC 33:3 (PC O-34:3) | 0.000252735 | 119.7334815 |
| Cer(d18:1/16:0)/SM (d18:1/18:0) | 0.000664844 | 57.71839776 |
| Cer(d18:1/16:0)/SM (d18:1/23:0) (d18:1/22:1-OH) | 0.00077468 | 72.84650523 |
| Cer(d18:1/16:0)/SM (d18:1/24:0) (d18:1/23:1-OH) | 0.000233605 | 76.04913286 |
| Cer(d18:1/16:0)/SM (d18:1/24:1) (d18:1/23:2-OH) | 0.000193486 | 65.5335903 |
| Cer(d18:1/16:0)/SM (d18:1/25:1) (d18:1/24:2-OH) | 0.000645822 | 76.30000298 |
| Cer(d18:1/16:0)/Total CE | 0.000222044 | 83.61322653 |
| Cer(d18:1/16:0)/Total LPC | 5.25E−05 | 56.40298751 |
| Cer(d18:1/16:0)/Total PC | 0.000567032 | 53.98721906 |
| Cer(d18:1/20:0)/LPC 18:2 | 0.000700606 | 65.16225255 |
| Cer(d18:1/22:0)/LPC 18:2 | 0.000224484 | 66.03962762 |
| Cer(d18:1/22:0)/PC 33:3 (PC O-34:3) | 0.000752028 | 103.4190831 |
| Cer(d18:1/22:0)/SM (d18:1/24:0) (d18:1/23:1-OH) | 0.000679158 | 61.18198803 |
| Cer(d18:1/24:1)/LPC 18:2 | 8.77E−05 | 72.81688737 |
| Cer(d18:1/24:1)/PC 33:3 (PC O-34:3) | 0.000787728 | 110.0822885 |
| Cer(d18:1/24:1)/SM (d18:1/23:0) (d18:1/22:1-OH) | 0.000692488 | 61.73982957 |
| Cer(d18:1/24:1)/SM (d18:1/24:0) (d18:1/23:1-OH) | 0.000394736 | 67.04594956 |
| Cer(d18:1/24:1)/SM (d18:1/25:1) (d18:1/24:2-OH) | 0.000647979 | 64.08153764 |
| GlcCer(d18:1/16:0)/LPC 18:2 | 0.000318577 | 76.07058679 |
| GlcCer(d18:1/18:0)/LPC 18:2 | 0.000169434 | 77.26486553 |
| GlcCer(d18:1/26:1)/SM (d18:1/25:1) (d18:1/24:2-OH) | 0.000178336 | 63.26864438 |
| LacCer(d18:1/18:0)/PC 36:4 | 0.000817473 | 59.93586644 |
| LacCer(d18:1/22:0)/PC 16:0/20:4 | 0.00049939 | 64.33099382 |
| LacCer(d18:1/22:0)/PC 18:0/20:4 | 0.000668645 | 56.7328978 |
| LacCer(d18:1/22:0)/PC 35:4 (PC O-36:4) | 0.000474923 | 58.48665386 |
| LacCer(d18:1/22:0)/PC 36:4 | 0.000641968 | 56.20286668 |
| LacCer(d18:1/22:0)/SM (d18:1/24:0) (d18:1/23:1-OH) | 0.000383032 | 55.50328917 |
| LacCer(d18:1/22:0)/SM (d18:1/25:1) (d18:1/24:2-OH) | 0.000498406 | 67.63916268 |
| LacCer(d18:1/22:0)/Total CE | 0.000217583 | 61.14858395 |
| LacCer(d18:1/24:1)/PC 16:0/20:4 | 0.000169903 | 71.04956344 |
| LacCer(d18:1/24:1)/PC 18:0/20:4 | 0.000131686 | 63.66473081 |
| LacCer(d18:1/24:1)/PC 36:4 | 0.000846325 | 61.12325433 |
| LacCer(d18:1/24:1)/Total CE | 0.00033074 | 64.00805641 |
| PC 38:0/PC 38:5 | 0.000118576 | 49.99526445 |
| Negative correlation | | |
| LPC 20:4/PC 35:1 (PC O-36:1) | 0.005469186 | −42.92988466 |
| CE 20:4/GlcCer(d18:1/26:1) | 0.00337029 | −41.21294541 |
| CE 16:1/Total LacCer | 0.004341879 | −49.78676787 |
| CE 22:6/LacCer(d18:1/22:0) | 0.001791919 | −35.98982311 |
| CE 16:1/PC 37:2 (PC O-38:2) | 0.001932003 | −50.19239309 |
| CE 16:0/GlcCer(d18:1/16:0) | 0.002507744 | −37.19500497 |
| CE 22:6/Cer(d18:1/16:0) | 0.001805802 | −40.38963291 |
| CE 14:0/PC 37:2 (PC O-38:2) | 0.00389603 | −47.2207302 |

TABLE 3-continued

Table of significant lipid to lipid ratios in LURIC.
Lipid names, p-values, % change both for positive
and negative correlation are presented.

| Lipid name | p-value | Percentage change |
|---|---|---|
| CE 16:0/Total LacCer | 0.003381303 | −36.75585926 |
| CE 18:2/Cer(d18:1/16:0) | 0.001220921 | −43.8001271 |
| CE 16:0/LacCer(d18:1/22:0) | 0.004788276 | −36.68953669 |
| CE 20:4/GlcCer(d18:1/24:1) | 0.005069721 | −42.14059744 |
| CE 18:1/GlcCer(d18:1/16:0) | 0.002524358 | −37.23085101 |
| CE 20:4/GlcCer(d18:1/16:0) | 0.001477545 | −41.83985223 |
| CE 18:0/Cer(d18:1/16:0) | 0.002075144 | −42.03051749 |
| LPC 20:4/PC 37:2 (PC O-38:2) | 0.005821932 | −47.30224648 |
| CE 16:0/Cer(d18:1/24:1) | 0.002978992 | −37.07053992 |
| CE 17:1/LacCer(d18:1/22:0) | 0.00525151 | −40.9476074 |
| CE 18:2/GlcCer(d18:1/16:0) | 0.002154967 | −36.22537162 |
| CE 22:6/GlcCer(d18:1/16:0) | 0.003132181 | −34.94277238 |
| CE 14:0/PC 37:2 (PC O-38:2) | 0.00389603 | −47.2207302 |
| Total CE/Total LacCer | 0.004077513 | −36.83803507 |
| CE 14:0/Cer(d18:1/24:1) | 0.003928017 | −42.19201662 |
| CE 20:4/LacCer(d18:1/16:0) | 0.003899791 | −38.26867017 |
| CE 22:6/Total LacCer | 0.00254002 | −34.08992839 |
| CE 22:6/LacCer(d18:1/24:1) | 0.003438579 | −37.09419772 |
| CE 18:1/Cer(d18:1/16:0) | 0.001789273 | −45.01233662 |
| CE 16:1/Cer(d18:1/16:0) | 0.004672328 | −55.68777226 |
| CE 16:1/LacCer(d18:1/22:0) | 0.004046272 | −49.73838349 |
| CE 16:0/LacCer(d18:1/16:0) | 0.005173921 | −34.17652183 |
| CE 16:1/CE 22:2 | 0.00374579 | −52.31993179 |
| CE 16:1/Cer(d18:1/24:1) | 0.004187338 | −50.43425055 |
| CE 22:6/LacCer(d18:1/18:0) | 0.002952058 | −38.17114019 |
| CE 22:6/LacCer(d18:1/20:0) | 0.004327851 | −38.50191326 |
| CE 20:4/LacCer(d18:1/22:0) | 0.003517591 | −41.06206866 |
| CE 20:4/Cer(d18:1/24:1) | 0.002608289 | −40.26726712 |
| CE 16:1/CE 20:0 | 0.00482513 | −61.11065611 |
| CE 20:4/Cer(d18:1/16:0) | 0.00355192 | −48.24976193 |
| LPC 20:4/PC 37:2 (PC O-38:2) | 0.005821932 | −47.30224648 |
| CE 16:1/PC 37:2 (PC O-38:2) | 0.001932003 | −50.19239309 |
| CE 20:4/Total GlcCer | 0.00495873 | −40.61979833 |
| CE 20:4/Total LacCer | 0.003017988 | −40.88586792 |
| CE 20:4/SM (d18:1/14:0) (d18:1/13:1-OH) | 0.004440771 | −26.86787737 |
| LPC 20:4/PC 35:1 (PC O-36:1) | 0.005469186 | −42.92988466 |
| CE 14:0/Cer(d18:1/16:0) | 0.004068889 | −49.34846012 |
| CE 17:1/Cer(d18:1/16:0) | 0.00265453 | −48.06011055 |
| CE 17:1/Cer(d18:1/24:1) | 0.005136678 | −41.02641962 |
| CE 20:4/GlcCer(d18:1/18:0) | 0.004173616 | −38.62660227 |
| CE 16:0/Cer(d18:1/16:0) | 0.001040603 | −43.89062683 |
| CE 18:1/Cer(d18:1/24:1) | 0.003643091 | −37.90614466 |

TABLE 4

Table of significant lipid to clinical ratios in LURIC study. Lipid
names and clinical measurement, p-values and percentage change
both for positive and negative correlation are presented.

| Lipid name/Clinical measurement | p-value | Percentage change |
|---|---|---|
| Positive correlation | | |
| Cer(d18:0/22:0)/apolipoprotein A-I (mg/dL) | 0.002678941 | 62.12399702 |
| Cer(d18:0/22:0)/apolipoprotein A-II (mg/dL) | 0.001252968 | 63.54933064 |
| Cer(d18:0/22:0)/HDL cholesterol ester (mg/dL) | 0.002928701 | 73.44340777 |
| Cer(d18:0/24:1)/apolipoprotein A-II (mg/dL) | 0.00299459 | 77.0624651 |
| Cer(d18:0/24:1)/cholesterol ester (mg/dL) | 0.003754861 | 66.37295698 |
| Cer(d18:0/24:1)/HDL cholesterol ester (mg/dL) | 0.002469902 | 87.68140707 |
| Cer(d18:1/16:0)/apolipoprotein A-I (mg/dL) | 0.000367724 | 61.54836937 |
| Cer(d18:1/16:0)/apolipoprotein A-II (mg/dL) | 0.000292416 | 67.12282079 |
| Cer(d18:1/16:0)/apolipoprotein B (mg/dL) | 0.003188845 | 42.31501975 |
| Cer(d18:1/16:0)/apolipoprotein E (mg/dL) | 0.003166915 | 58.84301337 |
| Cer(d18:1/16:0)/body mass index (kg/m2) | 0.000384355 | 47.60031056 |
| Cer(d18:1/16:0)/cholesterol ester (mg/dL) | 0.000629969 | 57.36345926 |
| Cer(d18:1/16:0)/free cholesterol (mg/dL) | 0.001778521 | 40.30056332 |
| Cer(d18:1/16:0)/HDL cholesterol (EDTA) (mg/dL) | 0.00208774 | 62.8262521 |
| Cer(d18:1/16:0)/HDL cholesterol ester (mg/dL) | 0.001929489 | 74.51017169 |
| Cer(d18:1/16:0)/HDL phospholipid (mg/dL) | 0.001737827 | 52.36019336 |
| Cer(d18:1/16:0)/LDL phospholipid (mg/dL) | 0.003014691 | 45.0838551 |
| Cer(d18:1/16:0)/phospholipid (mg/dL) | 0.001238176 | 45.16946746 |
| Cer(d18:1/16:0)/total cholesterol (EDTA) (mg/dL) | 0.000785706 | 51.6957508 |
| Cer(d18:1/22:0)/apolipoprotein A-I (mg/dL) | 0.003465037 | 39.8359832 |
| Cer(d18:1/22:0)/apolipoprotein A-II (mg/dL) | 0.002247731 | 43.7098503 |
| Cer(d18:1/24:1)/apolipoprotein A-I (mg/dL) | 0.000839091 | 45.11297635 |
| Cer(d18:1/24:1)/apolipoprotein A-II (mg/dL) | 0.000752316 | 48.43414591 |
| Cer(d18:1/24:1)/cholesterol ester (mg/dL) | 0.000997776 | 39.02062567 |
| Cer(d18:1/24:1)/HDL cholesterol ester (mg/dL) | 0.002160218 | 54.64058021 |
| Cer(d18:1/24:1)/total cholesterol (EDTA) (mg/dL) | 0.001944642 | 34.55989651 |
| GlcCer(d18:1/16:0)/apolipoprotein A-I (mg/dL) | 0.001747609 | 40.95349137 |
| GlcCer(d18:1/16:0)/apolipoprotein A-II (mg/dL) | 0.001655128 | 45.26221529 |
| GlcCer(d18:1/16:0)/cholesterol ester (mg/dL) | 0.001953793 | 38.03805769 |
| GlcCer(d18:1/18:0)/apolipoprotein A-I (mg/dL) | 0.002507768 | 39.77171523 |
| GlcCer(d18:1/18:0)/apolipoprotein A-II (mg/dL) | 0.002967567 | 44.79796668 |
| GlcCer(d18:1/18:0)/cholesterol ester (mg/dL) | 0.003526205 | 35.94104407 |
| GlcCer(d18:1/26:1)/apolipoprotein A-II (mg/dL) | 0.002173729 | 42.55461531 |
| GlcCer(d18:1/26:1)/cholesterol ester (mg/dL) | 0.002872778 | 38.12528668 |
| LacCer(d18:1/22:0)/apolipoprotein A-I (mg/dL) | 0.000803998 | 44.38027847 |
| LacCer(d18:1/22:0)/apolipoprotein A-II (mg/dL) | 0.000931383 | 49.8603015 |
| LacCer(d18:1/22:0)/cholesterol ester (mg/dL) | 0.00171361 | 44.28362356 |

TABLE 4-continued

Table of significant lipid to clinical ratios in LURIC study. Lipid names and clinical measurement, p-values and percentage change both for positive and negative correlation are presented.

| Lipid name/Clinical measurement | p-value | Percentage change |
|---|---|---|
| LacCer(d18:1/22:0)/HDL cholesterol (EDTA) (mg/dL) | 0.00224985 | 43.63098656 |
| LacCer(d18:1/22:0)/HDL cholesterol ester (mg/dL) | 0.001926216 | 52.8411569 |
| LacCer(d18:1/22:0)/LDL free cholesterol (mg/dL) | 0.001966002 | 37.49255249 |
| LacCer(d18:1/22:0)/total cholesterol (EDTA) (mg/dL) | 0.003159661 | 39.0400307 |
| LacCer(d18:1/24:1)/apolipoprotein A-I (mg/dL) | 0.001170615 | 43.77660659 |
| LacCer(d18:1/24:1)/apolipoprotein A-II (mg/dL) | 0.001134222 | 49.89326123 |
| LacCer(d18:1/24:1)/cholesterol ester (mg/dL) | 0.002564795 | 44.0445289 |
| LacCer(d18:1/24:1)/HDL cholesterol ester (mg/dL) | 0.003076171 | 48.23813315 |
| PC 18:0/20:3/VLDL apolipoprotein B (mg/dL) | 0.003169362 | 95.78859327 |
| Total Cer/apolipoprotein A-I (mg/dL) | 0.002336548 | 37.51217992 |
| Total Cer/apolipoprotein A-II (mg/dL) | 0.001690797 | 41.27094891 |
| Total LacCer/apolipoprotein A-I (mg/dL) | 0.001634669 | 37.50538776 |
| Total LacCer/apolipoprotein A-II (mg/dL) | 0.001838827 | 42.21287876 |
| Negative correlation | | |
| CE 14:0/free fatty acids (mmol/L) | 0.022047397 | −51.0 |
| CE 16:0/apolipoprotein C-III (mg/dL) | 0.014736844 | −31.5 |
| CE 17:1/apolipoprotein C-III (mg/dL) | 0.017520913 | −32.9 |
| CE 17:1/free fatty acids (mmol/L) | 0.014911081 | −51.9 |
| CE 17:1/free glycerol (mg/dL) | 0.011000139 | −44.7 |
| CE 18:0/apolipoprotein C-III (mg/dL) | 0.018524136 | −31.0 |
| CE 18:1/apolipoprotein C-III (mg/dL) | 0.013940569 | −31.7 |
| CE 18:2/apolipoprotein C-III (mg/dL) | 0.011128685 | −32.8 |
| CE 20:3/free fatty acids (mmol/L) | 0.018108486 | −48.7 |
| CE 20:4/apolipoprotein C-III (mg/dL) | 0.012992834 | −34.4 |
| CE 20:4/free fatty acids (mmol/L) | 0.012353504 | −45.6 |
| LPC 18:2/apolipoprotein C-III (mg/dL) | 0.009297628 | −37.0 |
| PC 18:1/18:2/apolipoprotein C-III (mg/dL) | 0.01355363 | −30.8 |
| PC 39:0 (PC O-40:0)/free fatty acids (mmol/L) | 0.011590189 | −43.3863065 |
| PC 40:7/free fatty acids (mmol/L) | 0.011590189 | −43.4 |
| SM (d18:1/23:0) (d18:1/22:1-OH)/apolipoprotein C-III (mg/dL) | 0.020396809 | −31.6 |
| SM (d18:1/23:0) (d18:1/22:1-OH)/free fatty acids (mmol/L) | 0.015883723 | −41.5 |
| SM (d18:1/25:1) (d18:1/24:2-OH)/free fatty acids (mmol/L) | 0.009794403 | −50.98880228 |
| Total CE/apolipoprotein C-III (mg/dL) | 0.011184808 | −31.9 |

The results of the SHAPS study were in line with the LURIC study observations. The SHAPS data is presented in the Tables 5-7.

TABLE 5

Table of significant lipids in SHAPS study. Lipid names, p-values and % change both for positive and negative correlation are presented.

| Lipid name | p-value | Percentage change |
|---|---|---|
| Negative correlation | | |
| CE 16:0 | 0.009455261 | −19.5 |
| Cer(d18:0/24:0) | 0.00727472 | −35.5 |
| GD3-d18:1/16:0 | 0.011308821 | −25.6 |
| PC 16:0/16:1 | 0.009571408 | −36.8 |
| PC 37:5 (PC O-38:5) | 0.013821916 | −24.5 |
| SM (d18:1/16:1) (d18:1/15:2-OH) | 0.008131702 | −28.1 |
| SM(d18:1/18:1) | 0.00468767 | −31.0 |
| SM (d18:1/23:1) (d18:1/22:2-OH) | 0.000416109 | −32.7 |
| Total CE | 0.013196365 | −20.6 |
| Total GD3 | 0.011308821 | −25.6 |
| Total PC O | 0.002332179 | −29.4 |
| Total PC | 0.002012004 | −26.6 |

TABLE 6

Table of significant lipid to lipid ratios in SHAPS. Lipid names, p-values, percentage change both for positive and negative correlation are presented.

| Lipid ratio name | p-value | Percentage change |
|---|---|---|
| Positive correlation | | |
| Cer(d18:1/16:0)/Cer(d18:1/26:0) | 0.000462142 | 37.01057987 |
| DAG 16:1/16:1/PC 32:1 | 0.000164297 | 82.69222747 |
| DAG 16:1/16:1/PI 38:4 | 0.000169401 | 59.75577881 |
| GM3-d18:1/24:1/SM (d18:1/16:1) (d18:1/15:2-OH) | 0.000220977 | 55.99413212 |
| GM3-d18:1/24:1/SM (d18:1/18:1) | 0.000235142 | 57.78999778 |
| GlcCer(d18:1/24:1)/SM (d18:1/23:1) (d18:1/22:2-OH) | 0.000442436 | 84.60158129 |
| SM (d18:1/16:0) (d18:1/15:1-OH)/SM (d18:1/16:1) (d18:1/15:2-OH) | 0.000197947 | 27.33578644 |
| Negative correlation | | |
| CE 16:0/Cer(d18:1/24:1) | 0.001360084 | −27.64153039 |
| CE 16:0/DAG 16:1/16:1 | 0.001578991 | −28.95840866 |
| CE 16:1/CE 20:3 | 0.003773885 | −33.87140598 |
| CE 16:1/Cer(d18:1/16:0) | 0.0050017 | −40.55114395 |
| CE 16:1/Cer(d18:1/24:1) | 0.001196265 | −42.1521372 |
| CE 16:1/DAG 16:1/16:1 | 0.000417254 | −41.20191943 |
| CE 16:1/GM3-d18:1/24:1 | 0.005651103 | −46.81904893 |
| CE 16:1/LPC 16:0 | 0.004834796 | −33.21631623 |
| CE 18:2/Cer(d18:1/16:0) | 0.001278722 | −27.54230998 |
| CE 18:2/Cer(d18:1/24:1) | 0.000880725 | −31.80274825 |
| CE 18:2/DAG 16:1/16:1 | 0.003603789 | −32.1700757 |
| CE 18:2/GlcCer(d18:1/24:1) | 0.003812422 | −34.69951322 |

TABLE 6-continued

Table of significant lipid to lipid ratios in SHAPS.
Lipid names, p-values, percentage change both for
positive and negative correlation are presented.

| Lipid ratio name | p-value | Percentage change |
|---|---|---|
| CE 18:2/GM3-d18:1/24:1 | 0.002042845 | −33.86056889 |
| CE 18:3/Cer(d18:1/24:1) | 0.002389841 | −32.25076456 |
| CE 20:4/DAG 16:1/16:1 | 0.005203443 | −33.54106819 |
| Cer(d18:0/22:0)/PE 36:2 | 0.004999648 | −38.84047621 |
| Cer(d18:0/24:0)/Cer(d18:1/16:0) | 0.005651061 | −40.35096815 |
| Cer(d18:0/24:0)/DAG 16:1/16:1 | 0.002910156 | −42.26869994 |
| Cer(d18:1/24:0)/Cer(d18:1/24:1) | 0.002299011 | −24.76608144 |
| GD3-d18:1/16:0/GlcCer(d18:1/24:1) | 0.004342032 | −32.0002382 |
| GlcCer(d18:1/26:0)/GlcCer(d18:1/26:1) | 0.00262958 | −24.97108611 |
| GM3-d18:1/18:0/GlcCer(d18:1/24:1) | 0.003743069 | −27.07575879 |
| GM3-d18:1/18:0/GM3-d18:1/24:1 | 0.000109712 | −23.84051852 |
| GM3-d18:1/20:0/GM3-d18:1/24:1 | 4.05E−05 | −25.790617 |
| GM3-d18:1/21:0/GM3-d18:1/24:1 | 0.00025679 | −29.69734028 |
| GM3-d18:1/22:1/GM3-d18:1/24:1 | 2.27E−05 | −22.64333818 |
| GM3-d18:1/23:0/GM3-d18:1/24:1 | 0.001796684 | −21.51709432 |
| PC 16:0/18:2/PE 36:2 | 0.003018726 | −33.0252666 |
| PC 32:1/PC 36:1 | 0.005258614 | −32.73307243 |
| PC 34:1/PE 36:2 | 0.004286691 | −36.87050262 |
| PC 34:2/PE 36:2 | 7.75E−05 | −39.56681037 |
| PC 34:3/PE 36:2 | 0.00093778 | −35.97189686 |
| PC 36:2/PE 36:2 | 0.004881243 | −38.02507206 |
| SM (d18:1/16:1) (d18:1/15:2-OH)/SM (d18:1/24:1) (d18:1/23:2-OH) | 0.003253011 | −25.08641399 |
| SM (d18:1/18:1)/SM (d18:1/24:1) (d18:1/23:2-OH) | 0.004081104 | −27.14819795 |
| SM (d18:1/23:1) (d18:1/22:2-OH)/SM (d18:1/24:1) (d18:1/23:2-OH) | 0.002697803 | −30.33837495 |

TABLE 7

Table of significant lipid to clinical ratios in SHAPS.
Lipid names, p-values, percentage change both for positive
and negative correlation are presented.

| Lipid name/Clinical measurement | p-value | Percentage change |
|---|---|---|
| Positive correlation | | |
| DAG 16:1/16:1/HDL | 0.01291686 | 53.8 |
| GM3-d18:1/24:2/HDL | 0.015381289 | 31.6 |
| GlcCer(d18:1/26:1)/HDL | 0.043858869 | 49.4 |
| Cer(d18:1/24:1)/LDL | 0.026096231 | 31.1 |
| GM3-d18:1/16:0/HDL | 0.038988537 | 25.8 |
| Cer(d18:1/24:1)/Chol | 0.00527498 | 26.8 |
| Cer(d18:1/16:0)/Chol | 0.019503081 | 18.2 |
| Cer(d18:1/24:1)/HDL | 0.016111238 | 59.0 |
| GM3-d18:1/24:1/HDL | 0.00267968 | 51.0 |
| GlcCer(d18:1/24:1)/HDL | 0.013244877 | 63.3 |
| Cer(d18:1/16:0)/HDL | 0.036889394 | 45.8 |
| Negative correlation | | |
| CE 14:0/TG | 0.012590071 | −42.13588123 |
| CE 16:0/TG | 0.002583829 | −36.7334504 |
| CE 16:1/Chol | 0.008389535 | −28.33597812 |
| CE 16:1/TG | 0.002007089 | −48.39087067 |
| CE 18:0/TG | 0.016144113 | −41.13616053 |
| CE 18:2/TG | 0.002102339 | −41.06062212 |
| CE 18:3/TG | 0.010621463 | −40.40096544 |
| CE 20:4/TG | 0.022172682 | −34.03007693 |
| Cer(d18:0/22:0)/TG | 0.000430556 | −47.22783762 |
| Cer(d18:0/24:0)/TG | 0.000169562 | −50.81345375 |
| Cer(d18:0/24:1)/TG | 0.004718764 | −44.02645803 |
| Cer(d18:1/24:0)/TG | 0.006103094 | −37.69337481 |
| Cer(d18:1/26:0)/TG | 0.011760588 | −43.11323904 |
| DAG 18:1/18:2/TG | 0.001478738 | −31.57202102 |
| GD1-d18:1/16:0/TG | 0.024026839 | −48.92359261 |
| GD3-d18:1/16:0/TG | 0.008681266 | −43.54025662 |
| GM3-d18:1/18:0/TG | 0.02443951 | −35.77082537 |
| GM3-d18:1/21:0/TG | 0.014997258 | −39.62591911 |

TABLE 7-continued

Table of significant lipid to clinical ratios in SHAPS.
Lipid names, p-values, percentage change both for positive
and negative correlation are presented.

| Lipid name/Clinical measurement | p-value | Percentage change |
|---|---|---|
| LacCer(d18:1/22:0)/TG | 0.012167842 | −41.61161247 |
| PC 16:0/16:1/TG | 0.010587549 | −48.72854121 |
| PC 16:0/18:1/TG | 0.012957457 | −38.82817743 |
| PC 16:0/18:2/TG | 0.001990548 | −41.45635691 |
| PC 16:0/20:4/TG | 0.010350168 | −41.16690299 |
| PC 16:0/22:5/TG | 0.021056239 | −40.06186395 |
| PC 16:0/22:6/TG | 0.007844831 | −41.90415263 |
| PC 18:0/18:2/TG | 0.014544147 | −35.55584409 |
| PC 18:0/20:3/TG | 0.001935253 | −44.80069954 |
| PC 18:2/18:2/TG | 0.009380936 | −50.91970106 |
| PC 30:0/TG | 0.006982736 | −45.07219763 |
| PC 32:1/TG | 0.01388029 | −58.98862014 |
| PC 34:1/TG | 0.004027785 | −42.82259496 |
| PC 34:2/TG | 0.002207437 | −46.73076262 |
| PC 34:3/TG | 0.008706198 | −42.28782691 |
| PC 35:2/TG | 0.016839779 | −40.08953521 |
| PC 36:2/TG | 0.025577365 | −44.56055525 |
| PC 36:4/TG | 0.010955026 | −40.93262531 |
| PC 38:3/TG | 0.009115348 | −43.20405649 |
| PC 38:4/TG | 0.022099265 | −40.71964271 |
| PC 40:6/TG | 0.016443829 | −39.33010265 |
| PC 35:2 (PC O-36:2)/TG | 0.016839779 | −40.08953521 |
| PI 36:2/TG | 0.018414068 | −33.26578536 |
| PI 38:3/TG | 0.00646278 | −41.87676619 |
| PI 38:4/TG | 0.01586346 | −36.68247363 |
| SM (d18:1/14:0) (d18:1/13:1-OH)/TG | 0.008912455 | −44.8243579 |
| SM (d18:1/16:1) (d18:1/15:2-OH)/TG | 0.009812465 | −43.3695667 |
| SM (d18:1/17:0) (d18:1/16:1-OH)/TG | 0.016419545 | −42.86279216 |
| SM (d18:1/18:1)/TG | 0.005568449 | −44.15754076 |
| SM (d18:1/23:1) (d18:1/22:2-OH)/TG | 0.005429528 | −47.70207646 |
| SM (d18:1/24:0) (d18:1/23:1-OH)/TG | 0.015686293 | −39.71612874 |

The biomarker ability of measured lipids was assessed also by calculating the sensitivity and specificity values for each lipid and their ratios to other lipids or classical biomarkers such as LDL-C and apolipoproteins. This ROC curve analysis revealed a number of biomarker candidates that have equal of higher than 75% sensitivity and specificity for predicting CVD risk (Tables 8-13).

TABLE 8

Significant lipids in LURIC study. The lipids
are sorted by top sensitivity and specificity.

| Lipid name | Sensitivity | Specificity | Percentage change |
|---|---|---|---|
| Positive correlation | | | |
| Cer(d18:1/16:0) | 0.61 | 0.78 | 38.5 |
| LacCer(d18:1/24:1) | 0.61 | 0.78 | 24.9 |
| LacCer(d18:1/22:0) | 0.72 | 0.70 | 23.2 |
| LacCer(d18:1/24:0) | 0.61 | 0.73 | 20.7 |
| Total Cer | 0.61 | 0.70 | 19.6 |
| Total LacCer | 0.78 | 0.70 | 18.8 |
| GlcCer(d18:1/24:0) | 0.61 | 0.70 | 15.9 |
| Total GlcCer | 0.61 | 0.70 | 15.0 |
| LacCer(d18:1/16:0) | 0.61 | 0.70 | 14.7 |
| Negative correlation | | | |
| PC 16:0/20:4 | 0.67 | 0.70 | −12.4 |
| CE 18:0 | 0.67 | 0.73 | −17.9 |
| Total CE | 0.61 | 0.70 | −21.2 |

TABLE 8-continued

Significant lipids in LURIC study. The lipids are sorted by top sensitivity and specificity.

| Lipid name | Sensitivity | Specificity | Percentage change |
|---|---|---|---|
| CE 20:3 | 0.61 | 0.73 | −21.5 |
| CE 14:0 | 0.61 | 0.75 | −25.7 |

TABLE 9

Table of significant lipid to lipid ratios in LURIC study. The lipid ratios are sorted by top sensitivity and specificity.

| Lipid ratio name | Sensitivity | Specificity | Percentage change |
|---|---|---|---|
| Positive correlation | | | |
| PC 18:0/20:3/PC 33:3 (PC O-34:3) | 0.87 | 0.70 | 104.1 |
| CE 19:1/LPC 20:4 | 0.83 | 0.70 | 90.4 |
| GlcCer(d18:1/26:1)/LPC 18:2 | 0.78 | 0.70 | 72.7 |
| LacCer(d18:1/24:1)/Total CE | 0.83 | 0.73 | 64.0 |
| Cer(d18:1/24:1)/Total CE | 0.78 | 0.73 | 63.1 |
| LacCer(d18:1/22:0)/Total CE | 0.78 | 0.73 | 61.1 |
| Cer(d18:1/16:0)/PC 36:3 | 0.78 | 0.78 | 60.1 |
| CE 22:2/LPC 20:4 | 0.83 | 0.71 | 59.7 |
| Cer(d18:1/20:0)/SM (d18:1/23:0) (d18:1/22:1-OH) | 0.78 | 0.72 | 56.8 |
| Cer(d18:1/22:0)/Total CE | 0.83 | 0.70 | 55.7 |
| LacCer(d18:1/18:0)/PC 40:7 | 0.82 | 0.70 | 55.4 |
| GlcCer(d18:1/16:0)/SM (d18:1/24:0) (d18:1/23:1-OH) | 0.78 | 0.70 | 54.9 |
| Cer(d18:1/16:0)/LPC 18:1 | 0.78 | 0.71 | 53.5 |
| Cer(d18:1/24:1)/PC 35:4 (PC O-36:4) | 0.78 | 0.73 | 53.3 |
| Cer(d18:1/22:0)/SM (d18:1/23:0) (d18:1/22:1-OH) | 0.78 | 0.82 | 52.1 |
| Cer(d18:1/20:0)/Total CE | 0.78 | 0.70 | 49.9 |
| Cer(d18:1/16:0)/PC 36:2 | 0.78 | 0.73 | 49.5 |
| Cer(d18:1/16:0)/PC 18:0/18:2 | 0.83 | 0.70 | 48.7 |
| Cer(d18:1/22:0)/PC 40:7 | 0.76 | 0.76 | 48.1 |
| Cer(d18:1/22:0)/PC 39:0 (PC O-40:0) | 0.76 | 0.76 | 48.1 |
| GlcCer(d18:1/18:0)/LPC 18:1 | 0.78 | 0.72 | 42.5 |
| CE 20:0/PC 40:4 | 0.80 | 0.73 | 40.5 |
| GlcCer(d18:1/16:0)/PC 36:2 | 0.78 | 0.70 | 37.5 |
| LacCer(d18:1/16:0)/PC 35:2 (PC O-36:2) | 0.78 | 0.70 | 28.6 |
| PC 39:7 (PC O-40:7)/Total CE | 0.80 | 0.71 | 26.7 |
| PC 38:0/Total CE | 0.79 | 0.71 | 25.8 |
| PC 38:0/PC 35:6 (PC O-36:5) | 0.79 | 0.71 | 23.9 |
| Total LacCer/Total PC O | 0.78 | 0.70 | 23.4 |
| SM (d18:1/14:0) (d18:1/13:1-OH)/SM (d18:1/23:0) (d18:1/22:1-OH) | 0.83 | 0.71 | 21.8 |
| Negative correlation | | | |
| SM (d18:1/23:0) (d18:1/22:1-OH)/Total Cer | 0.78 | 0.72 | −24.9 |
| CE 18:2/Cer(d18:1/22:0) | 0.83 | 0.75 | −28.0 |
| PC 36:4/PC 38:0 | 0.79 | 0.74 | −29.3 |
| CE 18:2/Total Cer | 0.78 | 0.70 | −29.6 |
| CE 20:4/Cer(d18:1/22:0) | 0.78 | 0.70 | −32.0 |
| CE 18:1/LacCer(d18:1/16:0) | 0.78 | 0.70 | −34.4 |
| CE 18:1/GlcCer(d18:1/18:0) | 0.78 | 0.70 | −34.5 |
| CE 18:1/LacCer(d18:1/22:0) | 0.78 | 0.70 | −35.5 |
| CE 22:6/LacCer(d18:1/22:0) | 0.78 | 0.74 | −36.0 |
| Total CE/Total LacCer | 0.83 | 0.73 | −36.8 |
| CE 18:1/Total LacCer | 0.78 | 0.70 | −36.9 |
| CE 20:4/LacCer(d18:1/16:0) | 0.78 | 0.70 | −38.3 |
| CE 18:1/LacCer(d18:1/24:1) | 0.83 | 0.70 | −39.1 |
| CE 20:4/Cer(d18:1/24:1) | 0.78 | 0.70 | −40.3 |
| LPC 18:2/LacCer(d18:1/22:0) | 0.78 | 0.75 | −40.9 |
| CE 20:4/Total LacCer | 0.78 | 0.70 | −40.9 |
| CE 17:1/LacCer(d18:1/20:0) | 0.76 | 0.72 | −42.7 |
| CE 20:4/LacCer(d18:1/24:1) | 0.83 | 0.70 | −43.;normal0 |

TABLE 9-continued

Table of significant lipid to lipid ratios in LURIC study. The lipid ratios are sorted by top sensitivity and specificity.

| Lipid ratio name | Sensitivity | Specificity | Percentage change |
|---|---|---|---|
| CE 16:1/GlcCer(d18:1/18:0) | 0.78 | 0.73 | −46.2 |
| LPC 20:4/PC 38:0 | 0.82 | 0.73 | −47.1 |

TABLE 10

Table of significant lipid to clinical ratios in LURIC study. The lipid ratios are sorted by top sensitivity and specificity.

| Lipid name/Clinical measurement | Sensitivity | Specificity | Percentage change |
|---|---|---|---|
| Positive correlation | | | |
| Cer(d18:1/16:0)/apolipoprotein A-II (mg/dL) | 0.72 | 0.73 | 67.1 |
| LacCer(d18:1/24:1)/apolipoprotein E (mg/dL) | 0.72 | 0.70 | 55.1 |
| Cer(d18:1/24:1)/HDL cholesterol ester (mg/dL) | 0.72 | 0.73 | 54.6 |
| LacCer(d18:1/22:0)/HDL cholesterol ester (mg/dL) | 0.72 | 0.73 | 52.8 |
| LacCer(d18:1/24:0)/HDL cholesterol ester (mg/dL) | 0.72 | 0.70 | 47.7 |
| LacCer(d18:1/24:0)/apolipoprotein C-II (mg/dL) | 0.76 | 0.70 | 47.5 |
| GlcCer(d18:1/16:0)/HDL cholesterol ester (mg/dL) | 0.72 | 0.70 | 47.3 |
| LacCer(d18:1/24:1)/apolipoprotein A-I (mg/dL) | 0.72 | 0.75 | 43.8 |
| Total LacCer/HDL cholesterol ester (mg/dL) | 0.72 | 0.73 | 43.8 |
| Cer(d18:1/22:0)/apolipoprotein A-II (mg/dL) | 0.72 | 0.70 | 43.7 |
| LacCer(d18:1/22:0)/HDL cholesterol (EDTA) (mg/dL) | 0.72 | 0.78 | 43.6 |
| Cer(d18:1/20:0)/apolipoprotein A-I (mg/dL) | 0.72 | 0.70 | 42.7 |
| LacCer(d18:1/24:0)/HDL cholesterol (EDTA) (mg/dL) | 0.72 | 0.70 | 40.7 |
| LacCer(d18:1/18:0)/LDL cholesterol (EDTA) (mg/dL) | 0.72 | 0.70 | 40.4 |
| Cer(d18:1/22:0)/apolipoprotein A-I (mg/dL) | 0.72 | 0.73 | 39.8 |
| GlcCer(d18:1/18:0)/apolipoprotein A-I (mg/dL) | 0.72 | 0.70 | 39.8 |
| LacCer(d18:1/16:0)/HDL cholesterol ester (mg/dL) | 0.72 | 0.73 | 39.6 |
| Cer(d18:1/24:1)/cholesterol ester (mg/dL) | 0.72 | 0.70 | 39.0 |
| Total LacCer/apolipoprotein A-I (mg/dL) | 0.72 | 0.73 | 37.5 |
| Cer(d18:1/20:0)/HDL phospholipid (mg/dL) | 0.72 | 0.70 | 35.6 |
| Total LacCer/cholesterol ester (mg/dL) | 0.78 | 0.70 | 35.6 |
| LacCer(d18:1/24:1)/LDL cholesterol ester (mg/dL) | 0.78 | 0.70 | 35.4 |
| Cer(d18:1/24:1)/total cholesterol (EDTA) (mg/dL) | 0.72 | 0.70 | 34.6 |
| GlcCer(d18:1/24:0)/apolipoprotein A-I (mg/dL) | 0.72 | 0.70 | 33.9 |
| LacCer(d18:1/24:1)/LDL cholesterol (EDTA) (mg/dL) | 0.78 | 0.70 | 33.7 |
| Cer(d18:1/24:1)/LDL phospholipid (mg/dL) | 0.72 | 0.70 | 33.2 |
| Total GlcCer/apolipoprotein A-I (mg/dL) | 0.72 | 0.83 | 32.9 |
| LacCer(d18:1/24:1)/LDL free cholesterol (mg/dL) | 0.72 | 0.80 | 32.8 |
| Cer(d18:1/22:0)/cholesterol ester (mg/dL) | 0.78 | 0.73 | 32.6 |

TABLE 10-continued

Table of significant lipid to clinical ratios in LURIC study.
The lipid ratios are sorted by top sensitivity and specificity.

| Lipid name/Clinical measurement | Sensitivity | Specificity | Percentage change |
|---|---|---|---|
| LacCer(d18:1/24:1)/apolipoprotein B (mg/dL) | 0.72 | 0.73 | 31.5 |
| Cer(d18:1/22:0)/LDL cholesterol (EDTA) (mg/dL) | 0.72 | 0.70 | 31.4 |
| Total Cer/cholesterol ester (mg/dL) | 0.78 | 0.70 | 30.5 |
| LacCer(d18:1/16:0)/cholesterol ester (mg/dL) | 0.72 | 0.75 | 29.8 |
| Cer(d18:1/22:0)/total cholesterol (EDTA) (mg/dL) | 0.72 | 0.70 | 28.7 |
| LacCer(d18:1/24:1)/HDL free cholesterol (mg/dL) | 0.72 | 0.70 | 27.9 |
| Total LacCer/LDL cholesterol ester (mg/dL) | 0.78 | 0.75 | 27.7 |
| Total LacCer/LDL cholesterol (EDTA) (mg/dL) | 0.78 | 0.75 | 26.7 |
| Total Cer/total cholesterol (EDTA) (mg/dL) | 0.72 | 0.73 | 26.6 |
| Total LacCer/phospholipid (mg/dL) | 0.72 | 0.75 | 25.4 |
| GlcCer(d18:1/20:0)/cholesterol ester (mg/dL) | 0.72 | 0.73 | 23.8 |
| Total LacCer/HDL free cholesterol (mg/dL) | 0.72 | 0.75 | 23.7 |
| Total LacCer/apolipoprotein B (mg/dL) | 0.72 | 0.78 | 22.6 |
| LacCer(d18:1/16:0)/LDL cholesterol ester (mg/dL) | 0.72 | 0.78 | 22.1 |
| Total LacCer/LDL phospholipid (mg/dL) | 0.78 | 0.70 | 21.8 |
| LacCer(d18:1/16:0)/LDL cholesterol (EDTA) (mg/dL) | 0.72 | 0.73 | 21.4 |
| Negative correlation | | | |
| CE 20:4/apolipoprotein C-III (mg/dL) | 0.72 | 0.75 | −34.4 |
| CE 14:0/apolipoprotein C-III (mg/dL) | 0.72 | 0.75 | −36.1 |
| CE 20:4/free fatty acids (mmol/L) | 0.72 | 0.70 | −45.6 |
| LPC 20:4/free fatty acids (mmol/L) | 0.77 | 0.79 | −51.3 |
| Total PC O/C-reactive protein (mg/dL) | 0.72 | 0.78 | −63.9 |

TABLE 11

Table of significant lipids in SHAPS study. The lipids are sorted by top sensitivity and specificity.

| Lipid name | Sensitivity | Specificity | Percentage change |
|---|---|---|---|
| Negative correlation | | | |
| Cer(d18:1/26:1) | 0.67 | 0.80 | −4.1 |
| CE 15:0 | 0.73 | 0.73 | −12.4 |
| SM (d18:1/15:0) (d18:1/14:1-OH) | 0.75 | 0.73 | −15.5 |
| GM3-d18:1/18:0 | 0.67 | 0.73 | −16.6 |
| PC 37:5(PC O-36:5) | 0.75 | 0.73 | −19.0 |
| CE 16:0 | 0.83 | 0.80 | −19.5 |
| Total CE | 0.75 | 0.93 | −20.6 |
| GM3-d18:1/21:0 | 0.75 | 0.73 | −21.1 |
| PC 16:0/18:2 | 0.67 | 0.80 | −22.6 |
| Total PI | 0.83 | 0.80 | −23.6 |
| SM (d18:1/17:0) (d18:1/16:1-OH) | 0.70 | 0.92 | −23.8 |
| GD3-d18:1/16:0 | 0.83 | 0.71 | −25.6 |
| Total GD3 | 0.83 | 0.71 | −25.6 |
| Cer(d18:1/26:0) | 0.75 | 0.73 | −25.6 |
| PC 18:0/20:5 | 0.82 | 0.85 | −26.6 |
| Total PC | 0.83 | 0.80 | −26.6 |
| PI 38:3 | 0.83 | 0.73 | −26.8 |
| PC 40:5 | 0.75 | 0.73 | −27.3 |
| GM2-d18:1/18:0 | 0.73 | 0.87 | −27.6 |
| Total GM2 | 0.73 | 0.87 | −27.6 |
| GD1-d18:1/16:0 | 0.92 | 0.77 | −28.1 |
| PC 16:0/20:5 | 0.83 | 0.87 | −28.1 |
| PC 16:0/22:5 | 0.75 | 0.73 | −28.5 |
| PC 18:0/20:3 | 0.75 | 0.79 | −28.7 |
| PC 16:0/22:6 | 0.83 | 0.73 | −29.3 |
| Total PC O | 0.83 | 0.80 | −29.4 |
| PI 38:4 | 0.83 | 0.80 | −29.5 |
| SM (d18:1/18:1) | 0.83 | 0.87 | −31.0 |
| PC 16:0/20:4 | 0.67 | 0.73 | −31.7 |
| SM (d18:1/23:1) (d18:1/22:2-OH) | 0.83 | 0.73 | −32.7 |

TABLE 12

Table of significant lipid to lipid ratios in SHAPS study. The lipid ratios are sorted by top sensitivity and specificity.

| Lipid ratio name | Sensitivity | Specificity | Percentage change |
|---|---|---|---|
| Positive correlation | | | |
| LPC 18:1/PC 32:1 | 0.92 | 0.77 | 81.5 |
| Cer(d18:1/24:1)/PC 32:1 | 1 | 0.73 | 75.1 |
| GM3-d18:1/24:1/SM (d18:1/23:1) (d18:1/22:2-OH) | 1 | 0.73 | 73.6 |
| GM3-d18:1/24:1/PC 32:1 | 0.92 | 0.73 | 62.5 |
| DAG 16:1/16:1/PC 30:0 | 0.92 | 0.79 | 62.0 |
| Cer(d18:1/24:1)/SM (d18:1/18:1) | 0.92 | 0.73 | 60.9 |
| GM3-d18:1/24:1/SM (d18:1/18:1) | 0.92 | 0.93 | 57.8 |
| GM3-d18:1/24:1/SM (d18:1/16:1) (d18:1/15:0-OH) | 0.92 | 0.73 | 56.0 |
| Cer(d18:1/16:0)/PC 32:1 | 0.92 | 0.73 | 55.4 |
| LacCer(d18:1/16:0)/PC 40:6 | 0.92 | 0.80 | 55.1 |
| Cer(d18:1/24:1)/PC 38:4 | 0.92 | 0.73 | 54.2 |
| LPC 18:0/PC 32:1 | 0.92 | 0.79 | 53.8 |
| Cer(d18:1/24:1)/PC 34:2 | 0.92 | 0.80 | 51.8 |
| GM3-d18:1/24:2/SM (d18:1/23:1) (d18:1/22:2-OH) | 0.92 | 0.80 | 50.2 |
| GM3-d18:1/24:2/PC 32:1 | 0.92 | 0.73 | 49.5 |
| GM3-d18:1/24:1/PC 34:2 | 0.92 | 0.73 | 49.4 |
| GlcCer(d18:1/16:0)/PC 32:1 | 0.92 | 0.73 | 46.9 |
| GM3-d18:1/24:1/PC 36:4 | 0.92 | 0.73 | 45.9 |
| GM3-d18:1/16:0/SM (d18:1/23:1) (d18:1/22:2-OH) | 0.92 | 0.87 | 44.8 |
| GM3-d18:1/24:1/PC 34:1 | 0.92 | 0.73 | 42.8 |
| Cer(d18:1/16:0)/PC 34:2 | 0.92 | 0.73 | 40.4 |
| GlcCer(d18:1/16:0)/PC 34:2 | 0.92 | 0.73 | 38.4 |
| GM3-d18:1/16:0/PC 32:1 | 1 | 0.73 | 38.3 |
| Cer(d18:1/16:0)/PC 34:1 | 0.92 | 0.73 | 35.0 |
| Cer(d18:1/24:1)/PC 34:3 | 0.92 | 0.73 | 34.4 |
| GlcCer(d18:1/16:0)/PC 34:1 | 1 | 0.73 | 29.6 |
| GM3-d18:1/18:0/PC 32:1 | 0.92 | 0.73 | 25.8 |
| Cer(d18:1/16:0)/PC 34:3 | 1 | 0.73 | 20.0 |
| GlcCer(d18:1/16:0)/PC 34:3 | 1 | 0.73 | 17.7 |
| LPC 16:0/SM (d18:1/14:0) (d18:1/13:1-OH) | 0.92 | 0.80 | 16.6 |
| GlcCer(d18:1/20:0)/PC 34:3 | 1 | 0.73 | 9.7 |
| GlcCer(d18:1/18:0)/PC 34:3 | 0.92 | 0.73 | 5.5 |
| Negative correlation | | | |
| GM3-d18:1/20:0/GM3-d18:1/22:0 | 0.92 | 0.73 | −11.2 |
| GM3-d18:1/22:1/GM3-d18:1/24:1 | 0.92 | 0.93 | −22.6 |
| Cer(d18:1/26:0)/GlcCer(d18:1/16:0) | 0.92 | 0.73 | −23.4 |
| GM3-d18:1/20:0/GM3-d18:1/24:1 | 1 | 0.73 | −25.8 |
| CE 18:2/Cer(d18:1/16:0) | 0.92 | 0.80 | −27.5 |
| CE 18:2/GlcCer(d18:1/26:1) | 0.92 | 0.73 | −29.5 |
| CE 18:3/Cer(d18:1/16:0) | 0.92 | 0.80 | −30.0 |
| CE 18:2/Cer(d18:1/24:1) | 0.92 | 0.87 | −31.8 |
| GD3-d18:1/16:0/GM3-d18:1/24:1 | 0.92 | 0.79 | −32.0 |
| Cer(d18:1/26:0)/GlcCer(d18:1/24:1) | 0.92 | 0.73 | −33.3 |
| CE 16:1/LPC 16:0 | 0.92 | 0.73 | −33.5 |
| CE 16:1/CE 20:3 | 0.92 | 0.80 | −33.9 |
| CE 16:1/LPC 18:1 | 0.92 | 0.73 | −40.0 |

TABLE 12-continued

Table of significant lipid to lipid ratios in SHAPS study. The lipid ratios are sorted by top sensitivity and specificity.

| Lipid ratio name | Sensitivity | Specificity | Percentage change |
|---|---|---|---|
| CE 16:1/Cer(d18:1/16:0) | 0.92 | 0.73 | −40.6 |
| CE 16:1/DAG 16:1/16:1 | 0.92 | 0.93 | −41.2 |
| CE 16:1/LacCer(d18:1/16:0) | 0.92 | 0.73 | −41.7 |

TABLE 13

Table of significant lipid to clinical ratios in SHAPS study. The lipid ratios are sorted by top sensitivity and specificity.

| Lipid name/Clinical measurement | Sensitivity | Specificity | Percentage change |
|---|---|---|---|
| *Positive correlation* | | | |
| GlcCer(d18:1/24:1)/HDL | 0.83 | 0.80 | 63.3 |
| DAG 16:1/16:1/HDL | 0.67 | 0.79 | 53.8 |
| Cer(d18:1/24:1)/LDL | 0.67 | 0.80 | 31.1 |
| Cer(d18:1/24:1)/Chol | 0.92 | 0.73 | 26.8 |
| Cer(d18:1/16:0)/Chol | 0.75 | 0.73 | 18.2 |
| *Negative correlation* | | | |
| Cer(d18:1/24:0)/Chol | 0.67 | 0.73 | −3.6 |
| CE 18:0/LDL | 0.83 | 0.71 | −7.8 |
| CE 18:2/LDL | 0.75 | 0.73 | −10.9 |
| Cer(d18:1/26:0)/Chol | 0.75 | 0.73 | −13.8 |
| CE 18:2/Chol | 0.67 | 0.87 | −14.0 |
| CE 20:5/LDL | 0.67 | 0.73 | −15.8 |
| CE 18:3/Chol | 0.92 | 0.80 | −16.4 |
| CE 20:5/Chol | 0.75 | 0.73 | −22.5 |
| PE 38:5/TG | 0.73 | 0.70 | −24.3 |
| CE 17:0/TG | 0.67 | 0.80 | −25.1 |
| CE 16:1/Chol | 0.67 | 0.80 | −28.3 |
| Cer(d18:1/22:0)/TG | 0.67 | 0.80 | −28.8 |
| PE 38:4/TG | 0.75 | 0.73 | −29.2 |
| Cer(d18:1/18:0)/TG | 0.67 | 0.73 | −29.3 |
| CE 22:6/TG | 0.67 | 0.73 | −30.4 |
| CE 15:0/TG | 0.73 | 0.73 | −30.4 |
| DAG 18:1/18:2/TG | 1 | 0.79 | −31.6 |
| PC 18:0/20:5/TG | 0.73 | 0.77 | −34.3 |
| PC 32:0/TG | 0.83 | 0.73 | −36.0 |
| CE 16:0/TG | 0.83 | 0.73 | −36.7 |
| Cer(d18:1/24:0)/TG | 0.83 | 0.80 | −37.7 |
| CE 20:5/TG | 0.67 | 0.80 | −38.8 |
| PC 40:6/TG | 0.83 | 0.73 | −39.3 |
| GM3-d18:1/21:0/TG | 0.75 | 0.73 | −39.6 |
| SM (d18:1/24:0) (d18:1/23:1-OH)/TG | 0.83 | 0.73 | −39.7 |
| PC 35:2 (PC O-36:2)/TG | 0.83 | 0.73 | −40.1 |
| CE 18:3/TG | 0.92 | 0.73 | −40.4 |
| PC 35:2 (PC O-34:2)/TG | 0.75 | 0.73 | −40.9 |
| PC 16:0/20:5/TG | 0.75 | 0.80 | −41.0 |
| CE 18:2/TG | 0.83 | 0.73 | −41.1 |
| CE 18:0/TG | 0.83 | 0.86 | −41.1 |
| PC 16:0/18:2/TG | 0.92 | 0.73 | −41.5 |
| PC 16:0/22:6/TG | 0.83 | 0.73 | −41.9 |
| CE 14:0/TG | 0.83 | 0.73 | −42.1 |
| PC 34:1/TG | 0.83 | 0.73 | −42.8 |
| SM (d18:1/17:0) (d18:1/16:1-OH)/TG | 0.70 | 0.75 | −42.9 |
| PC 36:5/TG | 0.75 | 0.73 | −43.1 |
| PC 38:3/TG | 0.75 | 0.73 | −43.2 |
| PC 18:0/20:3/TG | 0.83 | 0.71 | −44.8 |
| SM (d18:1/14:0) (d18:1/13:1-OH)/TG | 0.83 | 0.73 | −44.8 |
| PC 34:2/TG | 0.92 | 0.73 | −46.7 |
| SM (d18:1/23:1) (d18:1/22:2-OH)/TG | 0.75 | 0.73 | −47.7 |
| CE 16:1/TG | 0.92 | 0.80 | −48.4 |
| PC 18:2/18:2/TG | 0.75 | 0.73 | −50.9 |
| PC 32:1/TG | 0.83 | 0.80 | −59.0 |

The preferred embodiments of the invention were selected from the broad list of findings as follows. About 15 lipids or lipid ratios each with positive or negative CVD correlations were selected using highest p-values and subjectively ensuring the balanced representation of all lipid classes. Sensitivity and specificity thresholds were annotated in cases where the threshold of 60 and 70 were reached respectively. The preferred embodiment lipids, lipid-lipid ratios and lipid-clinical ratios are presented in tables 14-19.

TABLE 14

The preferred embodiment lipids selected from significant lipids detected from LURIC sample set.

| Lipid name | p-value | Percentage change | Sensitivity | Specificity |
|---|---|---|---|---|
| *Positive correlation* | | | | |
| Cer(d18:0/22:0) | 0.014688 | 43.8 | | |
| Cer(d18:0/24:0) | 0.033399 | 37.3 | | |
| Cer(d18:0/24:1) | 0.010517 | 55.2 | | |
| Cer(d18:1/16:0) | 0.001269 | 38.5 | 0.6111111 | 0.775 |
| Cer(d18:1/18:0) | 0.038491 | 31.9 | | |
| Cer(d18:1/24:1) | 0.014566 | 25.8 | | |
| GlcCer(d18:1/16:0) | 0.03569 | 22.5 | | |
| GlcCer(d18:1/18:0) | 0.046657 | 22.2 | | |
| LacCer(d18:1/18:0) | 0.046017 | 28.5 | | |
| LacCer(d18:1/20:0) | 0.044453 | 28.2 | | |
| LacCer(d18:1/22:0) | 0.017297 | 23.2 | 0.7222222 | 0.7 |
| LacCer(d18:1/24:1) | 0.024133 | 24.9 | | |
| *Negative correlation* | | | | |
| CE 16:0 | 0.01872 | −21.2 | | |
| CE 17:1 | 0.018923 | −25.0 | | |
| PC 35:3 (PC O-34:3) | 0.049614 | −23.9 | | |
| CE 14:0 | 0.03059 | −25.7 | 0.6111111 | 0.75 |
| CE 20:3 | 0.043641 | −21.5 | 0.6111111 | 0.725 |
| Total CE | 0.028927 | −21.2 | 0.6111111 | 0.7 |

TABLE 15

Preferred embodiment lipids from significant lipids detected from SHAPS sample set.

| Lipid name | p-value | Percentage change | Sensitivity | Specificity |
|---|---|---|---|---|
| *Negative correlation* | | | | |
| Cer(d18:0/24:0) | 0.007275 | −35.5 | | |
| GD3-d18:1/16:0 | 0.011309 | −25.6 | 0.8333333 | 0.71428571 |
| PC 16:0/16:1 | 0.009571 | −36.8 | | |
| PC 37:5 (PC O-38:5) | 0.013822 | −24.5 | 0.75 | 0.73333333 |
| SM (d18:1/18:1) | 0.004688 | −31.0 | 0.8333333 | 0.86666667 |
| SM (d18:1/23:1) (d18:1/22:2-OH) | 0.000416 | −32.7 | 0.8333333 | 0.73333333 |
| SM (d18:1/16:1) (d18:1/15:2-OH) | 0.008132 | −28.1 | | |
| Total GD3 | 0.011309 | −25.6 | 0.8333333 | 0.71428571 |
| CE 16:0 | 0.009455 | −19.5 | 0.8333333 | 0.8 |
| Total CE | 0.013196 | −20.6 | 0.75 | 0.93333333 |
| Total PC | 0.002012 | −26.6 | 0.8333333 | 0.8 |

TABLE 16

Preferred embodiments from significant lipid to lipid ratios detected from LURIC sample set.

| Lipid ratio name | p-value | Percentage change | Sensitivity | Specificity |
|---|---|---|---|---|
| Positive correlation | | | | |
| CE 19:1/LPC 20:4 | 0.000472 | 90.35934685 | 0.8333333 | 0.7 |
| Cer(d18:1/24:1)/LPC 18:2 | 8.77E−05 | 72.81688737 | | |
| Cer(d18:1/16:0)/LPC 18:2 | 0.000118 | 90.10795901 | | |
| PC 38:0/PC 38:5 | 0.000119 | 49.99526445 | | |
| LacCer(d18:1/24:1)/PC 16:0/20:4 | 0.00017 | 71.04956344 | | |
| GlcCer(d18:1/26:1)/SM (d18:1/24:2-OH) (d18:1/25:1) | 0.000178 | 63.26864438 | | |
| Cer(d18:1/16:0)/SM (d18:1/24:1) (d18:1/23:2-OH) | 0.000193 | 65.5335903 | | |
| Cer(d18:1/16:0)/PC 18:1/18:2 | 0.000244 | 66.68678964 | | |
| Cer(d18:1/16:0)/PC 35:3 (PC O-34:3) | 0.000253 | 119.7334815 | | |
| GlcCer(d18:1/16:0)/LPC 18:2 | 0.000319 | 76.07058679 | | |
| LacCer(d18:1/22:0)/SM (d18:1/24:0) (d18:1/23:1-OH) | 0.000383 | 55.50328917 | | |
| LacCer(d18:1/22:0)/PC 35:4 (PC O-36:4) | 0.000475 | 58.48665386 | | |
| LacCer(d18:1/24:1)/Total CE | 0.000331 | 64.00805641 | 0.8333333 | 0.725 |
| Cer(d18:1/16:0)/PC 36:3 | 0.000834 | 60.10383676 | 0.7777778 | 0.775 |
| Cer(d18:1/16:0)/LPC 18:1 | 0.0002 | 56.03521777 | 0.7777778 | 0.71052632 |
| LacCer(d18:1/22:0)/PC 16:0/20:4 | 0.000499 | 64.33099382 | | |
| Negative correlation | | | | |
| CE 16:0/Cer(d18:1/16:0) | 0.001041 | −43.89062683 | | |
| CE 18:2/Cer(d18:1/16:0) | 0.001221 | −43.8001271 | | |
| CE 20:4/GlcCer(d18:1/16:0) | 0.001478 | −41.83985223 | | |
| CE 18:1/Cer(d18:1/16:0) | 0.001789 | −45.01233662 | | |
| CE 22:6/Cer(d18:1/16:0) | 0.001806 | −40.38963291 | | |
| CE 16:1/PC 37:2 (PC O-38:2) | 0.001932 | −50.19239309 | | |
| CE 18:0/Cer(d18:1/16:0) | 0.002075 | −42.03051749 | | |
| CE 18:2/GlcCer(d18:1/16:0) | 0.002155 | −36.22537162 | | |
| CE 16:0/GlcCer(d18:1/16:0) | 0.002508 | −37.19500497 | | |
| LPC 20:4/PC 35:1 (PC O-36:1) | 0.005469 | −42.92988466 | | |
| Total CE/Total LacCer | 0.004078 | −36.83803507 | 0.8333333 | 0.725 |
| CE 20:4/Cer(d18:1/24:1) | 0.002608 | −40.26726712 | 0.7777778 | 0.7 |

TABLE 17

Preferred embodiments from significant lipid to lipid ratios detected from SHAPS sample set.

| Lipid ratio name | p-value | Percentage change | Sensitivity | Specificity |
|---|---|---|---|---|
| Positive correlation | | | | |
| Cer(d18:1/16:0)/Cer(d18:1/26:0) | 0.000462 | 37.01057987 | | |
| DAG 16:1/16:1/PC 32:1 | 0.000164 | 82.69222747 | | |
| GM3-d18:1/24:1/SM (d18:1/16:1) (d18:1/15:2-OH) | 0.000221 | 55.99413212 | 0.9166667 | 0.73333333 |
| GM3-d18:1/24:1/SM (d18:1/18:1) | 0.000235 | 57.78999778 | 0.9166667 | 0.93333333 |
| Negative correlation | | | | |
| CE 16:1/DAG 16:1/16:1 | 0.000417 | −41.20191943 | 0.9166667 | 0.92857143 |
| CE 18:2/Cer(d18:1/24:1) | 0.000881 | −31.80274825 | 0.9166667 | 0.86666667 |
| CE 18:2/Cer(d18:1/16:0) | 0.001279 | −27.54230998 | 0.9166667 | 0.8 |
| Cer(d18:1/24:0)/Cer(d18:1/24:1) | 0.002299 | −24.76608144 | | |
| Cer(d18:0/24:0)/DAG 16:1/16:1 | 0.00291 | −42.26869994 | | |
| Cer(d18:0/24:0)/Cer(d18:1/16:0) | 0.005651 | −40.35096815 | | |
| GD3-d18:1/16:0/GlcCer(d18:1/24:1) | 0.004342 | −32.0002382 | | |
| GlcCer(d18:1/26:0)/GlcCer(d18:1/26:1) | 0.00263 | −24.97108611 | | |
| GM3-d18:1/22:1/GM3-d18:1/24:1 | 2.27E−05 | −22.64333818 | 0.9166667 | 0.93333333 |
| GM3-d18:1/20:0/GM3-d18:1/24:1 | 4.05E−05 | −25.790617 | 1 | 0.73333333 |
| GM3-d18:1/18:0/GlcCer(d18:1/24:1) | 0.003743 | −27.07575879 | | |
| PC 16:0/18:2/PE 36:2 | 0.003019 | −30.0252666 | | |
| SM (d18:1/23:1) (d18:1/22:2-OH)/SM (d18:1/24:1) (d18:1/23:2-OH) | 0.002698 | −30.33837495 | | |
| CE 16:1/CE 20:3 | 0.003774 | −33.87140598 | 0.9166667 | 0.8 |

TABLE 17-continued

Preferred embodiments from significant lipid to lipid ratios detected from SHAPS sample set.

| Lipid ratio name | p-value | Percentage change | Sensitivity | Specificity |
|---|---|---|---|---|
| CE 16:1/Cer(d18:1/16:0) | 0.005002 | −40.55114395 | 0.9166667 | 0.73333333 |
| CE 16:1/LPC 16:0 | 0.004835 | −33.21631623 | 0.9166667 | 0.73333333 |

TABLE 18

Preferred embodiments from significant lipid to clinical ratios from LURIC sample set.

| Lipid name/Clinical measurement | p-value | Percentage change | Sensitivity | Specificity |
|---|---|---|---|---|
| *Positive correlation* | | | | |
| Cer(d18:0/22:0)/apolipoprotein A-I (mg/dL) | 0.002679 | 62.12399702 | | |
| Cer(d18:0/24:1)/cholesterol ester (mg/dL) | 0.003755 | 66.37295698 | | |
| Cer(d18:1/16:0)/apolipoprotein A-I (mg/dL) | 0.000368 | 61.54836937 | | |
| Cer(d18:1/24:1)/apolipoprotein A-I (mg/dL) | 0.000839 | 45.11297635 | | |
| GlcCer(d18:1/16:0)/apolipoprotein A-I (mg/dL) | 0.001748 | 40.95349137 | | |
| GlcCer(d18:1/18:0)/apolipoprotein A-I (mg/dL) | 0.002508 | 39.77171523 | 0.7222222 | 0.7 |
| LacCer(d18:1/22:0)/apolipoprotein A-I (mg/dL) | 0.000804 | 44.38027847 | | |
| LacCer(d18:1/22:0)/HDL cholesterol ester (mg/dL) | 0.001926 | 52.8411569 | | |
| Cer(d18:1/24:1)/HDL cholesterol ester (mg/dL) | 0.00216 | 54.64058021 | 0.7222222 | 0.725 |
| LacCer(d18:1/22:0)/total cholesterol (EDTA) (mg/dL) | 0.00316 | 39.0400307 | | |
| Cer(d18:1/24:1)/total cholesterol (EDTA) (mg/dL) | 0.001945 | 34.55989651 | 0.7222222 | 0.7 |
| Cer(d18:1/16:0)/apolipoprotein A-II (mg/dL) | 0.000292 | 67.12282079 | 0.7222222 | 0.725 |
| Cer(d18:1/22:0)/apolipoprotein A-II (mg/dL) | 0.002248 | 43.7098503 | 0.7222222 | 0.7 |
| LacCer(d18:1/24:1)/apolipoprotein A-I (mg/dL) | 0.001171 | 43.77660659 | | |
| *Negative correlation* | | | | |
| LPC 18:2/apolipoprotein C-III (mg/dL) | 0.009298 | −37.0 | | |
| SM (d18:1/25:1) (d18:1/24:2-OH)/free fatty acids (mmol/L) | 0.009794 | −51.0 | 0.7222222 | 0.75 |
| CE 18:2/apolipoprotein C-III (mg/dL) | 0.011129 | −32.8 | | |
| CE 20:4/apolipoprotein C-III (mg/dL) | 0.012993 | −34.4 | | |

TABLE 19

Preferred embodiments from significant lipid to clinical ratios from SHAPS sample set.

| Lipid name/Clinical measurement | p-value | Percentage change | Sensitivity | Specificity |
|---|---|---|---|---|
| *Positive correlation* | | | | |
| Cer(d18:1/16:0)/HDL | 0.036889 | 45.8 | | |
| Cer(d18:1/24:1)/HDL | 0.016111 | 59.0 | 0.8333333 | 0.8 |
| DAG 16:1/16:1/HDL | 0.012917 | 53.8 | 0.6666667 | 0.78571429 |
| GlcCer(d18:1/24:1)/HDL | 0.013245 | 63.3 | 0.8333333 | 0.8 |
| GlcCer(d18:1/26:1)/HDL | 0.043859 | 49.4 | | |
| GM3-d18:1/16:0/HDL | 0.038989 | 25.8 | | |
| GM3-d18:1/24:1/HDL | 0.00268 | 51.0 | | |
| Cer(d18:1/24:1)/Chol | 0.005275 | 26.8 | 0.9166667 | 0.73333333 |
| GM3-d18:1/24:2/HDL | 0.015381 | 31.6 | | |
| *Negative correlation* | | | | |
| Cer(d18:0/24:0)/TG | 0.00017 | −50.81345375 | | |
| DAG 18:1/18:2/TG | 0.001479 | −31.57202102 | 1 | 0.78571429 |
| PC 18:0/20:3/TG | 0.001935 | −44.80069954 | 0.8333333 | 0.71428571 |
| CE 18:2/TG | 0.002102 | −41.06062212 | 0.8333333 | 0.73333333 |
| SM (d18:1/18:1)/TG | 0.005568 | −44.15754076 | | |
| Cer(d18:1/24:0)/TG | 0.006103 | −37.69337481 | 0.8333333 | 0.8 |
| PI 38:3/TG | 0.006463 | −41.87676619 | | |

TABLE 19-continued

Preferred embodiments from significant lipid to clinical ratios from SHAPS sample set.

| Lipid name/Clinical measurement | p-value | Percentage change | Sensitivity | Specificity |
|---|---|---|---|---|
| GD3-d18:1/16:0/TG | 0.008681 | −43.54025662 | | |
| LacCer(d18:1/22:0)/TG | 0.012168 | −41.61161247 | | |
| GM3-d18:1/21:0/TG | 0.014997 | −39.62591911 | 0.75 | 0.73333333 |
| GD1-d18:1/16:0/TG | 0.024027 | −48.92359261 | | |
| GM3-d18:1/18:0/TG | 0.02444 | −35.77082537 | | |
| PC 16:0/18:2/TG | 0.001991 | −41.45635691 | 0.9166667 | 0.73333333 |
| CE 16:1/TG | 0.002007 | −48.39087067 | 0.9166667 | 0.8 |
| SM (d18:1/14:0) (d18:1/13:1-OH)/TG | 0.008912 | −44.8243579 | 0.8333333 | 0.73333333 |
| SM (d18:1/23:1) (d18:1/22:2-OH)/TG | 0.00543 | −47.70207646 | 0.75 | 0.73333333 |
| PC 18:2/18:2/TG | 0.009381 | −50.91970106 | 0.75 | 0.72727273 |
| CE 16:1/Chol | 0.00839 | −28.33597812 | | |

TABLE 20

Top five candidates from each category, if available, are listed. The best candidates were selected based on following criteria: t-test p-value ≤0.05 and sensitivity ≥60% and specificity ≥70%.

| Measurement type | Measurement name | P-value | Percentage change | Sensitivity | Specificity | Threshold | Change direction |
|---|---|---|---|---|---|---|---|
| Lipid conc. | Cer(d18:1/16:0) | 0.001 | 38.5 | 0.61 | 0.78 | 0.336 µM | Increased |
| Lipid conc. | LacCer(d18:1/22:0) | 0.017 | 23.2 | 0.72 | 0.70 | 0.879 µM | Increased |
| Lipid conc. | LacCer(d18:1/24:1) | 0.024 | 24.9 | 0.61 | 0.78 | 3.389 µM | Increased |
| Lipid conc. | CE 14:0 | 0.031 | −25.7 | 0.61 | 0.75 | 29.43 µM | Decreased |
| Lipid conc. | CE 20:3 | 0.044 | −21.5 | 0.61 | 0.73 | 42.63 µM | Decreased |
| Lipid ratio | Cer(d18:1/16:0)/LPC 18:1 | 0.000 | 56.0 | 0.78 | 0.71 | 0.01 | Increased |
| Lipid ratio | LacCer(d18:1/24:1)/Total CE | 0.000 | 64.0 | 0.83 | 0.73 | 0.0006 | Increased |
| Lipid ratio | CE 19:1/LPC 20:4 | 0.000 | 90.4 | 0.83 | 0.70 | 9.5 | Increased |
| Lipid ratio | Cer(d18:1/16:0)/PC 36:3 CE | 0.001 | 60.1 | 0.78 | 0.78 | 0.0008 | Increased |
| Lipid ratio | 20:4/Cer(d18:1/24:1) | 0.003 | −40.3 | 0.78 | 0.70 | 141.50 | Decreased |
| Lipid-clinical ratio | GlcCer(d18:1/18:0)/apolipoprotein A-I(mg/dL) | 0.003 | 39.8 | 0.72 | 0.70 | 0.0018 | Increased |

Lipidomic analysis proved to be efficient in identifying novel plasma biomarkers for atherosclerotic disease. FIG. 1 illustrates the great potential of lipidomic markers and indicates the superiority of the new potentials markers over know clinically used markers such as LDL-cholesterol.

As the absolute molecular lipid plasma concentration differences in general between healthy individuals and atherosclerotic patients seem to be between 30-70%, it might be reasonable to calculate and use different ratios instead of absolute concentrations only. As lipoprotein particles (e.g. LDL, HDL, and VLDL) are serving as carriers for most of the lipids in the blood stream it is appropriate to relate molecular lipid concentrations to lipoprotein data. Thus, the molecular lipid to HDL-cholesterol, LDL-cholesterol, apolipoprotein A-I and apolipoprotein B ratios were calculated, which in fact turned out to be better biomarkers than absolute plasma concentrations alone.

Figure 2:
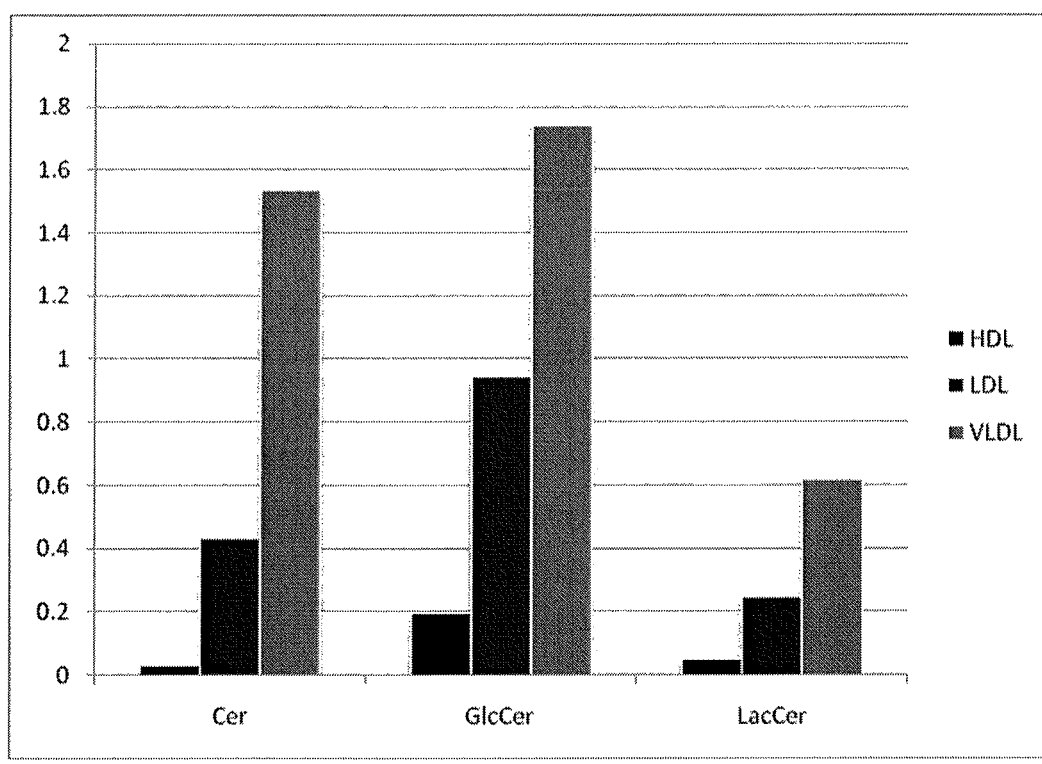
FIG. 2. Ceramide and cerebroside concentrations in lipoprotein fractions derived from mildly hypercholesterolemic but otherwise healthy subjects (n=18). This data shows that ceramides and cerebrosides are bound to apolipoprotein particles in blood. Thus it might be informative to analyze biomarker lipids also in lipoprotein fractions in order to get more precise information as HDL particles are related to reverse lipid transport and LDL particles are transporting lipids from liver to peripheral tissues. It is possible, that the diagnostic/predictive value of HDL bound lipid may be different to that of LDL bound.

The plaque data shows that human atherosclerotic plaques are enriched in lipids such as ceramides and cerebrosides. Thus, lowering the content of these lipids in artery walls by reducing their synthesis in situ or in other tissues (e.g. liver), blocking transport of these lipids to vessel wall (e.g. by LDL or macrophage) or increasing their transport from the artery wall will inhibit plaque and atherosclerosis development and thus reduce the risk of CVD. Statins and other lipid metabolism affecting drugs can be used to modify ceramide and cerebroside accumulation in human atherosclerotic plaques. Biomarker lipids associate significantly with apolipoproteins (ApoA1, ApoA2 and ApoB) and earlier data shows that they (e.g. ceramides and cerebrosides) are bound to lipoprotein particles (VLDL, LDL and HDL) (FIG. 2), it is obvious that biomarker lipid measurement directly in lipoprotein fraction will be more accurate than total plasma or serum. Therefore, molecular lipid levels in different lipoprotein fractions can be used as significant biomarkers for CVD risk.

Figure 3:
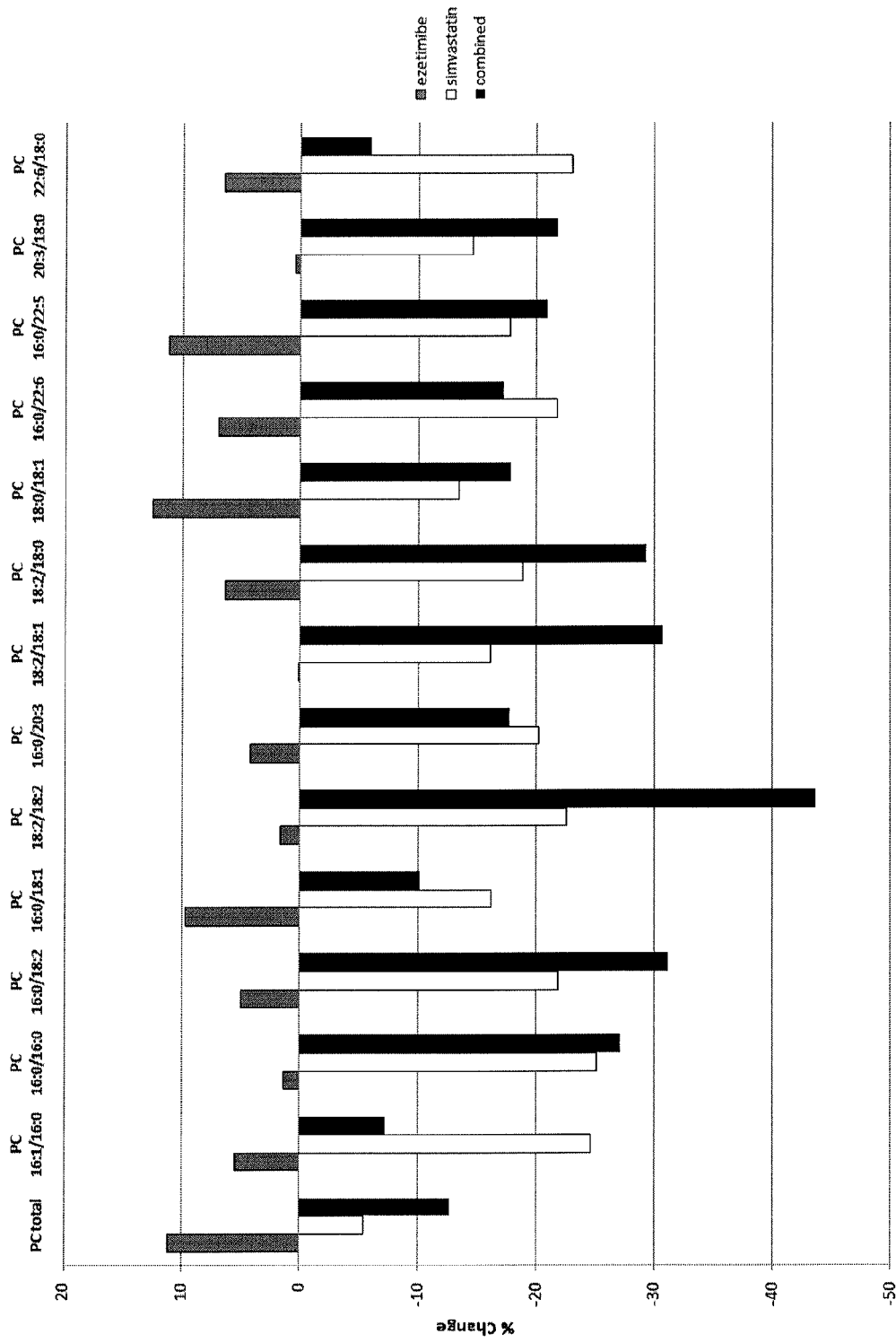
FIG. 3. The effect of ezetimibe 10 mg, simvastatin 40 mg or a combination of ezetimibe 10 mg and simvastatin 40 mg on the plasma lipidome was studied in mildly hypercholesterolemic but otherwise healthy subjects (n=24 in each treatment group). This figure illustrates treatment specific changes in molecular phospholipids suggesting that lipidomic measurement can be used to characterize the efficacy of lipid modifying treatments more closely than with traditional clinical biochemistry.

Lipidomic measurement can also be used to characterize the efficacy of e.g. plasma lipid modifying compounds such as statins and ezetimibe (FIG. 3). These data can now also be linked to an individual's lipid biomarker concentrations/profile and thus select the right/optimal/best/targeted treatment to each patient.

Molecular lipid to molecular lipid ratio could be an important indicator of cellular lipid metabolism including e.g. enzyme activities in the lipid metabolism pathways. Thus, these ratios may provide more information as the absolute plasma concentrations of the molecular lipids alone. In fact, a number of ratios between the concentrations of different molecular lipids outperformed absolute plasma concentrations as disease biomarkers in CVD patients.

As the detected lipids are carried in the lipoprotein particles (LDL, VLDL and HDL) it is obvious that the corresponding lipoprotein fraction concentrations will even improve the prediction potential of molecular lipids from the results of the present study in total serum/plasma samples.

The lipid lowering drug efficiency measurements have so far been based on LDL-C and HDL-C assays. As the inventors have herein observed more potential biomarkers that predict CVD risk better than these classical analyses future drug efficiency profiling should be based on new sensitive and specific biomarkers that are more directly related to cardiovascular risk than LDL-C.

Those skilled in the art will recognize, or be able to ascertain using no more than routine experimentation, numerous equivalents to the specific embodiments described herein both in the Examples in in the body of the entire patent description. Such equivalents are considered to be within the scope of this invention and are covered by the following claims.

The invention claimed is:

1. A method for determining whether a subject is at risk, to develop one or more complications of cardiovascular disease (CVD), wherein the one or more complications are death, myocardial infarction, acute myocardial infarction, angina pectoris, transient ischemic attack, or stroke, said method comprising:
    (a) determining in a sample from said subject one or more lipid-lipid ratio(s), wherein (an) increased or decreased lipid-lipid ratio(s) in said sample, when compared to a control sample, is (are) indicative of said subject having an increased risk of developing the one or more complications of CVD,
        wherein the one or more lipid-lipid ratio(s) whose increase(s) is (are) compared to the control is (are) selected from:
        Cer(d18:1/16:0)/PC 18:1/18:2,
        Cer(d18:1/16:0)/LPC 18:1,
        Cer(d18:1/16:0)/PC 36:3,
        Cer(d18:1/24:1)/LPC 18:2,
        Cer(d18:1/16:0)/LPC 18:2,
        Cer(d18:1/16:0)/SM (d18:1/24:1)(d18:1/23:2-OH),
        Cer(d18:1/16:0)/PC 35:3 (PC O-34:3), and
        Cer(d18:1/16:0)/Cer(d18:1/26:0);
        and wherein the one or more lipid-lipid ratios) whose decrease(s) is (are) compared to the control is e) selected from:
        Cer(d18:1/24:0)/Cer(d18:1/24:1),
        Cer(d18:0/24:0)/Cer(d18:1/16:0),
        CE 16:0/Cer(d18:1/16:0),
        CE 18:1/Cer(d18:1/16:0),
        CE 22:6/Cer(d18:1/16:0),
        CE 18:0/Cer(d18:1/16:0),
        CE 20:4/Cer(d18:1/24:1),
        CE 18:2/Cer(d18:1/24:1),
        CE 18:2/Cer(d18:1/16:0),
        Cer(d18:0/24:0)/DAG 16:1/16:1, and
        CE 16:1/Cer(d18:1/16:0); or
    (b) determining in a sample from said subject one or more lipid-clinical concentration ratio(s), wherein (an) increased or decreased lipid-clinical concentration ratio(s) in said sample, when compared to a control sample, is (are) indicative of said subject having an increased risk of developing the one or more complications of CVD,
        wherein the one or more lipid-clinical concentration ratio(s) whose increase(s) is (are) compared to the control is (are) selected from:
        Cer(d18:1/16:0)/apolipoprotein A-I (mg/dL),
        Cer(d18:1/16:0)/apolipoprotein A-II (mg/dL),
        Cer(d18:1/16:0)/HDL,
        Cer(d18:0/22:0)/apolipoprotein A-I (mg/dL),
        Cer(d18:0/24:1)/cholesterol ester (mg/dL),
        Cer(d18:1/24:1)/apolipoprotein A-I (mg/dL),
        Cer(d18:1/24:1)/HDL cholesterol ester (mg/dL),
        Cer(d18:1/24:1)/total cholesterol (EDTA) (mg/dL),
        Cer(d18:1/22:0)/apolipoprotein A-II (mg/dL),
        Cer(d18:1/24:1)/HDL, and
        Cer(d18:1/24:1)Chol;
        and wherein the one or more lipid-clinical concentration ratio(s) whose decrease(s) is (are) compared to the control is (are) selected from:
        Cer(d18:0/24:0)/TG and
        Cer(d18:1/24:0)/TG.

2. The method of claim 1, wherein
    (a) the lipid-lipid ratio whose increase is compared to the control is selected from:
        Cer(d18:1/16:0)/LPC 18:1 and
        Cer(d18:1/16:0)/PC 36:3; and/or
    (b) the lipid-lipid ratio whose decrease is compared to the control is:
        CE 20:4/Cer(d18:1/24:1).

3. The method of claim 1, wherein the one or more lipid-lipid ratios comprises at least 2, at least 3, at least 4, at least 5 at least 6, at least 7, or at least 8 lipid-lipid ratios, and
    wherein the one or more lipid-clinical ratios comprises at least 2, at least 3, at east 4, at least 5, at least 6, at least 7, or at least 8 lipid-clinical concentration ratios.

4. The method of claim 1, wherein
    (a) said CVD is characterized by coronary artery disease, peripheral artery disease, a stroke and/or CVD death; and/or
    (b) said subject has atherosclerosis; or
    (c) said subject does not have atherosclerosis.

5. The method of claim 1, wherein
    (a) the method further comprises determining the serum level of total cholesterol, low-density lipoprotein cholesterol (LDL-C), high-density lipoprotein cholesterol (HDL-C), Apolipoprotein B (ApoB) and/or Apolipoprotein C-III (ApoC-III) in said sample; and/or (b) the subject does not have elevated serum levels of one or more of total cholesterol, low-density lipoprotein cholesterol (LDL-C), Apolipoprotein C-III (ApoC-III) or Apolipoprotein B (ApoB), or a decreased serum level of HDL-cholesterol (HDL-C).

6. The method of claim 1, wherein said subject
(a) is being or has been treated with one or more statins and/or any other HMG-CoA reductase inhibitor; or
(b) has not yet undergone statin therapy or therapy with any other HMG-CoA reductase inhibitor.

7. The method of claim 1, wherein the lipid-lipid ratio(s) or the lipid-clinical concentration ratio(s) is (are) determined by using mass spectrometry, nuclear magnetic resonance spectroscopy, fluorescence spectroscopy or dual polarisation interferometry, a high performance separation method, an immunoassay and/or with a binding moiety capable of specifically binding the analyte.

8. The method of claim 6, wherein the statin is selected from the group consisting of atorvastatin, cerivastatin, fluvastatin, fluvastatin XL, lovastatin, pitavastatin, pravastatin, rosuvastatin and/or simvastatin.

9. The method of claim 1, wherein the subject has suffered from a cardiovascular disease event.

10. The method of claim 1 wherein the control sample is from a healthy individual or a generalized population of healthy individuals.

11. The method of claim 1, wherein the one or more complications of atherosclerosis or CVD to be prevented or treated is one or more of: myocardial infarction (MI), AMI, angina pectoris, transient ischemic attack (TIA) and stroke; and wherein the one or more complications of atherosclerosis or CVD to he prevented may he death.

12. The method of claim 1, wherein the one or more lipid-lipid ratios whose decrease is compared to the control is Cer(d18:1/24:0)/Cer(d18:1/24:1).

13. The method of claim 12, wherein the one or more lipid-lipid ratios whose increase is compared to the control further comprises Cer(d18:1/16:0)/Cer(d18:1/26:0).

14. The method of claim 10, where the control sample is a blood sample or a serum sample.

15. The method of claim 1, wherein the sample is blood, serum or plasma and wherein the lipid-lipid ratio(s) or the lipid-clinical concentration ratio(s) is (are) determined by using mass spectrometry.

* * * * *

UNITED STATES PATENT AND TRADEMARK OFFICE
CERTIFICATE OF CORRECTION

PATENT NO. : 9,046,538 B2
APPLICATION NO. : 13/695766
DATED : June 2, 2015
INVENTOR(S) : Reijo Laaksonen et al.

It is certified that error appears in the above-identified patent and that said Letters Patent is hereby corrected as shown below:

On the title page, item (30) Foreign Application Priority Data, "10162066" should read --10162066.4--.

In the Claims

Column 57, line 44, Claim 1, "risk," should read --risk--.

Column 58, line 2, Claim 1, "e)" should read --(are)--.

Signed and Sealed this
Twenty-second Day of September, 2015

Michelle K. Lee
*Director of the United States Patent and Trademark Office*